US006573051B2

United States Patent
Alsmadi et al.

(10) Patent No.: US 6,573,051 B2
(45) Date of Patent: Jun. 3, 2003

(54) OPEN CIRCLE PROBES WITH INTRAMOLECULAR STEM STRUCTURES

(75) Inventors: Osama A. Alsmadi, Hamden, CT (US); Patricio Abarzua, West Caldwell, NJ (US)

(73) Assignee: Molecular Staging, Inc., New Haven, CT (US)

( * ) Notice: Subject to any disclaimer, the term of this patent is extended or adjusted under 35 U.S.C. 154(b) by 0 days.

(21) Appl. No.: 09/803,713

(22) Filed: Mar. 9, 2001

(65) Prior Publication Data

US 2003/0022167 A1 Jan. 30, 2003

(51) Int. Cl.⁷ .................. C12Q 1/68; C12P 19/34; C07H 21/04
(52) U.S. Cl. .................. 435/6; 435/91.1; 435/91.2; 536/24.3
(58) Field of Search .................. 435/6, 91.2, 91.1; 536/24.3

(56) References Cited

U.S. PATENT DOCUMENTS

| | | | |
|---|---|---|---|
| 4,883,750 A | 11/1989 | Whiteley et al. | 435/6 |
| 4,965,188 A | 10/1990 | Mullis et al. | 435/6 |
| 5,001,050 A | 3/1991 | Blanco et al. | 435/5 |
| 5,198,543 A | 3/1993 | Blanco et al. | 536/23.2 |
| 5,242,794 A | 9/1993 | Norman et al. | 536/25 |
| 5,354,668 A | 10/1994 | Auerbach | 435/91.1 |
| 5,409,818 A | 4/1995 | Davey et al. | 435/91.21 |
| 5,455,166 A | 10/1995 | Walker | 435/91.2 |
| 5,521,065 A | 5/1996 | Whiteley et al. | 435/6 |
| 5,591,609 A | 1/1997 | Auerbach | 435/91.2 |
| 5,614,389 A | 3/1997 | Auerbach | 435/91.2 |
| 5,714,320 A | 2/1998 | Kool | 435/6 |
| 5,733,733 A | 3/1998 | Auerbach | 435/6 |
| 5,854,033 A | * 12/1998 | Lizardi | 435/91.2 |
| 5,874,260 A | 2/1999 | Cleuziat et al. | |
| 5,925,517 A | 7/1999 | Tyagi et al. | |
| 6,365,729 B1 | * 4/2002 | Tyagi et al. | 536/24.33 |

FOREIGN PATENT DOCUMENTS

| | | | | |
|---|---|---|---|---|
| AU | 649066 | | 5/1994 | C12Q/1/68 |
| EP | 0 356 021 A2 | | 2/1990 | C12Q/1/68 |
| EP | 0 439 182 B1 | | 7/1991 | C12Q/1/68 |
| EP | 0 505 012 A2 | | 9/1992 | C12Q/1/68 |
| JP | 4262799 | | 9/1992 | |
| JP | 4304900 | | 10/1992 | |
| WO | WO 92/01813 | | 2/1992 | C12Q/1/68 |
| WO | WO 94/24312 | | 10/1994 | C12Q/1/68 |

(List continued on next page.)

OTHER PUBLICATIONS

Abravaya et al., "Detection of point mutations with a modified ligase chain reaction (Gap–LCR)", *Nucleic Acids Res.* 23(4): 675–682 (1995).

(List continued on next page.)

*Primary Examiner*—Kenneth R. Horlick
*Assistant Examiner*—Teresa Strzelecka
(74) *Attorney, Agent, or Firm*—Needle & Rosenberg, P.C.

(57) ABSTRACT

Disclosed are compositions and methods for reducing or eliminating generation of unwanted, undesirable, or non-specific amplification products in nucleic acid amplification reactions, such as rolling circle amplification. One form of composition is an open circle probe that can form an intramolecular stem structure, such as a hairpin structure, at one or both ends. The stem structure allows the open circle probe to be circularized when hybridized to a legitimate target sequence but results in inactivation of uncircularized open circle probes. This inactivation, which preferably involves stabilization of the stem structure, extension of the end of the open circle probe, or both, reduces or eliminates the ability of the open circle probe to prime nucleic acid synthesis or to serve as a template for rolling circle amplification. The disclosed method is useful for detection, quantitation, and/or location of any desired analyte, such as proteins and peptides.

105 Claims, 4 Drawing Sheets

FOREIGN PATENT DOCUMENTS

| WO | WO 95/03432 | 2/1995 | ............ C12Q/1/70 |
|----|-------------|--------|------------------------|
| WO | WO 95/22623 | 8/1995 | ............ C12Q/1/68 |
| WO | WO 95/35390 | 12/1995 | ............ C12Q/1/68 |
| WO | WO 97/20948 | 6/1997 | ............ C12Q/1/68 |
| WO | WO 97/42346 | 11/1997 | ............ C12Q/1/68 |

OTHER PUBLICATIONS

Aliotta, J.M., et al., "Thermostable Bst DNA polymerase lacks a 3'–5' proofreading exonuclease activity," *Genet. Anal.* 12:185–195 (1996).

Alves and Carr, "Dot blot detection of point mutations with adjacently hybridising synthetic oligonucleotide probes", *Nucleic Acids Res.* 16(17): 8723 (1988).

Arnold et al., "Assay Formats Involving Acridinium–Ester–Labeled DNA Probes", *Clin. Chem.* 35(8): 1588–1594 (1989).

Barany, "Genetic disease detection and DNA amplification using cloned thermostable ligase", *Proc. Natl. Acad Sci. USA* 88: 189–193 (1991).

Bertina et al., "Mutation in blood coagulation factor V associated with resistance to activated protein C", *Nature* 369:64–67 (1994).

Birkenmeyer and Mushahwar, "DNA probe amplification methods", *Journal of Virological Methods* 35: 117–126 (1991).

Blanco and Salas, "Characterization and purification of phage ø29–encoded DNA polymerase required for the initiation of replication", *Proc. Natl. Acad Sci. USA* 81: 5325–5329 (1984).

Blanco et al., "Highly Efficient DNA Synthesis by the Phage ø29 DNA Polymerase", *Journal of Biological Chemistry* 264(15): 8935–8940 (1989).

Blanco et al., "Terminal protein–primed DNA amplification", *Proc. Natl. Acad Sci. USA* 91: 12198–12202 (1994).

Boehmer and Lehman, "Herpes Simplex Virus Type 1 ICP8: Helix–Destabilizing Properties", *Journal of Virology* 67(2): 711–715 (1993).

Broude et al., "Enhanced DNA sequencing by hybridization", *Proc. Natl. Acad Sci. USA* 91: 3072–3076 (1994).

Burgess and Jacutin, "A new photolabile protecting group for nucleotides" *Am. Chem Soc. Abstracts,* vol. 221, abstract 281 (1996).

Butler and Chamberlin, "Bacteriophage SP6–specific RNA Polymerase", *Journal of Biological Chemistry* 257: 5772–5778 (1982).

Chatterjee et al., "Cloning and overexpression of the gene encoding bacteriophage T5 DNA polymerase", *Gene* 97: 13–19 (1991).

Chetverina, H., et al., "Cloning of RNA molecules in vitro," *Nucleic Acids Research* 21:2349–2353 (1993)., Daubendiek, S.L., et al., "Generation of catalytic RNAs by rolling transcription of synthetic DNA nanocircles," *Nature Biotechnology* 15:273–277 (1997).

Daubendiek, S.L., et al., "Rolling–Circle RNA Synthesis: Circular Oligonucleotides as Efficient Substrates for T7 RNA Polymerase," *J. Am. Chem Soc.* 117:7818–7819 (1995).

Davanloo et al., "Cloning and expression of the gene for bacteriophage T7 RNA polymerase", *Proc. Natl. Acad. Sci. USA* 81: 2035–2039 (1984).

DYNAL Technical Handbook "Biomagnetic Techniques in Molecular Biology" (DYNAL A.S., 1995).

Ernst et al., "Cyanine dye labeling reagents for sulfhydryl groups" *Cytometry* 10:3–10 (1989).

Fire and Xu, "Rolling replication of short DNA circles", *Proc. Natl. Acad Sci. USA* 92: 4641–4645 (1995).

Gasparro et al., "Site–specific targeting of psoralen photoadducts with a triple helix–forming oligonucleotide: characterization of psoralen monoadduct and crosslink formation" Nucleic Acids Research 22(14): 2845–2852 (1994).

Gerdes, M.G., et al., "Dynamic changes in the higher–level chromatin organization of specific sequences revealed by in situ hybridization in nuclear halos," *J. Cell Biol.* 126:289–304 (1994).

Gunji et al., "Correlation Between the Serum Level of Hepatitis C Virus RNA and Disease Activities in Acute and Chronic Hepatitis C", *Int. J. Cancer* 52(5): 726–730 (1992).

Guo, Z., et al., "Enhanced discrimination of single nucleotide polymorphisms by artificial mismatch hybridization," *Nature Biotechnology* 15:331–335 (1997).

Guo, et al., "Direct fluorescence analysis of genetic polymorphisms by hybridization with oligonucleotide arrays on glass supports", *Nucleic Acids Res.* 22(24): 5456–5465 (1994).

Gupta et al., "Ninth International Conference on AIDS/ Fourth STD World Congress", Jun. 6–11, 1993, Berlin, Germany.

Hacia, J.G., et al., "Detection of heterozygous mutations in BRCA1 using high density oligonucleotide arrays and two-color fluorescence analysis," *Nature Genetics* 14:441–447, (1996).

Hagiwara et al., "Quantitation of hepatitis C Virus RNA in Serum of Asymptomatic Blood Donors and Patients with Type C Chronic Liver Disease", *Hepatology* 17(4): 545–550 (1993).

Hanvey et al., "Antisense and Antigene Properties of Peptide Nucleic Acids", *Science* 258: 1481–1485 (1992).

Hata et al., "Structure of the Human Ornithine Transcarbamylase Gene", *J. Biochem.* 103: 302–308 (1988).

Hendrickson et al., "High sensitivity multianalyte immunoassay using covalent DNA–labeled antibodies and polymerase chain reaction", *Nucleic Acids Res.* 23(3): 522–529 (1995).

Holloway et al., "An exonuclease–amplification coupled capture technique improves detection of PCR product", *Nucleic Acids Research* 21: 3905–3906 (1993).

Hoy and Schimke, "Bromodeoxyuridine/DNA analysis of replication in CHO cells after exposure to UV light", *Mutation Research* 290: 217–230 (1993).

Hsuih et al., "Quantitative Detection of HCV RNA Using Novel Ligation–Dependent Polymerase Chain Reaction", *American Association for the Study of Liver Diseases,* (Chicago, IL, Nov. 3–7, 1995) [poster abstract].

Itakura et al., "Synthesis and Use of Synthetic Oligonucleotides", *Annual Review of Biochemistry* 53: 323–356 (1984).

Jacobsen et al., "The N–Terminal Amino–Acid Sequences of DNA Polymerase I from *Escherichia coli* and of the Large and the Small Fragments Obtained by a Limited Proteolysis", *Eur. J. Biochem.* 45: 623–627 (1974).

Johnstone and Thorpe, *Immunochemistry In Practice* (Blackwell Scientific Publication, Oxford, England, 1987) pp. 209–216 and 241–242.

Jung et al., "Bacteriophage PRDI DNA polymerase: Evolution of DNA polymerases", *Proc. Natl. Acad. Sci. USA* 84: 8287 (1987).

Kaboord and Benkovic, "Accessory proteins function as matchmakers in the assembly of the T4 DNA polymerase holoenzyme", *Current Biology* 5: 149–157 (1995).

Kälin et al., "Evaluation of the ligase chain reaction (LCR) for the detection of point mutations", *Mutation Research* 283(2): 119–123 (1992).

Kaplan et al., "Rapid photolytic release of adenosine 5'–triphosphate from a protected analogue: utilization by the Na:K pump of human red blood cell ghosts" *Biochem.* 17:1929–1935 (1978).

Kellogg et al., "TaqStart Antibody™: "Hot Start" PCR Facilitated by a Neutralizing Monoclonal Antibody Directed Against Taq DNA Polymerase", *BioTechniques* 16(6): 1134–1137 (1994).

Kerkhof, "A Comparison of Substrates for Quantifying the Signal from a Nonradiolabeled DNA Probe", *Analytical Biochemistry* 205: 359–364 (1992).

Khrapko et al., "Hybridization of DNA with Oligonucleotides Immobilized in Gel: A Convenient Method for Detecting Single Base Substitutions", *Molecular Biology (Mosk) (USSR)* 25: 718–730 (1991).

King et al., "Bridging the Gap", *Journal of Biological Chemistry* 269(18): 13061–13064 (1994).

Kong et al., "Characterization of a DNA Polymerase from the Hyperthermophile Archaea *Thermococcus litoralis*", *Journal of Biological Chemistry* 268: 1965–1975 (1993).

Kool, E.T., "Circular Oligonucleotides; New Concepts in Oligonucleotide Design," *Annual Rev. Biomol. Struct.* 25:1–28 (1996).

Kunkel et al., "Rapid and Efficient Site–Specific Mutagenesis without Phenotype Selection", *Methods in Enzymology* 154:367–382 (1987).

Lamture et al., "Direct detection of nucleic acid hybridization on the surface of a charge coupled device" *Nucleic Acids Research* 22(11):2121–2125 (1994).

Landgren et al., "A Ligase–Mediated Gene Detection Technique", *Science* 241: 1077–1080 (1988).

Landegren, "Molecular mechanics of nucleic acid sequence amplification," *Trends Genetics* 9:199–202 (1993).

Langer et al., "Enzymatic synthesis of biotin–labeled polynucleotides: Novel nucleic acid affinity probes", *Proc. Natl. Acad. Sci. USA* 78(11): 6633–6637 (1981).

Panasnko et al., A Simple, Three–Step Procedure for the Large Scale Purification of DNA Ligase from a Hybrid λ Lysogen Construction in Vitro, *Journal Biological Chemistry* 253: 4590–4592 (1978).

Pease et al., "Light–generated oligonucleotide arrays for rapid DNA sequence analysis", *Proc. Natl. Acad. Sci. USA* 91(11): 5022–5026 (1994).

Piatak et al., "High Levels of HIV–1 in Plasma During All Stages of Infection Determined by Competitive PCR", *Science* 259(5102): 1749–1754 (1993).

Pillai et al., "Photoremovable protecting groups in organic synthesis" *Synthesis* 1–26 (1980).

Pokrovskaya and Gurevich, "In Vitro Transcription: Preparative RNA Yields in Analytical Scale Reactions", *Analytical Biochemistry* 220: 420–423 (1994).

Prakash, G., et al., "Structural effects in the recognition of DNA by circular oligonucleotides," *J. Amer. Chem. Soc.* 114:3523–3527 (1992).

Richards, B., et al., "Conditional mutator phenotypes in hMS2H2–deficient tumor cell lines," *Science* 277:1523–1526 (1997).

Ried et al., "Simultaneous visualization of seven different DNA probes by in situ hybridization using combinatorial fluorescence and digital imaging microscopy", *Proc. Natl. Acad. Sci. USA* 89(4): 1388–1392 (1982).

Rigler and Romano, "Differences in the Mechanism of Stimulation of T7 DNA Polymerase by Two Binding Modes of *Escherichia coli* Single–stranded DNA–binding Protein", *Journal of Biological Chemistry*, 270(15): 8910–8919 (1995).

Rychlik et al., "Optimization of the annealing temperature for DNA amplification in vitro", *Nucleic Acids Research* 18(21): 6409–6412 (1990).

Rys and Persing, "Preventing False Positivies: Quantitative Evaluation of Three Protocols for Inactivation of Polymerase Chain Reaction Amplification Products", *Journal of Clinical Microbiology* 31(9): 2356–2360 (1993).

Saksela et al., "Human immunodeficiency virus type 1 mRNA expression in peripheral blood cells predicts disease progression independently of the numbers of $CD4^+$ lymphocytes", *Proc. Natl. Acad. Sci. USA* 91(3): 1104–1108 (1994).

Sambrook et al., "Molecular Cloning: A Laboratory Manual, Second Edition", (*Cold Spring Harbor Laboratory Press*, Cold Spring Harbor, N.Y., 1989 (Chapters 5, 6)).

Saris, C.J., et al., "Blotting of RNA into RNA exchange paper allowing subsequence characterization by in situ translation in addition to blot hybridization," *Nucleic Acids Res.* 10:4831–4843 (1982).

Schena et al., "Quantitative Monitoring of Gene Expression Patterns with a Complementary DNA Microarray" *Science* 270:467–470 (1995).

Schena, M., et al., "Parallel human genome analysis: Microarray–based expression monitoring of 1000 genes," *Proc. Natl. Acad. Sci. USA* 91:10614–10619 (1994).

Schenborn and Meirendorf, "A novel transcription property of SP6 and 17 RNA polymerases: dependence on template structure", *Nucleic Acids Research* 13(17): 6223–6236 (1985).

Schwarz, K., "Improved yields of long PCR products using gene 32 protein," *Nucl. Acids Res.*, 18:1079 (1990).

Siegel et al., "A Novel DNA Helicase from Calf Thymus", *Journal of Biological Chemistry* 267(19): 13629–13635 (1992).

Skaliter and Lehman, "Rolling circle DNA replication in vitro by a complex of herpes simplex virus type 1–encoded enzymes", *Proc. Natl. Acad. Sci. USA* 91(22): 10665–10669 (1994).

Speicher et al., "Karyotyping human chromosomes by combinatorial multi–fluor Fish", *Nature Genetics* 12(4): 368–375 (1996).

Stimpson et al., "Real–time detection of DNA hybridization and melting on oligonucleotide arrays by using optical wave guides", *Proc. Natl. Acad. Sci. USA* 92(14): 6379–6383 (1995).

Strauss and Jacobowitz, "Quantitative measure of calretinin and β–actin mRNA in rat brain micropunches without prior isolation of RNA," *Mol. Brain Res.* 20:229–239 (1993).

Studier et al., "Use of T7 RNA Polymerase to Direct Expression of Cloned Genes", *Methods in Enzymology* 185: 60–89 (1990).

Syvänen et al., "Fast Qualification of nucleic acid hybrids by affinity–based hybrid collection", 14(12): 5037–5049 (1986).

Tabor and Richardson, "Selective inactivation of the exonuclease activity of bacteriophase T7 DNA polymerase by in vitro mutagenesis" *J. Biol. Chem.* 264:6447–6458 (1989).

Lawyer et al., "High–level Expression, Purification, and Enzymatic Characterization of Full–length *Thermus aquaticus* DNA Polymerase and a Truncated Form Deficient in 5'to 3'Exonuclease Activity", *PCR Methods Applications* 2(4): 275–287 (1993).

LeFrere et al., "Towards a new predictor of AIDS progression through the quantitation of HIV–1 DNA copies by PCR in HIV–infected individuals", *British Journal of Haematology* 82(2): 467–471 (1992).

Lesnick and Freier, "Relative Thermodynamic Stability of DNA, RNA, and DNA:RNA Hybrid Duplexes: Relationship with Base Composition and Structure", *Biochemistry* 34: 10807–10815 (1995)

Liu, D., et al., "Rolling circle DNA synthesis: Small circular oligonucleotides as efficient templates for DNA polymerases," *J. Am. Chem. Soc.* 118:1587–1594 (1996).

Lockhart, et al., "Expression monitoring by hybridization to high–density oligonucleotide arrays," *Nature Biotechnology* 14:1675–1680 (1996).

Lu et al., "High Concentration of Peripheral Blood Mononuclear Cells Harboring Infectious Virus Correlates with Rapid Progression of Human Immunodeficiency Virus Type 1–Related Diseases", *JID* 168(5): 1165–8116 (1993).

Lukyanov, C., et al., "Molecule by molecule PCR amplification of complex DNA mixtures for direct sequencing: an approach to in vitro cloning," *Nucleic Acids Research* 20:1691–1696 (1996).

Luo, J., et al., "Improving the fidelity of *Thermus thermophilus* DNA ligase," *Nucl. Acids Res.* 24:3071–3078 (1996).

McCray et al., "A new approach to time–resolved studies of ATP–requiring biological systems: Laser flash photolysis of caged ATP" *Proc. Natl. Acad. Sci. USA 77:7237–7241 (1980)*.

McGraw et al., "Sequence–dependant oligonucleotide–target duplex stabilities: rules from empirical studies with a set of twenty–mers" *Biotechniques* 8:674–678 (1990).

Marshall et al., "Detection of HCV RNA by the Asymmetric Gap Ligase Chain Reaction", *PCR Methods and Applications* 4: 80–84 (1994).

Maskos, U., et al., "Oligonucleotide hybridizations on glass supports: a novel linker for oligonucleotides synthesized in situ," *Nucleic Acids Research* 20:1679–1684 (1992).

Matsumoto et al., Primary structure of bacteriophage M2 DNA polymerase: conserved segments within protein–priming DNA polymerases and DNA polymerase I of *Escherichia coli, Gene* 84(2): 247–255 (1989).

Melton et al., "Efficient in vitro synthesis of biologically active RNA and RNA hybridization probes form plasmids containing a bacteriophage SP6 promoter", *Nucleic Acids Research* 12(18): 7035–7056 (1984).

Metzker et al., "Termination of DNA synthesis by novel 3'–modified–deoxyribonucleoside 5'–triphosphates" *Nucleic Acids Research* 22:4259–4267 (1994).

Mujumdar et al., "Cyanine dye labeling reagents containing isothiocyanate groups" *Cytometry* 10:11–19 (1989).

Narang et al., "Chemical Synthesis of Deoxyoligonucleotides by the Modified Triester Method", *Methods Enzymology* 65: 610–620 (1980).

Newton, CR, et al., "Analysis of any point mutation in DNA. The amplification refractory mutation refractory mutation system (ARMS)," *Nucl. Acids Res.* 17:2503–2516 (1989).

Nielsen et al., "Peptide nucleic acids (PNAs): Potential anti–sense and anti–gene agents", *Anti–Cancer Drug Design,* 8: 53–63 (1993).

Nielsen et al., "Peptide Nucleic Acid (PNA). A DNA Mimic with a Peptide Backbone", *Bioconjugate Chemistry,* 5: 3–7 (1994).

Nikiforov et al., "The Use of Phosphorothioate Primers and Exonuclease Hydrolysis for the Preparation of Single–stranded PCR Products and their Detection by Solid–phase Hybridization", *PCR Methods and Applications* 3: 285–291 (1994).

Nikiforov et al., "Genetic Bit Analysis: a solid phase method for typing single nucleotide polymorphisms", *Nucleic Acids Research* 22(20): 4167–4175 (1994).

Nilsson et al., "Padlock Probes: Circularizing Oligonucleotides for Localized DNA Detection", *Science* 265: 2085–2088 (1994).

Nilsson, M., et al., "U. Padlock probes reveal single–nucleotide differences, parent of origin and in situ distribution of centromeric sequences in human chromosome 13 and 21," *Nature Genet.* 16:252–255 (1997).

Ørum et al., "Single base pair mutation analysis by PNA directed PCR clamping", *Nucleic Acids Research* 21(23):5332–5336 (1993).

Tabor and Richardson, "Selective oxidation of the exonuclease domain of bacteriophage T7 DNA polymerase" *J. Biol. Chem.* 262:15330–15333 (1987).

Thomas, D.C., et al., "Cascade rolling circle amplification, a homogeneous fluorescence detection system for DNA diagnostics," *Clin. Chem.* 43:2219 Abs. 38 (1997).

Thorbjarnardottir et al., "Sequence of the DNA ligase–encoding gene from *Thermus scotoductus* and conserved motifs in DNA ligases", *Gene* 151(1&2): 177–180 (1995).

Tsurumi et al., "Functional Interaction between EpsteinBarr Virus DNA Polymerase Catalytic Subunit and Its Accessory Subunit In Vitro", *Journal of Virology* 67(12): 7648–7653 (1993).

Tyagi and Kramer, "Molecular beacons: probes that fluoresce upon hybridization" *Nature Biotechnology* 14:303–308 (1996).

Velculescu, L., et al., "Serial Analysis of Gene Expression," *Science* 270:484–487 (1995).

Vogelstein, B., et al., "Supercoiled loops and eucaryotic DNA replication," *Cell* 22:79–85 (1980).

Waggoner A., "Covalent labeling of proteins and nucleic acids with fluorophores" *Meth. Enzymology* 246:362–373 (1995).

Walker, G.T., et al., "Strand Displacement Amplification an Isothermal, in vitro DNA amplification technique," *Nucleic Acids Research* 20:1691–1696 (1992).

Walter and Strunk, "Strand displacement amplification as an in vitro model for rolling–circle replication: Deletion formation and evolution during serial transfer", Proc. *Natl. Acad Sci. USA* 91:7937–7941 (1994).

Wansink et al., "Fluorescent Labeling of Nascent RNA Reveals Transcription by RNA Polymerase II in Domains Scattered Throughout the Nucleus", *Journal of Cell Biology* 122(2):283–293 (1993).

Wiedmann et al., "Ligase Chain Reaction (LCR)—Overview and Applications", *PCR Methods and Applications* (Cold Spring Harbor Laboratory Press, Cold Spring Harbor Laboratory, NY, 1994) pp. S51–S64.

Winn–Deen et al., "Non–radioactive detection of Mycobacterium tuberculosis LCR products in a microtitre plate format", *Molecular and Cellular Probes* (England) 7(3): 179–186 (1993).

Young and Anderson, "Quantitative analysis of solution hybridisation", *Nucleic Acid* Hybridisation: A Practical Approach (IRL Press, 1985) pp. 47–71.

Yu, et al., "Cyanine dye dUTP analogs for enzymatic labeling of DNA probes", *Nucleic Acids Research* 22(15): 3226–3232 (1994).

Zehavi et al., "Light sensitive glycosides. I. 6–Nitroveratryl β–D–Glucopyranoside and 2–Nitrobenzyl β–D–Glucopyranoside" *J. Organic Chem.* 37:2281–2288 (1972).

Zhu and Ito, "Purification and characterization of PRD1 DNA polymerase", *Biochimica Biophysica Acta* 1219(2): 267–276 (1994).

Zijderveld and van der Vliet, "Helix–Destabilizing Properties of the Adenovirus DNA–Binding Protein", *Journal of Virology* 68(2): 1158–1164 (1994).

* cited by examiner-

OPEN CIRCLE PROBES WITH INTRAMOLECULAR STEM STRUCTURES

The present invention is in the field of nucleic acid amplification, and specifically in the area of reducing non-specific amplification in nucleic acid amplification reactions.

BACKGROUND OF THE INVENTION

Numerous nucleic acid amplification techniques have been devised, including strand displacement cascade amplification (SDCA)(referred to herein as exponential rolling circle amplification (ERCA)) and rolling circle amplification (RCA)(U.S. Pat. No. 5,854,033; PCT Application No. WO 97/19193; Lizardi et al., *Nature Genetics* 19(3):225–232 (1998)); multiple displacement amplification (MDA)(PCT Application WO 99/18241); strand displacement amplification (SDA)(Walker et al., Nucleic Acids Research 20:1691–1696 (1992), Walker et al., Proc. Natl. Acad. Sci. USA 89:392–396 (1992)); polymerase chain reaction (PCR) and other exponential amplification techniques involving thermal cycling, self-sustained sequence replication (3SR), nucleic acid sequence based amplification (NASBA), and amplification with Qβ replicase (Birkenmeyer and Mushahwar, *J. Virological Methods* 35:117–126 (1991); Landegren, *Trends Genetics* 9:199–202 (1993)); and various linear amplification techniques involving thermal cycling such as cycle sequencing (Craxton et al., *Methods Companion Methods in Enzymology* 3:20–26 (1991)).

Rolling Circle Amplification (RCA) driven by DNA polymerase can replicate circular oligonucleotide probes with either linear or geometric kinetics under isothermal conditions (Lizardi et al., *Nature Genet.* 19: 225–232 (1998); U.S. Pat. Nos. 5,854,033 and 6,143,495; PCT Application No. WO 97/19193). If a single primer is used, RCA generates in a few minutes a linear chain of hundreds or thousands of tandemly-linked DNA copies of a target that is covalently linked to that target. Generation of a linear amplification product permits both spatial resolution and accurate quantitation of a target. DNA generated by RCA can be labeled with fluorescent oligonucleotide tags that hybridize at multiple sites in the tandem DNA sequences. RCA can be used with fluorophore combinations designed for multiparametric color coding (PCT Application No. WO 97/19193), thereby markedly increasing the number of targets that can be analyzed simultaneously. RCA technologies can be used in solution, in situ and in microarrays. In solid phase formats, detection and quantitation can be achieved at the level of single molecules (Lizardi et al., 1998). Ligation-mediated Rolling Circle Amplification (LM-RCA) involves circularization of a probe molecule hybridized to a target sequence and subsequent rolling circle amplification of the circular probe (U.S. Pat. Nos. 5,854,033 and 6,143,495; PCT Application No. WO 97/19193).

Artifacts—that is, unwanted, unexpected, or non-specific nucleic acid molecules—have been observed in almost all nucleic acid amplification reactions. For example, Stump et al., *Nucleic Acids Research* 27:4642–4648 (1999), describes nucleic acid artifacts resulting from an illegitimate PCR process during cycle sequencing. In rolling circle amplification, uncircularized open circle probes could prime synthesis during amplification of circularized open circle probes. Other forms of artifacts can occur in other types of nucleic acid amplification techniques.

Therefore, it is an object of the present invention to provide a method of reducing, preventing, or eliminating artifacts in nucleic acid amplification reactions.

It is another object of the present invention to provide open circle probes and primers that, when used in a nucleic acid amplification reaction, can reduce, prevent, or eliminate artifacts in the nucleic acid amplification reaction.

It is another object of the present invention to provide kits for nucleic acid amplification that can reduce, prevent, or eliminate artifacts in the nucleic acid amplification reaction.

BRIEF SUMMARY OF THE INVENTION

Disclosed are compositions and methods for reducing or eliminating generation of unwanted, undesirable, or non-specific amplification products in nucleic acid amplification reactions. One form of composition is an open circle probe that can form an intramolecular stem structure, such as a hairpin structure, at one or both ends. Open circle probes are useful in rolling circle amplification techniques. The stem structure allows the open circle probe to be circularized when hybridized to a legitimate target sequence but results in inactivation of uncircularized open circle probes. This inactivation, which preferably involves stabilization of the stem structure, extension of the end of the open circle probe, or both, reduces or eliminates the ability of the open circle probe to prime nucleic acid synthesis or to serve as a template for rolling circle amplification.

In ligation-mediated rolling circle amplification, a linear DNA molecule, referred to as an open circle probe or padlock probe, hybridizes to a target sequence and is circularized. The circularized probe is then amplified via rolling circle replication of the circular probe. Uncircularized probe that remains in the reaction can hybridize to nucleic acid sequences in the reaction and cause amplification of undesirable, non-specific sequences. The disclosed compositions and method address this problem by reducing or eliminating the potential uncircularized open circle probes from priming nucleic acid synthesis. A basic form of the disclosed method involves use of the disclosed open circle probes in a rolling circle amplification reaction or assay.

The disclosed open circle probes can be inactivated in several ways. For example, where the 3' end of an open circle probe is involved in an intramolecular stem structure, the 3' end can be extended in a replication reaction using the open circle probe sequences as template. Stabilization of the stem structure results in a reduction or elimination of the ability of the open circle probe to prime nucleic acid synthesis because the 3' end is stably hybridized to sequences in the open circle probe under the conditions used for nucleic acid replication. The open circle probe can also be inactivated by formation of the intramolecular stem structure during the amplification reaction. As long as the end remains in the intramolecular stem structure, it is not available for priming nucleic acid synthesis. A preferred form of open circle probe includes a loop as part of the intramolecular stem structure. Hybridization of the loop to the target sequence disrupts the intramolecular stem structure while hybridization of the loop to a mismatched or non-target sequence will not. Thus, the sequence-discrimination ability of the open circle probe determines inactivation of the open circle probe. A hybridization nucleating loop can also be used in linear primers used for nucleic acid replication and amplification.

The disclosed method is useful for detection, quantitation, and/or location of any desired analyte, such as proteins and peptides. The disclosed method can be multiplexed to detect numerous different analytes simultaneously or used in a single assay. Thus, the disclosed method is useful for detecting, assessing, quantitating, profiling, and/or cataloging gene expression and the presence of nucleic acids and protein in biological samples. The disclosed method is also particularly useful for detecting and discriminating single nucleotide differences in nucleic acid sequences. Thus, the disclosed method is useful for extensive multiplexing of target sequences for sensitive and specific detection of the target sequences themselves or analytes to which the target sequences have been associated. The disclosed method is applicable to numerous areas including, but not limited to, analysis of proteins present in a sample (for example, proteomics analysis), disease detection, mutation detection, protein expression profiling, RNA expression profiling, gene discovery, gene mapping (molecular haplotyping), agricultural research, and virus detection.

Figure 1:
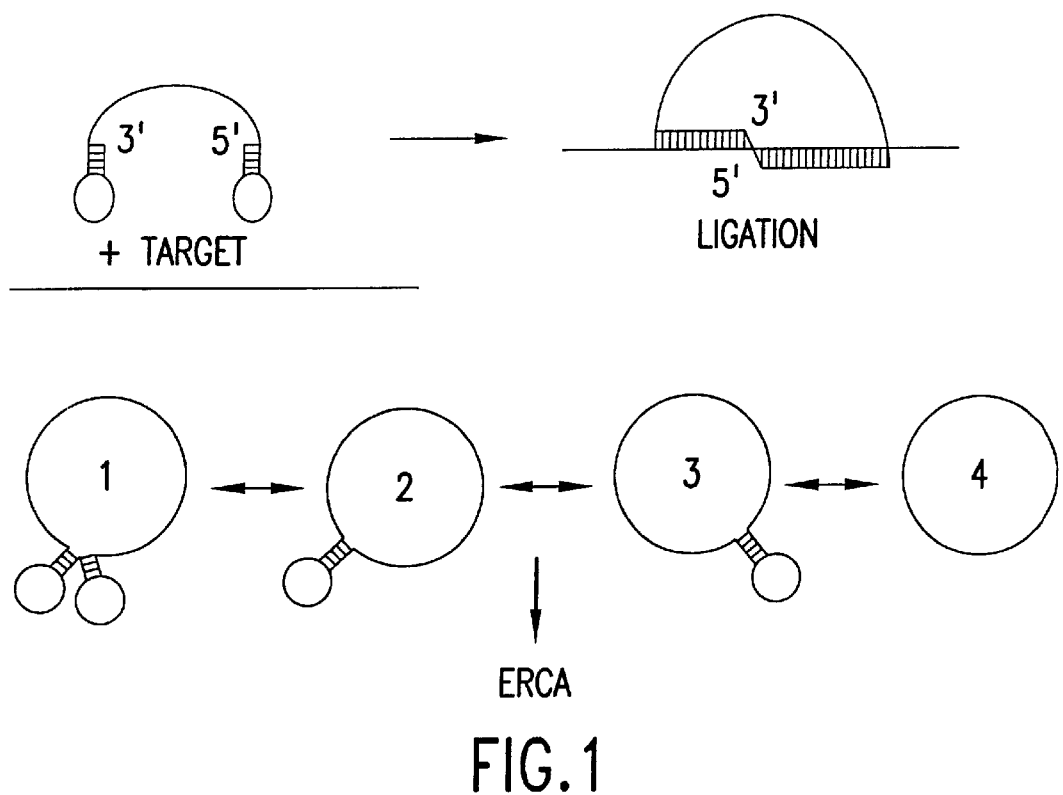
FIG. 1 is a diagram illustrating an open circle probe that forms hairpin intramolecular stem structures at both ends (top left). The open circle probe is shown hybridized to a target sequence and ligated (top right). Possible intramolecular structures formed by the ligated open circle probe are also shown (bottom).

Delta $Ct=(Ct$ minus ligase control$-Ct$ plus ligase).

DETAILED DESCRIPTION OF THE INVENTION

Disclosed are compositions and methods for reducing or eliminating generation of unwanted, undesirable, or non-specific amplification products in nucleic acid amplification reactions. One form of composition is an open circle probe that can form an intramolecular stem structure, such as a hairpin structure, at one or both ends. Open circle probes are useful in rolling circle amplification techniques. The stem structure allows the open circle probe to be circularized when hybridized to a legitimate target sequence but results in inactivation of uncircularized open circle probes. This inactivation, which preferably involves stabilization of the stem structure, extension of the end of the open circle probe, or both, reduces or eliminates the ability of the open circle probe to prime nucleic acid synthesis or to serve as a template for rolling circle amplification.

In ligation-mediated rolling circle amplification (LM-RCA), a linear DNA molecule, referred to as an open circle probe or padlock probe, hybridizes to a target sequence and is circularized. The circularized probe is then amplified via rolling circle replication of the circular probe. Uncircularized probe that remains in the reaction can hybridize to nucleic acid sequences in the reaction and cause amplification of undesirable, non-specific sequences. The disclosed compositions and method address this problem by reducing or eliminating the potential uncircularized open circle probes from priming nucleic acid synthesis.

The disclosed open circle probes can be inactivated in several ways. For example, where the 3' end of an open circle probe is involved in an intramolecular stem structure, the 3' end can be extended in a replication reaction using the open circle probe sequences as template (see FIG. 2B). The result is stabilization of the intramolecular stem structure and a change in the 3' end sequence. Stabilization of the stem structure results in a reduction or elimination of the ability of the open circle probe to prime nucleic acid synthesis because the 3' end is stably hybridized to sequences in the open circle probe under the conditions used for nucleic acid replication. Change in the sequence of the 3' end can reduce of the ability of the open circle probe to prime nucleic acid synthesis because the changed 3' sequences may not be as closely related to sequences involved in the amplification reaction or assay. Change in the sequence of the 3' end can reduce of the ability of the open circle probe to serve as a template for rolling circle amplification. For example, even if the open circle probe with extended 3' end were circularized, the rolling circle replication primer could be prevented from priming replication of such a circle if the primer complement sequence on the open circle probe were interrupted by the added sequences. This can be accomplished by, for example, designing the open circle probe to have the primer complement sequence include both 5' and 3' end sequences of the open circle probe.

The open circle probe can also be inactivated by formation of the intramolecular stem structure during the amplification reaction. As long as the end remains in the intramolecular stem structure, it is not available for priming nucleic acid synthesis. This form of inactivation is aided by design the intramolecular stem structure, or selecting amplification conditions, such that the intramolecular hybrid remains stable during rolling circle amplification.

One form of the disclosed open circle probes includes a loop as part of the intramolecular stem structure. It is preferred that the loop contain sequences complementary to the target sequence. This allows the loop to nucleate hybridization of the open probe to the target sequence. Preferred forms of the loop-containing probes are characterized by a sequence discrimination capability that is markedly better that the comparable linear probes due to the competition between the structural interferences between folding due to intramolecular stem formation and linear rigidity due to hybridization of the probe sequence to the target (Tyagi and Kramer, Nat Biotechnol 14(3):303–8 (1996); Bonnet et al., Proc Natl Acad Sci USA 96(11):6171–6 (1999)). Preferred open circle probes of this type will not hybridize to mismatched sequences under suitable conditions because duplex hybridization of probe to target does not effectively compete with intramolecular stem formation of the structured probe. This makes the end(s) of the open circle probe involved in an intramolecular stem structure unavailable for ligation to circularize the probe and leave the 3' end available for inactivating extension. The presence of target sequence causes the correctly matched open circle probe to unfold, allowing the ends to hybridize to the target sequence and be coupled (see FIG. 3). Where sequences in the loop nucleate hybridization of the open circle probe to a target sequence, loop hybridization to a non-target sequence is unlikely to lead to circularization of the open circle probe. This is because it is unlikely that a non-target sequence will include adjacent sequences to which both the loop and open circle probe end can hybridize (see FIG. 4).

A hybridization nucleating loop can also be used in linear primers used for nucleic acid replication and amplification. Such a primer forms an intramolecular stem structure, including a loop. Loop-containing primers of this type will not hybridize to mismatched sequences under suitable conditions because duplex hybridization of probe to target does not effectively compete with intramolecular stem formation of the structured probe. This makes the end of the primer involved in an intramolecular stem structure unavailable for priming. The legitimate primer complement sequence causes the correctly matched primer to unfold, allowing the end to hybridize to the primer complement sequence and prime synthesis. Where sequences in the loop nucleate hybridization of the primer, loop hybridization to an illegitimate sequence is unlikely to lead to priming. This is because it is unlikely that an illegitimate sequence will include adjacent sequences to which both the loop and the primer end can hybridize. Including proximity-sensitive labels used in molecular beacon probes in such primers allows hybridization and priming by the primers to be detected through activation of the label upon disruption of the intramolecular stem structure (Tyagi and Kramer, Nat Biotechnol 14(3):303–8 (1996); Bonnet et al., Proc Natl Acad Sci USA 96(11):6171–6 (1999)).

The disclosed method is useful for detection, quantitation, and/or location of any desired analyte. The disclosed method can be multiplexed to detect numerous different analytes simultaneously or used in a single assay. Thus, the disclosed method is useful for detecting, assessing, quantitating, profiling, and/or cataloging gene expression and the presence of protein in biological samples. The disclosed method is also particularly useful for detecting and discriminating single nucleotide differences in nucleic acid sequences. This specificity is possible due to the sensitivity of the intramolecular stem structure in loop-containing probes and primers to mismatches between the loop sequence and a prospective target sequence. Thus, the disclosed method is useful for extensive multiplexing of target sequences for sensitive and specific detection of the target sequences themselves or analytes to which the target sequences have been associated. The disclosed method is also useful for detecting, assessing, quantitating, and/or cataloging single nucleotide polymorphisms, and other sequence differences between nucleic acids, nucleic acid samples, and sources of nucleic acid samples.

The disclosed method is useful for detecting any desired sequence or other analyte, such as proteins and peptides. In particular, the disclosed method can be used to localize or amplify signal from any desired analyte. For example, the disclosed method can be used to assay tissue, transgenic cells, bacterial or yeast colonies, cellular material (for example, whole cells, proteins, DNA fibers, interphase nuclei, or metaphase chromosomes on slides, arrayed genomic DNA, RNA), and samples and extracts from any of biological source. Where target sequences are associated with an analyte, different target sequences, and thus different analytes, can be sensitively distinguished. Specificity of such detection is aided by sensitivity of a loop in an open circle probe to mismatches.

The disclosed method is applicable to numerous areas including, but not limited to, analysis of proteins present in a sample (for example, proteomics analysis), disease detection, mutation detection, protein expression profiling, RNA expression profiling, gene discovery, gene mapping (molecular haplotyping), agricultural research, and virus detection. Preferred uses include protein and peptide detection in situ in cells, on microarrays, protein expression profiling; mutation detection; detection of abnormal proteins or peptides (for example, overexpression of an oncogene protein or absence of expression of a tumor suppressor protein); expression in cancer cells; detection of viral proteins in cells; viral protein expression; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer. The disclosed method can also be used for detection of nucleic acids in situ in cells, on microarrays, on DNA fibers, and on genomic DNA arrays; detection of RNA in cells; RNA expression profiling; molecular haplotyping; mutation detection; detection of abnormal RNA (for example, overexpression of an oncogene or absence of expression of a tumor suppressor gene); expression in cancer cells; detection of viral genome in cells; viral RNA expression; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

Rolling Circle Amplification

The disclosed probes and primers are generally useful in rolling circle amplification (RCA) reactions. Rolling circle amplification is described in U.S. Pat. Nos. 5,854,033 and 6,143,495. Rolling circle amplification involves amplifying nucleic acid sequences based on the presence of a specific target sequence or analyte, such as a protein or peptide. The method is useful for detecting specific nucleic acids or analytes in a sample with high specificity and sensitivity. The method also has an inherently low level of background signal. Preferred embodiments of the method, referred to as ligation-mediated RCA (LM-RCA), consist of a DNA ligation operation, an amplification operation, and, optionally, a detection operation. The DNA ligation operation circularizes a specially designed nucleic acid probe molecule (referred to as an open circle probe). This step is dependent on hybridization of the probe to a target sequence and forms circular probe molecules in proportion to the amount of target sequence present in a sample. The amplification operation is rolling circle replication of the circularized probe. By coupling a nucleic acid tag to a specific binding molecule, such as an antibody, amplification of the nucleic acid tag can be used to detect analytes in a sample. This is preferred for detection of analytes where a target nucleic acid sequence is part of a reporter binding molecule, where an amplification target circle serves as an amplifiable tag on a reporter binding molecule, or where an amplification target circle is amplified using a rolling circle replication primer that is part of a reporter binding molecule. Optionally, an additional amplification operation can be performed on the DNA produced by rolling circle replication. Rolling circle amplification can also be performed independently of a ligation operation.

Following amplification, the amplified sequences can be detected and quantified using any of the conventional detection systems for nucleic acids such as detection of fluorescent labels, enzyme-linked detection systems, antibody-mediated label detection, and detection of radioactive labels. Major advantages of this method are that the ligation operation can be manipulated to obtain allelic discrimination and the amplification operation is isothermal. In multiplex assays, the primer oligonucleotide used for DNA replication can be the same for all probes, or subsets of probes can be used for different sets of amplified nucleic acids to be detected. Rolling circle amplification is especially suited to sensitive detection of multiple analytes, such as proteins and peptides, in a single assay, reaction, or assay system.

Rolling circle amplification has two features that provide simple and consistent amplification and detection of a target nucleic acid sequence. First, target sequences are amplified via a small diagnostic probe with an arbitrary primer binding sequence. This allows consistency in the priming and replication reactions, even between probes having very different target sequences. Second, amplification takes place not in cycles, but in a continuous, isothermal replication: rolling circle replication. This makes amplification less complicated and much more consistent in output.

The disclosed compositions can also be used in methods for of multiplex detection of molecules of interest involving rolling circle replication. The methods are useful for simultaneously detecting multiple specific nucleic acids in a sample with high specificity and sensitivity. The methods also have an inherently low level of background signal. A preferred form of such a method consists of an association operation, an amplification operation, and a detection operation. The method preferably also includes a ligation operation. The association operation involves association of one or more specially designed reporter binding molecules, either wholly or partly nucleic acid, to target molecules of interest. The reporter binding molecules can target any molecule of interest but preferably target proteins or peptides. This operation associates the reporter binding molecules to a target molecules present in a sample. The amplification operation is rolling circle replication of circular nucleic acid molecules, termed amplification target circles, that are either a part of, or hybridized to, the probe molecules. By coupling a nucleic acid tag to a specific binding molecule, such as an antibody, amplification of the nucleic acid tag can be used to detect analytes in a sample.

Following rolling circle replication, the amplified sequences can be detected using combinatorial multicolor coding probes (or other multiplex detection system) that allow separate and simultaneous detection of multiple different amplified target sequences representing multiple different target molecules. Major advantages of this method are that a large number of distinct target molecules can be detected simultaneously, and that differences in the amounts of the various target molecules in a sample can be accurately quantified. The target molecules can be analytes of any nature (such as proteins and peptides) by associating the target sequences to be amplified with the target molecules.

Materials

A. Open Circle Probes

Figure 2:
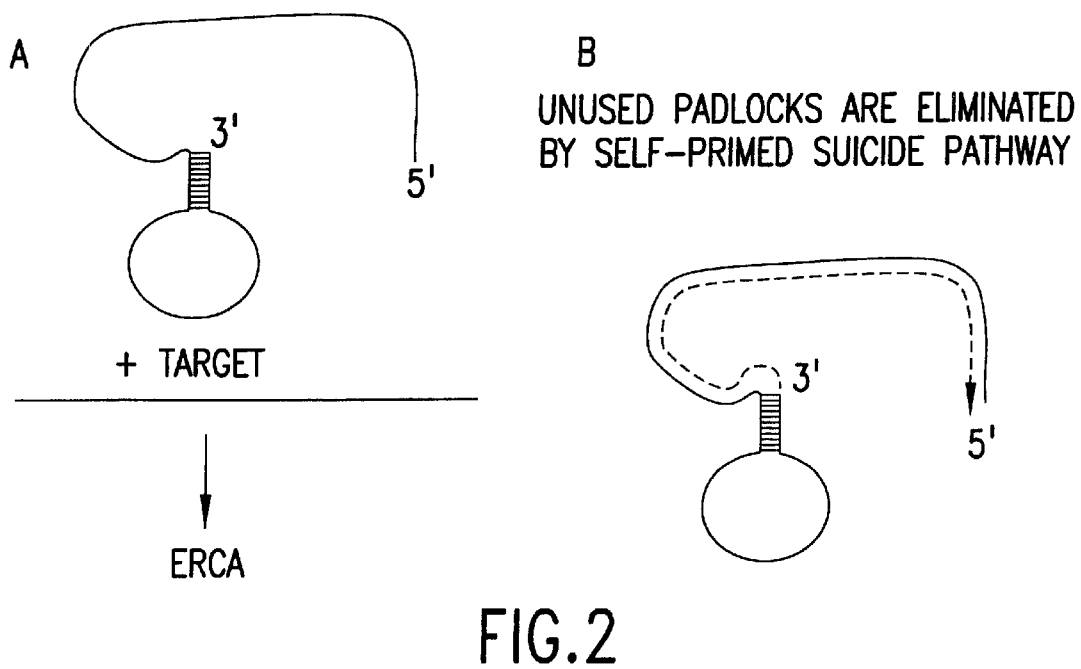
FIGS. 2A and 2B are diagrams illustrating an open circle probe that forms a stem and loop intramolecular stem structure. If the target sequence is present, the open circle probe will hybridize to the target sequence, be ligated, and serve as a template in rolling circle amplification (FIG. 2A). If the target sequence is not present, the intramolecular structure remains and the 3' end of the open circle probe is extended using the "other" strand as template (FIG. 2B).

An open circle probe (OCP) is a linear single-stranded DNA molecule, preferably containing between 50 to 1000 nucleotides, more preferably between about 60 to 150 nucleotides, and most preferably between about 70 to 100 nucleotides. The OCP has a 5' phosphate group and a 3' hydroxyl group. This allows the ends to be ligated (to each other or to other nucleic acid ends) using a ligase, coupled, or extended in a gap-filling operation. Preferred open circle probes for use in the disclosed method can form an intramolecular stem structure involving one or both of the OCP's ends. Such open circle probes are referred to herein as hairpin open circle probes. An intramolecular stem structure involving an end refers to a stem structure where the terminal nucleotides (that is, nucleotides at the end) of the OCP are hybridized to other nucleotides in the OCP (FIGS. 1 and 2).

The intramolecular stem structure can form a hairpin structure or a stem and loop structure. If both ends of an OCP are involved in an intramolecular stem structure, the two ends of the OCP can each form a separate intramolecular stem structure or can together form a single intramolecular stem structure. In the latter case the two ends would be hybridized together. It is preferred that the 3' end of the open circle probe form an intramolecular stem structure. The 5' end of the open circle probe can also form an intramolecular stem structure, either alone, or in the same open circle probe having an intramolecular stem structure at the 3' end. The intramolecular stem structure preferably forms under conditions suitable for nucleic acid replication, and in particular under conditions used for nucleic acid replication when the open circle probe is being used. For example, the intramolecular stem structure can be designed to form under conditions used for rolling circle replication. The formation of the intramolecular stem structure during replication allows the structure to reduce or prevent participation of uncircularized open circle probes in nucleic acid replication. In particular, the intramolecular stem structure prevents the open circle probe in which the structure forms from serving as a template for rolling circle replication, from priming nucleic acid replication, or both. This follows from the sequestration of the end of uncircularized open circle probe in the stem. The end of the open circle probe cannot hybridize to, and prime from, another sequence while sequestered in the intramolecular stem structure. It is also preferred that the intramolecular stem structure be more stable than hybrids between the open circle probe and mismatched sequences. In this way, the intramolecular stem structure will be thermodynamically favored over undesired primer hybridizations. Open circle probes that form intramolecular stem structures at the 3' end will have the 3' end extended during replication (using open circle probe sequences as template). This serves to stabilize the intramolecular stem structure in the uncircularized open circle probes, making them unavailable for priming.

Portions of the OCP have specific functions making the OCP useful for RCA and LM-RCA. These portions are referred to as the target probe portions, the primer complement portion, the spacer region, the detection tag portions, the secondary target sequence portions, the address tag portions, and the promoter portion. The target probe portions and the primer complement portion are required elements of an open circle probe. The primer complement portion is preferably part of the spacer region. Detection tag portions, secondary target sequence portions, and promoter portions are optional and, when present, are part of the spacer region. Address tag portions are optional and, when present, may be part of the spacer region. The primer complement portion, and the detection tag portions, the secondary target sequence portions, the address tag portions, and the promoter portion, if present, are preferably non-overlapping. However, various of these portions can be partially or completely overlapping if desired. Generally, an open circle probe is a single-stranded, linear DNA molecule comprising, from 5' end to 3' end, a 5' phosphate group, a right target probe portion, a spacer region, a left target probe portion, and a 3' hydroxyl group, with a primer complement portion present as part of the spacer region. Those segments of the spacer region that do not correspond to a specific portion of the OCP can be arbitrarily chosen sequences. It is preferred that OCPs do not have any sequences that are self-complementary. It is considered that this condition is met if there are no complementary regions greater than six nucleotides long without a mismatch or gap. It is also preferred that OCPs containing a promoter portion do not have any sequences that resemble a transcription terminator, such as a run of eight or more thymidine nucleotides.

The open circle probe, when ligated and replicated, gives rise to a long DNA molecule containing multiple repeats of sequences complementary to the open circle probe. This long DNA molecule is referred to herein as tandem sequences DNA (TS-DNA). TS-DNA contains sequences complementary to the target probe portions, the primer complement portion, the spacer region, and, if present on the open circle probe, the detection tag portions, the secondary target sequence portions, the address tag portions, and the promoter portion. These sequences in the TS-DNA are referred to as target sequences (which match the original target sequence), primer sequences (which match the sequence of the rolling circle replication primer), spacer sequences (complementary to the spacer region), detection tags, secondary target sequences, address tags, and promoter sequences.

1. Target Probe Portions

There are two target probe portions on each OCP, one at each end of the OCP. The target probe portions can each be any length that supports specific and stable hybridization between the target probes and the target sequence. For this purpose, a length of 10 to 35 nucleotides for each target probe portion is preferred, with target probe portions 15 to 25 nucleotides long being most preferred. The target probe portion at the 3' end of the OCP is referred to as the left target probe, and the target probe portion at the 5' end of the OCP is referred to as the right target probe. These target probe portions are also referred to herein as left and right target probes or left and right probes. The target probe portions are complementary to a target nucleic acid sequence.

Figure 3:
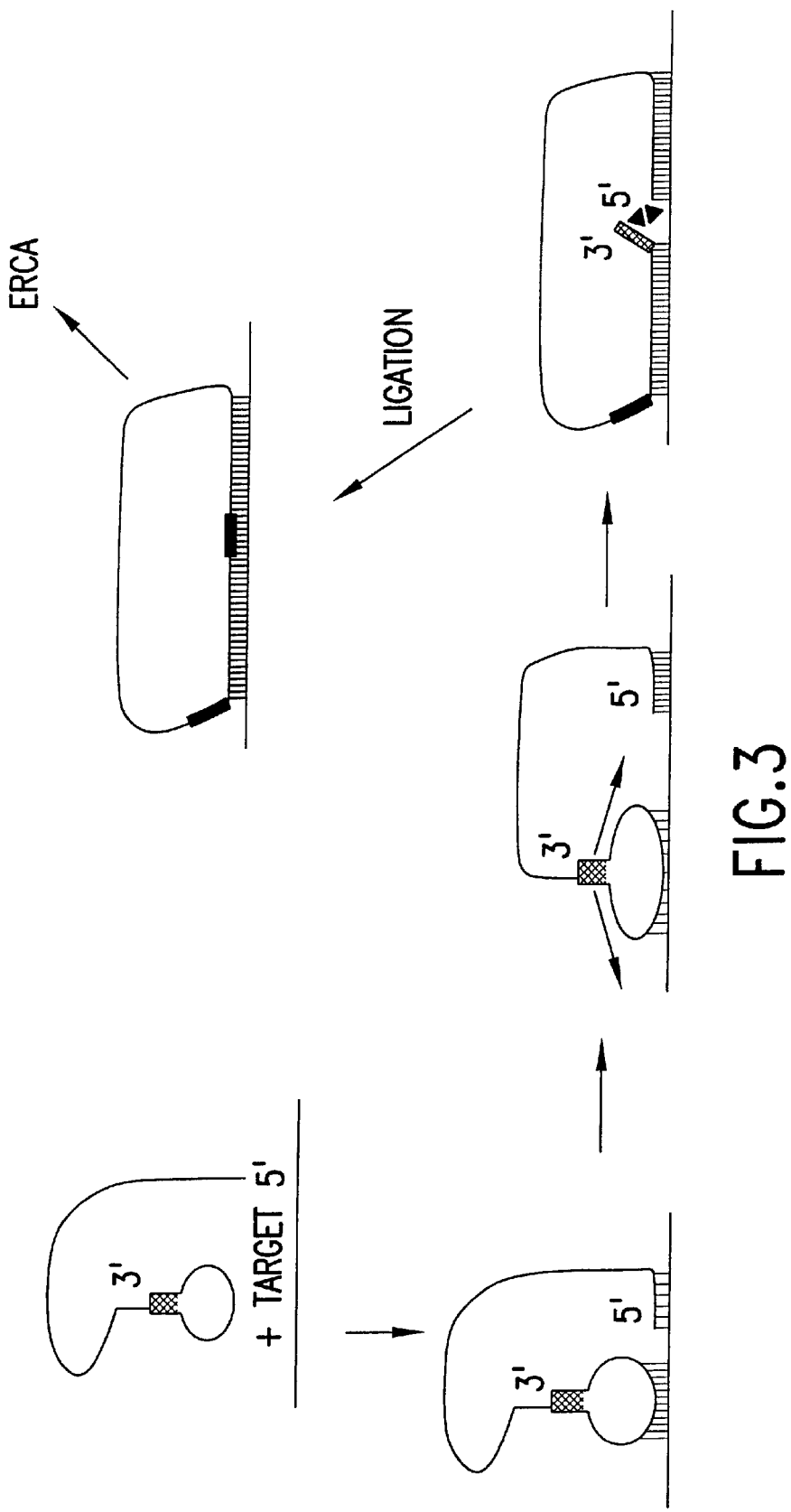
FIG. 3 is a diagram illustrating hybridization, ligation, and amplification of an open circle probe that forms a stem and loop intramolecular stem structure. Hybridization to the target sequence is nucleated by interaction between nucleotides in the loop of the open circle probe and nucleotides in the target sequence (left). This nucleation causes the intramolecular stem structure to be disrupted (middle bottom). The freed end can now hybridize to the target sequence, adjacent to the other end of the probe (right bottom). The open circle probe can then be ligated, thus circularizing the probe, followed by rolling circle amplification of the circularized probe (right top).
Figure 4:
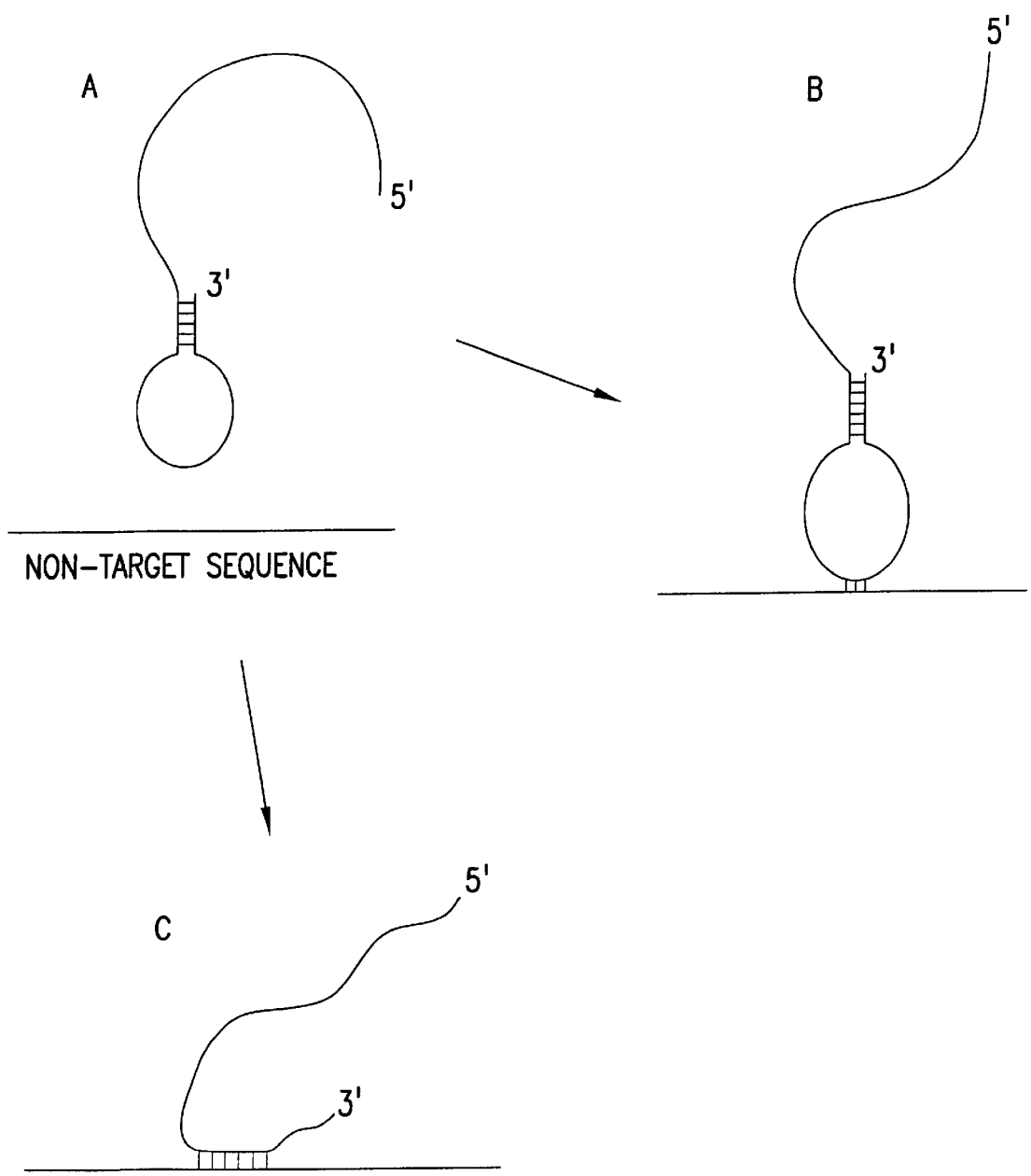
FIGS. 4A, 4B, and 4C are diagrams illustrating hybridization of an open circle probe that forms a stem and loop intramolecular stem structure to a non-target sequence. In most cases, hybridization of loop sequences to a non-target sequence will leave the intramolecular stem structure intact (FIG. 4B). The open circle probe will not be circularized. Even if hybridization of the loop to a non-target sequence were to disrupt the intramolecular stem structure, the non-target sequence is unlikely to have nucleotides complementary to end sequences of the open circle probe (FIG. 4C).

The target probe portions are complementary to the target sequence, such that upon hybridization the 5' end of the right target probe portion and the 3' end of the left target probe portion are base-paired to adjacent nucleotides in the target sequence, with the objective that they serve as a substrate for ligation.

Where the intramolecular stem structure of an open circle probe forms a stem and loop structure, it is preferred that a portion of one of the target probe portions of the open circle probe is in the loop of the stem and loop structure. This portion of the target probe portion in the loop can then hybridize to the target sequence of the open circle probe. Such an arrangement allows design of hairpin open circle probes where the stability of the intramolecular stem structure depends on the presence or absence of the specific target sequence. In particular, an open circle probe that forms a stem and loop structure with a portion of the target probe portion in the loop can be designed so that hybridization of the target probe portion in the loop to the target sequence disrupts the intramolecular stem structure (FIG. 2; Tyagi and Kramer, Nat Biotechnol 14(3):303–8 (1996); Bonnet et al., Proc Natl Acad Sci USA 96(11):6171–6 (1999)). In this way, the intramolecular stem structure remains intact in the absence of the target sequence and thus reduces or eliminates the ability of the open circle probe to prime nucleic acid replication (or to serve as a template for rolling circle replication). In the presence of the target sequence, disruption of the intramolecular stem structure allows the end of the open circle probe to hybridize to the target sequence. This hybrid between the target sequence and the end of the open circle probe allows the ends of the open circle probe to come into proximity on the target sequence which in turn allows ligation of the ends (FIG. 3). For this form of hairpin open circle probe, it is preferred that hybridization of the loop to a sequence other than the target sequence does not disrupt the intramolecular stem structure. Preferably, the hybrid between the target sequence and the target probe portion at the end of the open circle probe is more stable than the intramolecular stem structure. This helps stabilize hybridization of the open circle probe to the target sequence in competition with the intramolecular stem structure.

Discrimination of open circle probe hybridization also can be accomplished by hybridizing probe to target sequence under conditions that favor only exact sequence matches leaving other open circle probes unhybridized. The unhybridized open circle probes will retain or re-form the intramolecular hybrid and the end of the open circle probe involved in the intramolecular stem structure will be extended during replication.

In another form of open circle probe, the 5' end and the 3' end of the target probe portions may hybridize in such a way that they are separated by a gap space. In this case the 5' end and the 3' end of the OCP may only be ligated if one or more additional oligonucleotides, referred to as gap oligonucleotides, are used, or if the gap space is filled during the ligation operation. The gap oligonucleotides hybridize to the target sequence in the gap space to a form continuous probe/target hybrid. The gap space may be any length desired but is generally ten nucleotides or less. It is preferred that the gap space is between about three to ten nucleotides in length, with a gap space of four to eight nucleotides in length being most preferred. Alternatively, a gap space could be filled using a DNA polymerase during the ligation operation. When using such a gap-filling operation, a gap space of three to five nucleotides in length is most preferred. As another alternative, the gap space can be partially bridged by one or more gap oligonucleotides, with the remainder of the gap filled using DNA polymerase.

2. Primer Complement Portion

The primer complement portion is part of the spacer region of an open circle probe. The primer complement portion is complementary to the rolling circle replication primer (RCRP). Each OCP preferably has a single primer complement portion. This allows rolling circle replication to initiate at a single site on ligated OCPs. The primer complement portion and the cognate primer can have any desired sequence so long as they are complementary to each other. The sequence of the primer complement portion is referred to as the primer complement sequence. In general, the sequence of the primer complement can be chosen such that it is not significantly similar to any other portion of the OCP. The primer complement portion can be any length that supports specific and stable hybridization between the primer complement portion and the primer. For this purpose, a length of 10 to 35 nucleotides is preferred, with a primer complement portion 16 to 20 nucleotides long being most preferred. The primer complement portion can be located anywhere within the spacer region of an OCP. It is preferred that the primer complement portion is adjacent to the right target probe, with the right target probe portion and the primer complement portion preferably separated by three to ten nucleotides, and most preferably separated by six nucleotides. This location prevents the generation of any other spacer sequences, such as detection tags and secondary target sequences, from unligated open circle probes during DNA replication.

3. Detection Tag Portions

Detection tag portions are part of the spacer region of an open circle probe. Detection tag portions have sequences matching the sequence of the complementary portion of detection probes. These detection tag portions, when amplified during rolling circle replication, result in TS-DNA having detection tag sequences that are complementary to the complementary portion of detection probes. If present, there may be one, two, three, or more than three detection tag portions on an OCP. It is preferred that an OCP have two, three or four detection tag portions. Most preferably, an OCP will have three detection tag portions. Generally, it is preferred that an OCP have 60 detection tag portions or less. There is no fundamental limit to the number of detection tag portions that can be present on an OCP except the size of the OCP. When there are multiple detection tag portions, they may have the same sequence or they may have different sequences, with each different sequence complementary to a different detection probe. It is preferred that an OCP contain detection tag portions that have the same sequence such that they are all complementary to a single detection probe. For some multiplex detection methods, it is preferable that OCPs contain up to six detection tag portions and that the detection tag portions have different sequences such that each of the detection tag portions is complementary to a different detection probe. The detection tag portions can each be any length that supports specific and stable hybridization between the detection tags and the detection probe. For this purpose, a length of 10 to 35 nucleotides is preferred, with a detection tag portion 15 to 20 nucleotides long being most preferred.

4. Secondary Target Sequence Portions

Secondary target sequence portions are part of the spacer region of an open circle probe. Secondary target sequence portions have sequences matching the sequence of target probes of a secondary open circle probe. These secondary target sequence portions, when amplified during rolling circle replication, result in TS-DNA having secondary target sequences that are complementary to target probes of a secondary open circle probe. If present, there may be one, two, or more than two secondary target sequence portions on an OCP. It is preferred that an OCP have one or two secondary target sequence portions. Most preferably, an OCP will have one secondary target sequence portion. Generally, it is preferred that an OCP have 50 secondary target sequence portions or less. There is no fundamental limit to the number of secondary target sequence portions that can be present on an OCP except the size of the OCP. When there are multiple secondary target sequence portions, they may have the same sequence or they may have different sequences, with each different sequence complementary to a different secondary OCP. It is preferred that an OCP contain secondary target sequence portions that have the same sequence such that they are all complementary to a single target probe portion of a secondary OCP. The secondary target sequence portions can each be any length that supports specific and stable hybridization between the secondary target sequence and the target sequence probes of its cognate OCP. For this purpose, a length of 20 to 70 nucleotides is preferred, with a secondary target sequence portion 30 to 40 nucleotides long being most preferred. As used herein, a secondary open circle probe is an open circle probe where the target probe portions match or are complementary to secondary target sequences in another open circle probe or an amplification target circle. It is contemplated that a secondary open circle probe can itself contain secondary target sequences that match or are complementary to the target probe portions of another secondary open circle probe. Secondary open circle probes related to each other in this manner are referred to herein as nested open circle probes.

5. Address Tag Portion

The address tag portion is part of either the target probe portions or the spacer region of an open circle probe. The address tag portion has a sequence matching the sequence of the complementary portion of an address probe. This address tag portion, when amplified during rolling circle replication, results in TS-DNA having address tag sequences that are complementary to the complementary portion of address probes. If present, there may be one, or more than one, address tag portions on an OCP. It is preferred that an OCP have one or two address tag portions. Most preferably, an OCP will have one address tag portion. Generally, it is preferred that an OCP have 50 address tag portions or less. There is no fundamental limit to the number of address tag portions that can be present on an OCP except the size of the OCP. When there are multiple address tag portions, they may have the same sequence or they may have different sequences, with each different sequence complementary to a different address probe. It is preferred that an OCP contain address tag portions that have the same sequence such that they are all complementary to a single address probe. Preferably, the address tag portion overlaps all or a portion of the target probe portions, and all of any intervening gap space. Most preferably, the address tag portion overlaps all or a portion of both the left and right target probe portions. The address tag portion can be any length that supports specific and stable hybridization between the address tag and the address probe. For this purpose, a length between 10 and 35 nucleotides long is preferred, with an address tag portion 15 to 20 nucleotides long being most preferred.

6. Promoter Portion

The promoter portion corresponds to the sequence of an RNA polymerase promoter. A promoter portion can be included in an open circle probe so that transcripts can be generated from TS-DNA. The sequence of any promoter may be used, but simple promoters for RNA polymerases without complex requirements are preferred. It is also preferred that the promoter is not recognized by any RNA polymerase that may be present in the sample containing the target nucleic acid sequence. Preferably, the promoter portion corresponds to the sequence of a T7 or SP6 RNA polymerase promoter. The T7 and SP6 RNA polymerases are highly specific for particular promoter sequences. Other promoter sequences specific for RNA polymerases with this characteristic would also be preferred. Because promoter sequences are generally recognized by specific RNA polymerases, the cognate polymerase for the promoter portion of the OCP should be used for transcriptional amplification. Numerous promoter sequences are known and any promoter specific for a suitable RNA polymerase can be used. The promoter portion can be located anywhere within the spacer region of an OCP and can be in either orientation. Preferably, the promoter portion is immediately adjacent to the left target probe and is oriented to promote transcription toward the 3' end of the open circle probe. This orientation results in transcripts that are complementary to TS-DNA, allowing independent detection of TS-DNA and the transcripts, and prevents transcription from interfering with rolling circle replication.

B. Gap Oligonucleotides

Gap oligonucleotides are oligonucleotides that are complementary to all or a part of that portion of a target sequence which covers a gap space between the ends of a hybridized open circle probe. Gap oligonucleotides have a phosphate group at their 5' ends and a hydroxyl group at their 3' ends. This facilitates ligation of gap oligonucleotides to open circle probes, or to other gap oligonucleotides. The gap space between the ends of a hybridized open circle probe can be filled with a single gap oligonucleotide, or it can be filled with multiple gap oligonucleotides. For example, two 3 nucleotide gap oligonucleotides can be used to fill a six nucleotide gap space, or a three nucleotide gap oligonucleotide and a four nucleotide gap oligonucleotide can be used to fill a seven nucleotide gap space. Gap oligonucleotides are particularly useful for distinguishing between closely related target sequences. For example, multiple gap oligonucleotides can be used to amplify different allelic variants of a target sequence. By placing the region of the target sequence in which the variation occurs in the gap space formed by an open circle probe, a single open circle probe can be used to amplify each of the individual variants by using an appropriate set of gap oligonucleotides.

C. Amplification Target Circles

An amplification target circle (ATC) is a circular single-stranded DNA molecule, preferably containing between 40 to 1000 nucleotides, more preferably between about 50 to 150 nucleotides, and most preferably between about 50 to 100 nucleotides. Portions of ATCs have specific functions making the ATC useful for rolling circle amplification (RCA). These portions are referred to as the primer complement portion, the detection tag portions, the secondary target sequence portions, the address tag portions, and the promoter portion. The primer complement portion is a required element of an amplification target circle. Detection tag portions, secondary target sequence portions, address tag portions, and promoter portions are optional. The primer complement portion, and the detection tag portions, the secondary target sequence portions, the address tag portions, and the promoter portion, if present, are preferably non-overlapping. However, various of these portions can be partially or completely overlapping if desired. Generally, an amplification target circle is a single-stranded, circular DNA molecule comprising a primer complement portion. Those segments of the ATC that do not correspond to a specific portion of the ATC can be arbitrarily chosen sequences. It is preferred that ATCs do not have any sequences that are self-complementary. It is considered that this condition is met if there are no complementary regions greater than six nucleotides long without a mismatch or gap. It is also preferred that ATCs containing a promoter portion do not have any sequences that resemble a transcription terminator, such as a run of eight or more thymidine nucleotides. Ligated open circle probes are a type of ATC, and as used herein the term amplification target circle includes ligated open circle probes. An ATC can be used in the same manner as described herein for OCPs that have been ligated.

An amplification target circle, when replicated, gives rise to a long DNA molecule containing multiple repeats of sequences complementary to the amplification target circle. This long DNA molecule is referred to herein as tandem sequences DNA (TS-DNA). TS-DNA contains sequences complementary to the primer complement portion and, if present on the amplification target circle, the detection tag portions, the secondary target sequence portions, the address tag portions, and the promoter portion. These sequences in the TS-DNA are referred to as primer sequences (which match the sequence of the rolling circle replication primer), spacer sequences (complementary to the spacer region), detection tags, secondary target sequences, address tags, and promoter sequences. Amplification target circles are useful as tags for specific binding molecules.

D. Rolling Circle Replication Primer

A rolling circle replication primer (RCRP) is an oligonucleotide having sequence complementary to the primer complement portion of an OCP or ATC. This sequence is referred to as the complementary portion of the RCRP. The complementary portion of a RCRP and the cognate primer complement portion can have any desired sequence so long as they are complementary to each other. In general, the sequence of the RCRP can be chosen such that it is not significantly complementary to any other portion of the OCP or ATC. The complementary portion of a rolling circle replication primer can be any length that supports specific and stable hybridization between the primer and the primer complement portion. Generally this is 10 to 35 nucleotides long, but is preferably 16 to 20 nucleotides long.

Preferred rolling circle replication primers for use in the disclosed method can form an intramolecular stem structure involving one or both of the RCRP's ends. Such rolling circle replication primers are referred to herein as hairpin rolling circle replication primers. An intramolecular stem structure involving an end refers to a stem structure where the terminal nucleotides (that is, nucleotides at the end) of the RCRP are hybridized to other nucleotides in the RCRP.

The intramolecular stem structure can form a hairpin structure or a stem and loop structure. If both ends of an RCRP are involved in an intramolecular stem structure, the two ends of the RCRP can each form a separate intramolecular stem structure or can together form a single intramolecular stem structure. In the latter case the two ends would be hybridized together. It is preferred that the 3' end of the rolling circle replication primer form an intramolecular stem structure. The 5' end of the rolling circle replication primer can also form an intramolecular stem structure, either alone, or in the rolling circle replication primer having an intramolecular stem structure at the 3' end. The intramolecular stem structure preferably involves both ends of the primer and has a blunt end. Also preferred is a short 3' unpaired overhang. The intramolecular stem structure preferably forms under conditions suitable for nucleic acid replication, and in particular under conditions used for nucleic acid replication when the rolling circle replication primer is being used. For example, the intramolecular stem structure can be designed to form under conditions used for rolling circle replication. The formation of the intramolecular stem structure during replication allows the structure to reduce or prevent priming by rolling circle replication primers at unintended sequences. In particular, the intramolecular stem structure prevents the rolling circle replication primer in which the structure forms from priming rolling circle replication, from priming nucleic acid replication, or both, at sites other than primer complement sequences (that is, the specific sequences complementary to the complementary portion of the rolling circle replication primer). This follows from the sequestration of the end of rolling circle replication primer in the stem. The end of the rolling circle replication primer cannot hybridize to, and prime from, another sequence while sequestered in the intramolecular stem structure. For this purpose, it is preferred that the intramolecular stem structure be less stable that the hybrid between the primer complement sequence and the complementary portion of the rolling circle replication primer (or, put another way, the hybrid between the primer complement sequence and the complementary portion of the rolling circle replication primer should be more stable than the intramolecular stem structure). It is also preferred that the intramolecular stem structure be more stable than hybrids between the rolling circle replication primer and mismatched sequences. In this way, the intramolecular stem structure will be thermodynamically favored over undesired primer hybridizations. Although rolling circle replication primers that form intramolecular stem structures at the 3' end leaving the 5' end unpaired and overhanging can be used, this is not preferred. In such a case, the 3' end could be extended during replication (using rolling circle replication primer sequences as template), thus inactivating the primers.

Where the intramolecular stem structure of a rolling circle replication primer forms a stem and loop structure, it is preferred that a portion of the complementary portion of the rolling circle replication primer be in the loop of the stem and loop structure. This portion of the complementary portion in the loop can then hybridize to the primer complement sequence of the open circle probe. Such an arrangement allows design of hairpin rolling circle replication primers where the stability of the intramolecular stem structure depends on the presence or absence of the specific primer complement sequence. In particular, a rolling circle replication primer that forms a stem and loop structure with a portion of the complementary portion in the loop can be designed so that hybridization of the complementary portion in the loop to the primer complement sequence disrupts the intramolecular stem structure (Tyagi and Kramer, Nat Biotechnol 14(3):303–8 (1996); Bonnet et al., Proc Natl Acad Sci USA 96(11):6171–6 (1999)). In this way, the intramolecular stem structure remains intact in the absence of the primer complement sequence and thus reduces or eliminates the ability of the rolling circle replication primer to prime nucleic acid replication. In the presence of the primer complement sequence, disruption of the intramolecular stem structure allows the end of the rolling circle replication primer to hybridize to the primer complement sequence. This hybrid between the primer complement sequence and the end of the rolling circle replication primer allows the priming of nucleic acid replication by the primer. For this form of hairpin rolling circle replication primer, it is preferred that hybridization of the loop to a sequence other than the primer complement sequence does not disrupt the intramolecular stem structure. Preferably, the hybrid between the primer complement sequence and the end of the rolling circle replication primer is more stable than the intramolecular stem structure. This helps stabilize hybridization of the rolling circle replication primer to the primer complement sequence in competition with the intramolecular stem structure.

Discrimination of rolling circle replication primer hybridization also can be accomplished by hybridizing primer to primer complement portions of OCPs or ATCs under conditions that favor only exact sequence matches leaving other rolling circle replication primer unhybridized. The unhybridized rolling circle replication primers will retain or re-form the intramolecular hybrid.

It is preferred that rolling circle replication primers also contain additional sequence at the 5' end of the RCRP that is not complementary to any part of the OCP or ATC. This sequence is referred to as the non-complementary portion of the RCRP. The non-complementary portion of the RCRP, if present, serves to facilitate strand displacement during DNA replication. The non-complementary portion of a RCRP may be any length, but is generally 1 to 100 nucleotides long, and preferably 4 to 8 nucleotides long. The rolling circle replication primer may also include modified nucleotides to make it resistant to exonuclease digestion. For example, the primer can have three or four phosphorothioate linkages between nucleotides at the 5' end of the primer. Such nuclease resistant primers allow selective degradation of excess unligated OCP and gap oligonucleotides that might otherwise interfere with hybridization of detection probes, address probes, and secondary OCPs to the amplified nucleic acid. A rolling circle replication primer can be used as the tertiary DNA strand displacement primer in strand displacement cascade amplification.

Rolling circle replication primers may also include modified nucleotides to make them resistant to exonuclease digestion. For example, the primer can have three or four phosphorothioate linkages between nucleotides at the 5' end of the primer. Such nuclease resistant primers allow selective degradation of excess unligated OCP and gap oligonucleotides that might otherwise interfere with hybridization of detection probes, address probes, and secondary OCPs to the amplified nucleic acid.

E. DNA Strand Displacement Primers

Primers used for secondary DNA strand displacement are referred to herein as DNA strand displacement primers. One form of DNA strand displacement primer, referred to herein as a secondary DNA strand displacement primer, is an oligonucleotide having sequence matching part of the sequence of an OCP or ATC. This sequence is referred to as the matching portion of the secondary DNA strand displacement primer. This matching portion of a secondary DNA strand displacement primer is complementary to sequences in TS-DNA. The matching portion of a secondary DNA strand displacement primer may be complementary to any sequence in TS-DNA. However, it is preferred that it not be complementary TS-DNA sequence matching either the rolling circle replication primer or a tertiary DNA strand displacement primer, if one is being used. This prevents hybridization of the primers to each other. The matching portion of a secondary DNA strand displacement primer may be complementary to all or a portion of the target sequence. In this case, it is preferred that the 3' end nucleotides of the secondary DNA strand displacement primer are complementary to the gap sequence in the target sequence. It is most preferred that nucleotide at the 3' end of the secondary DNA strand displacement primer falls complementary to the last nucleotide in the gap sequence of the target sequence, that is, the 5' nucleotide in the gap sequence of the target sequence. The matching portion of a secondary DNA strand displacement primer can be any length that supports specific and stable hybridization between the primer and its complement. Generally this is 12 to 35 nucleotides long, but is preferably 18 to 25 nucleotides long.

Preferred secondary DNA strand displacement primers for use in the disclosed method can form an intramolecular stem structure involving one or both of the secondary DNA strand displacement primer's ends. Such secondary DNA strand displacement primers are referred to herein as hairpin secondary DNA strand displacement primers. An intramolecular stem structure involving an end refers to a stem structure where the terminal nucleotides (that is, nucleotides at the end) of the secondary DNA strand displacement primer are hybridized to other nucleotides in the secondary DNA strand displacement primer.

The intramolecular stem structure can form a hairpin structure or a stem and loop structure. If both ends of a secondary DNA strand displacement primer are involved in an intramolecular stem structure, the two ends of the secondary DNA strand displacement primer can each form a separate intramolecular stem structure or can together form a single intramolecular stem structure. In the latter case the two ends would be hybridized together. It is preferred that the 3' end of the secondary DNA strand displacement primer form an intramolecular stem structure. The 5' end of the secondary DNA strand displacement primer can also form an intramolecular stem structure, either alone, or in the secondary DNA strand displacement primer having an intramolecular stem structure at the 3' end. The intramolecular stem structure preferably involves both ends of the primer and has a blunt end. Also preferred is a short 3' unpaired overhang. The intramolecular stem structure preferably forms under conditions suitable for nucleic acid replication, and in particular under conditions used for nucleic acid replication when the secondary DNA strand displacement primer is being used.

For example, the intramolecular stem structure can be designed to form under conditions used for rolling circle replication. The formation of the intramolecular stem structure during replication allows the structure to reduce or prevent priming by secondary DNA strand displacement primers at unintended sequences. In particular, the intramolecular stem structure prevents the secondary DNA strand displacement primer in which the structure forms from priming nucleic acid replication at sites other than primer complement sequences (that is, the specific sequences complementary to the complementary portion of the secondary DNA strand displacement primer) in TS-DNA. This follows from the sequestration of the end of secondary DNA strand displacement primer in the stem. The end of the rolling circle replication primer cannot hybridize to, and prime from, another sequence while sequestered in the intramolecular stem structure. For this purpose, it is preferred that the intramolecular stem structure be less stable that the hybrid between the primer complement sequence and the complementary portion of the secondary DNA strand displacement primer (or, put another way, the hybrid between the primer complement sequence and the matching portion of the secondary DNA strand displacement primer should be more stable than the intramolecular stem structure). It is also preferred that the intramolecular stem structure be more stable than hybrids between the secondary DNA strand displacement primer and mismatched sequences. In this way, the intramolecular stem structure will be thermodynamically favored over undesired primer hybridizations. Although secondary DNA strand displacement primers that form intramolecular stem structures at the 3' end leaving the 5' end unpaired and overhanging can be used, they are not preferred. In such a case, the 3' end could be extended during replication (using secondary DNA strand displacement primer sequences as template), thus inactivating the primers.

Where the intramolecular stem structure of a secondary DNA strand displacement primer forms a stem and loop structure, it is preferred that a portion of the complementary portion of the secondary DNA strand displacement primer be in the loop of the stem and loop structure. This portion of the complementary portion in the loop can then hybridize to the primer complement sequence in TS-DNA. Such an arrangement allows design of hairpin secondary DNA strand displacement primers where the stability of the intramolecular stem structure depends on the presence or absence of the specific primer complement sequence. In particular, a secondary DNA strand displacement primer that forms a stem and loop structure with a portion of the matching portion in the loop can be designed so that hybridization of the matching portion in the loop to the primer complement sequence disrupts the intramolecular stem structure (Tyagi and Kramer, Nat Biotechnol 14(3):303–8 (1996); Bonnet et al., Proc Natl Acad Sci USA 96(11):6171–6 (1999)). In this way, the intramolecular stem structure remains intact in the absence of the primer complement sequence and thus reduces or eliminates the ability of the secondary DNA strand displacement primer to prime nucleic acid replication. In the presence of the primer complement sequence, disruption of the intramolecular stem structure allows the end of the secondary DNA strand displacement primer to hybridize to the primer complement sequence. This hybrid between the primer complement sequence and the end of the secondary DNA strand displacement primer allows the priming of nucleic acid replication by the primer. For this form of hairpin secondary DNA strand displacement primer, it is preferred that hybridization of the loop to a sequence other than the primer complement sequence does not disrupt the intramolecular stem structure. Preferably, the hybrid between the primer complement sequence and the end of the secondary DNA strand displacement primer is more stable than the intramolecular stem structure. This helps stabilize hybridization of the secondary DNA strand displacement primer to the primer complement sequence in competition with the intramolecular stem structure.

Discrimination of secondary DNA strand displacement primer hybridization also can be accomplished by hybridizing primer to primer complement portions in TS-DNA under conditions that favor only exact sequence matches leaving other secondary DNA strand displacement primer unhybridized. The unhybridized secondary DNA strand displacement primers will retain or re-form the intramolecular hybrid.

It is preferred that secondary DNA strand displacement primers also contain additional sequence at their 5' end that does not match any part of the OCP or ATC. This sequence is referred to as the non-matching portion of the secondary DNA strand displacement primer. The non-matching portion of the secondary DNA strand displacement primer, if present, serves to facilitate strand displacement during DNA replication. The non-matching portion of a secondary DNA strand displacement primer may be any length, but is generally 1 to 100 nucleotides long, and preferably 4 to 8 nucleotides long.

Another form of DNA strand displacement primer, referred to herein as a tertiary DNA strand displacement primer, is an oligonucleotide having sequence complementary to part of the sequence of an OCP or ATC. This sequence is referred to as the complementary portion of the tertiary DNA strand displacement primer. This complementary portion of the tertiary DNA strand displacement primer matches sequences in TS-DNA. The complementary portion of a tertiary DNA strand displacement primer may be complementary to any sequence in the OCP or ATC. However, it is preferred that it not be complementary OCP or ATC sequence matching the secondary DNA strand displacement primer. This prevents hybridization of the primers to each other. Preferably, the complementary portion of the tertiary DNA strand displacement primer has sequence complementary to a portion of the spacer portion of an OCP. The complementary portion of a tertiary DNA strand displacement primer can be any length that supports specific and stable hybridization between the primer and its complement. Generally this is 12 to 35 nucleotides long, but is preferably 18 to 25 nucleotides long.

Preferred tertiary DNA strand displacement primers for use in the disclosed method can form an intramolecular stem structure involving one or both of the tertiary DNA strand displacement primer's ends. Such tertiary DNA strand displacement primers are referred to herein as hairpin tertiary DNA strand displacement primers. An intramolecular stem structure involving an end refers to a stem structure where the terminal nucleotides (that is, nucleotides at the end) of the tertiary DNA strand displacement primer are hybridized to other nucleotides in the tertiary DNA strand displacement primer.

The intramolecular stem structure can form a hairpin structure or a stem and loop structure. If both ends of a tertiary DNA strand displacement primer are involved in an intramolecular stem structure, the two ends of the tertiary DNA strand displacement primer can each form a separate intramolecular stem structure or can together form a single intramolecular stem structure. In the latter case the two ends would be hybridized together. It is preferred that the 3' end of the tertiary DNA strand displacement primer form an intramolecular stem structure. The 5' end of the tertiary DNA strand displacement primer can also form an intramolecular stem structure, either alone, or in the tertiary DNA strand displacement primer having an intramolecular stem structure at the 3' end. The intramolecular stem structure preferably forms under conditions suitable for nucleic acid replication, and in particular under conditions used for nucleic acid replication when the tertiary DNA strand displacement primer is being used. For example, the intramolecular stem structure can be designed to form under conditions used for rolling circle replication. The formation of the intramolecular stem structure during replication allows the structure to reduce or prevent priming by tertiary DNA strand displacement primers at unintended sequences. In particular, the intramolecular stem structure prevents the tertiary DNA strand displacement primer in which the structure forms from priming nucleic acid replication at sites other than primer complement sequences (that is, the specific sequences complementary to the complementary portion of the tertiary DNA strand displacement primer) in TS-DNA. This follows from the sequestration of the end of tertiary DNA strand displacement primer in the stem. The end of the rolling circle replication primer cannot hybridize to, and prime from, another sequence while sequestered in the intramolecular stem structure. For this purpose, it is preferred that the intramolecular stem structure be less stable that the hybrid between the primer complement sequence and the complementary portion of the tertiary DNA strand displacement primer (or, put another way, the hybrid between the primer complement sequence and the complementary portion of the tertiary DNA strand displacement primer should be more stable than the intramolecular stem structure). It is also preferred that the intramolecular stem structure be more stable than hybrids between the tertiary DNA strand displacement primer and mismatched sequences. In this way, the intramolecular stem structure will be thermodynamically favored over undesired primer hybridizations. Tertiary DNA strand displacement primers that form intramolecular stem structures at the 3' end will have the 3' end extended during replication (using tertiary DNA strand displacement primer sequences as template). This serves to stabilize the intramolecular stem structure in the tertiary DNA strand displacement primers, making them unavailable for priming.

Where the intramolecular stem structure of a tertiary DNA strand displacement primer forms a stem and loop structure, it is preferred that a portion of the complementary portion of the tertiary DNA strand displacement primer be in the loop of the stem and loop structure. This portion of the complementary portion in the loop can then hybridize to the primer complement sequence in TS-DNA. Such an arrangement allows design of hairpin tertiary DNA strand displacement primers where the stability of the intramolecular stem structure depends on the presence or absence of the specific primer complement sequence. In particular, a tertiary DNA strand displacement primer that forms a stem and loop structure with a portion of the complementary portion in the loop can be designed so that hybridization of the complementary portion in the loop to the primer complement sequence disrupts the intramolecular stem structure (Tyagi and Kramer, Nat Biotechnol 14(3):303–8 (1996); Bonnet et al., Proc Natl Acad Sci USA 96(11):6171–6 (1999)). In this way, the intramolecular stem structure remains intact in the absence of the primer complement sequence and thus reduces or eliminates the ability of the tertiary DNA strand displacement primer to prime nucleic acid replication. In the presence of the primer complement sequence, disruption of the intramolecular stem structure allows the end of the tertiary DNA strand displacement primer to hybridize to the primer complement sequence. This hybrid between the primer complement sequence and the end of the tertiary DNA strand displacement primer allows the priming of nucleic acid replication by the primer. For this form of hairpin tertiary DNA strand displacement primer, it is preferred that hybridization of the loop to a sequence other than the primer complement sequence does not disrupt the intramolecular stem structure. Preferably, the hybrid between the primer complement sequence and the end of the tertiary DNA strand displacement primer is more stable than the intramolecular stem structure. This helps stabilize hybridization of the tertiary DNA strand displacement primer to the primer complement sequence in competition with the intramolecular stem structure.

Discrimination of tertiary DNA strand displacement primer hybridization also can be accomplished by hybridizing primer to primer complement portions in TS-DNA under conditions that favor only exact sequence matches leaving other tertiary DNA strand displacement primer unhybridized. The unhybridized tertiary DNA strand displacement primers will retain or re-form the intramolecular hybrid and the end of the tertiary DNA strand displacement primer involved in the intramolecular stem structure will be extended during replication.

It is preferred that tertiary DNA strand displacement primers also contain additional sequence at their 5' end that is not complementary to any part of the OCP or ATC. This sequence is referred to as the non-complementary portion of the tertiary DNA strand displacement primer. The non-complementary portion of the tertiary DNA strand displacement primer, if present, serves to facilitate strand displacement during DNA replication. The non-complementary portion of a tertiary DNA strand displacement primer may be any length, but is generally 1 to 100 nucleotides long, and preferably 4 to 8 nucleotides long. A rolling circle replication primer is a preferred form of tertiary DNA strand displacement primer.

DNA strand displacement primers may also include modified nucleotides to make them resistant to exonuclease digestion. For example, the primer can have three or four phosphorothioate linkages between nucleotides at the 5' end of the primer. Such nuclease resistant primers allow selective degradation of excess unligated OCP and gap oligonucleotides that might otherwise interfere with hybridization of detection probes, address probes, and secondary OCPs to the amplified nucleic acid. DNA strand displacement primers can be used for secondary DNA strand displacement and strand displacement cascade amplification, both described below and in U.S. Pat. No. 6,143,495.

F. Reporter Binding Agents

A reporter binding agent is a specific binding molecule coupled or tethered to a nucleic acid such as an oligonucleotide. The specific binding molecule is referred to as the affinity portion of the reporter binding agent and the nucleic acid is referred to as the oligonucleotide portion of the reporter binding agent. As used herein, a specific binding molecule is a molecule that interacts specifically with a particular molecule or moiety (that is, an analyte). The molecule or moiety that interacts specifically with a specific binding molecule is referred to herein as a target molecule. The target molecules can be any analyte. It is to be understood that the term target molecule refers to both separate molecules and to portions of molecules, such as an epitope of a protein, that interacts specifically with a specific binding molecule. Antibodies, either member of a receptor/ligand pair, and other molecules with specific binding affinities are examples of specific binding molecules, useful as the affinity portion of a reporter binding molecule. A reporter binding molecule with an affinity portion which is an antibody is referred to herein as a reporter antibody. The oligonucleotide portion can be a nucleic acid molecule or a combination of nucleic acid molecules. The oligonucleotide portion is preferably an oligonucleotide or an amplification target circle.

By tethering an amplification target circle or coupling a target sequence to a specific binding molecule, binding of a specific binding molecule to its specific target can be detected by amplifying the ATC or target sequence with rolling circle amplification. This amplification allows sensitive detection of a very small number of bound specific binding molecules. A reporter binding molecule that interacts specifically with a particular target molecule is said to be specific for that target molecule. For example, a reporter binding molecule with an affinity portion which is an antibody that binds to a particular antigen is said to be specific for that antigen. The antigen is the target molecule. Reporter binding agents are also referred to herein as reporter binding molecules. FIGS. 25, 26, 27, 28, and 29 of U.S. Pat. No. 6,143,495 illustrate examples of several preferred types of reporter binding molecules and their use. FIG. 29 of U.S. Pat. No. 6,143,495 illustrates a reporter binding molecule using an antibody as the affinity portion.

Preferred target molecules are proteins and peptides. Use of reporter binding agents that target proteins and peptides allows sensitive signal amplification using rolling circle amplification for the detection of proteins and peptides. The ability to multiplex rolling circle amplification detection allows multiplex detection of the proteins and peptides (or any other target molecule). Thus, the disclosed method can be used for multi-protein analysis such as proteomics analysis. Such multi-protein analysis can be accomplished, for example, by using reporter binding agents targeted to different proteins, with the oligonucleotide portion of each reporter binding agent coded to allow separate amplification and detection of each different reporter binding agent.

In one embodiment, the oligonucleotide portion of a reporter binding agent includes a sequence, referred to as a target sequence, that serves as a target sequence for an OCP. The sequence of the target sequence can be arbitrarily chosen. In a multiplex assay using multiple reporter binding agents, it is preferred that the target sequence for each reporter binding agent be substantially different to limit the possibility of non-specific target detection. Alternatively, it may be desirable in some multiplex assays, to use target sequences with related sequences. By using different, unique gap oligonucleotides to fill different gap spaces, such assays can use one or a few OCPs to amplify and detect a larger number of target sequences. The oligonucleotide portion can be coupled to the affinity portion by any of several established coupling reactions. For example, Hendrickson et al., *Nucleic Acids Res.*, 23(3):522–529 (1995) describes a suitable method for coupling oligonucleotides to antibodies.

A preferred form of target sequence in a reporter binding agent is an oligonucleotide having both ends coupled to the specific binding molecule so as to form a loop. In this way, when the OCP hybridizes to the target and is circularized, the OCP will remain topologically locked to the reporter binding agent during rolling circle replication of the circularized OCP. This improves the localization of the resulting amplified signal to the location where the reporter binding agent is bound (that is, at the location of the target molecule).

A special form of reporter binding molecule, referred to herein as a reporter binding probe, has an oligonucleotide or oligonucleotide derivative as the specific binding molecule. Reporter binding probes are designed for and used to detect specific nucleic acid sequences. Thus, the target molecule for reporter binding probes are nucleic acid sequences. The target molecule for a reporter binding probe can be a nucleotide sequence within a larger nucleic acid molecule. It is to be understood that the term reporter binding molecule encompasses reporter binding probes. The specific binding molecule of a reporter binding probe can be any length that supports specific and stable hybridization between the reporter binding probe and the target molecule. For this purpose, a length of 10 to 40 nucleotides is preferred, with a specific binding molecule of a reporter binding probe 16 to 25 nucleotides long being most preferred. It is preferred that the specific binding molecule of a reporter binding probe is peptide nucleic acid. As described above, peptide nucleic acid forms a stable hybrid with DNA. This allows a reporter binding probe with a peptide nucleic acid specific binding molecule to remain firmly adhered to the target sequence during subsequent amplification and detection operations. This useful effect can also be obtained with reporter binding probes with oligonucleotide specific binding molecules by making use of the triple helix chemical bonding technology described by Gasparro et al., *Nucleic Acids Res.* 1994 22(14):2845–2852 (1994). Briefly, the affinity portion of a reporter binding probe is designed to form a triple helix when hybridized to a target sequence. This is accomplished generally as known, preferably by selecting either a primarily homopurine or primarily homopyrimidine target sequence. The matching oligonucleotide sequence which constitutes the affinity portion of the reporter binding probe will be complementary to the selected target sequence and thus be primarily homopyrimidine or primarily homopurine, respectively. The reporter binding probe (corresponding to the triple helix probe described by Gasparro et al.) contains a chemically linked psoralen derivative. Upon hybridization of the reporter binding probe to a target sequence, a triple helix forms. By exposing the triple helix to low wavelength ultraviolet radiation, the psoralen derivative mediates crosslinking of the probe to the target sequence. FIGS. 25, 26, 27, and 28 of U.S. Pat. No. 6,143,495 illustrate examples of reporter binding molecules that are reporter binding probes.

The specific binding molecule in a reporter binding probe can also be a bipartite DNA molecule, such as ligatable DNA probes adapted from those described by Landegren et al., *Science* 241:1077–1080 (1988). When using such a probe, the affinity portion of the probe is assembled by target-mediated ligation of two oligonucleotide portions which hybridize to adjacent regions of a target nucleic acid. Thus, the components used to form the affinity portion of such reporter binding probes are a truncated reporter binding probe (with a truncated affinity portion which hybridizes to part of the target sequence) and a ligation probe which hybridizes to an adjacent part of the target sequence such that it can be ligated to the truncated reporter binding probe. The ligation probe can also be separated from (that is, not adjacent to) the truncated reporter binding probe when both are hybridized to the target sequence. The resulting space between them can then be filled by a second ligation probe or by gap-filling synthesis. For use in the disclosed methods, it is preferred that the truncated affinity portion be long enough to allow target-mediated ligation but short enough to, in the absence of ligation to the ligation probe, prevent stable hybridization of the truncated reporter binding probe to the target sequence during the subsequent amplification operation. For this purpose, a specific step designed to eliminate hybrids between the target sequence and unligated truncated reporter binding probes can be used following the ligation operation.

In another embodiment, the oligonucleotide portion of a reporter binding agent includes a sequence, referred to as a rolling circle replication primer sequence, that serves as a rolling circle replication primer for an ATC. This allows rolling circle replication of an added ATC where the resulting TS-DNA is coupled to the reporter binding agent. Because of this, the TS-DNA will be effectively immobilized at the site of the target molecule. Preferably, the immobilized TS-DNA can then be collapsed in situ prior to detection. The sequence of the rolling circle replication primer sequence can be arbitrarily chosen. The rolling circle replication sequence can be designed to form and intramolecular stem structure as described for rolling circle replication primers above.

In a multiplex assay using multiple reporter binding agents, it is preferred that the rolling circle replication primer sequence for each reporter binding agent be substantially different to limit the possibility of non-specific target detection. Alternatively, it may be desirable in some multiplex assays, to use rolling circle replication primer sequences with related sequences. Such assays can use one or a few ATCs to detect a larger number of target molecules. When the oligonucleotide portion of a reporter binding agent is used as a rolling circle replication primer, the oligonucleotide portion can be any length that supports specific and stable hybridization between the oligonucleotide portion and the primer complement portion of an amplification target circle. Generally this is 10 to 35 nucleotides long, but is preferably 16 to 20 nucleotides long. FIGS. 25, 26, 27, 28, and 29 of U.S. Pat. No. 6,143,495 illustrate examples of reporter binding molecules in which the oligonucleotide portion is a rolling circle replication primer.

In another embodiment, the oligonucleotide portion of a reporter binding agent can include an amplification target circle which serves as a template for rolling circle replication. In a multiplex assay using multiple reporter binding agents, it is preferred that address tag portions and detection tag portions of the ATC comprising the oligonucleotide portion of each reporter binding agent be substantially different to unique detection of each reporter binding agent. It is desirable, however, to use the same primer complement portion in all of the ATCs used in a multiplex assay. The ATC is tethered to the specific binding molecule by looping the ATC around a tether loop. This allows the ATC to rotate freely during rolling circle replication while remaining coupled to the affinity portion. The tether loop can be any material that can form a loop and be coupled to a specific binding molecule. Linear polymers are a preferred material for tether loops.

A preferred method of producing a reporter binding agent with a tethered ATC is to form the tether loop by ligating the ends of oligonucleotides coupled to a specific binding molecule around an ATC. Oligonucleotides can be coupled to specific binding molecules using known techniques. For example, Hendrickson et al. (1995), describes a suitable method for coupling oligonucleotides to antibodies. This method is generally useful for coupling oligonucleotides to any protein. To allow ligation, oligonucleotides comprising the two halves of the tether loop should be coupled to the specific binding molecule in opposite orientations such that the free end of one is the 5' end and the free end of the other is the 3' end. Ligation of the ends of the tether oligonucleotides can be mediated by hybridization of the ends of the tether oligonucleotides to adjacent sequences in the ATC to be tethered. In this way, the ends of the tether oligonucleotides are analogous to the target probe portions of an open circle probe, with the ATC containing the target sequence. Similar techniques can be used to form tether loops containing a target sequence.

Another preferred method of producing a reporter binding agent with a tethered ATC is to ligate an open circle probe while hybridized to an oligonucleotide tether loop on a specific binding molecule. In this method, both ends of a single tether oligonucleotide are coupled to a specific binding molecule. This can be accomplished using known coupling techniques as described above. Ligation of an open circle probe hybridized to a tether loop is analogous to the ligation operation of LM-RCA. In this case, the target sequence is part of an oligonucleotide with both ends coupled to a specific binding molecule. This same ligation technique can be used to circularize open circle probes on target sequences that are part of reporter binding agents. This topologically locks the open circle probe to the reporter binding agent (and thus, to the target molecule to which the reporter binding agent binds).

The ends of tether loops can be coupled to any specific binding molecule with functional groups that can be derivatized with suitable activating groups. When the specific binding molecule is a protein, or a molecule with similar functional groups, coupling of tether ends can be accomplished using known methods of protein attachment. Many such methods are described in *Protein immobilization: fundamentals and applications* Richard F. Taylor, ed. (M. Dekker, New York, 1991).

Antibodies useful as the affinity portion of reporter binding agents, can be obtained commercially or produced using well established methods. For example, Johnstone and Thorpe, on pages 30–85, describe general methods useful for producing both polyclonal and monoclonal antibodies. The entire book describes many general techniques and principles for the use of antibodies in assay systems.

G. Detection Labels

To aid in detection and quantitation of nucleic acids amplified using RCA and RCT, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid or antibody probes are known to those of skill in the art. Examples of detection labels suitable for use in RCA and RCT are radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for combinatorial multicolor coding are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 rim), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are preferred form of detection label since they can be directly incorporated into the products of RCA and RCT during synthesis. Examples of detection labels that can be incorporated into amplified DNA or RNA include nucleotide analogs such as BrdUrd (Hoy and Schimke, *Mutation Research* 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.,* 22:3226–3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringer Mannheim). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo[3.3.1.1$^{3,7}$]decane]-4-yl)phenyl phosphate; Tropix, Inc.).

A preferred detection label for use in detection of amplified RNA is acridinium-ester-labeled DNA probe (GenProbe, Inc., as described by Arnold et al., *Clinical Chemistry* 35:1588–1594 (1989)). An acridinium-ester-labeled detection probe permits the detection of amplified RNA without washing because unhybridized probe can be destroyed with alkali (Arnold et al. (1989)).

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. Such methods can be used directly in the disclosed method of amplification and detection. As used herein, detection molecules are molecules that interact with amplified nucleic acid and to which one or more detection labels are coupled.

H. Detection Probes

Detection probes are labeled oligonucleotides having sequence complementary to detection tags on TS-DNA or transcripts of TS-DNA. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized (Tyagi and Kramer, *Nature Biotechnology* 14:303–308 (1996)). The use of such probes eliminates the need for removal of unhybridized probes prior to label detection because the unhybridized detection probes will not produce a signal. This is especially useful in multiplex assays.

A preferred form of detection probe, referred to herein as a collapsing detection probe, contains two separate complementary portions. This allows each detection probe to hybridize to two detection tags in TS-DNA. In this way, the detection probe forms a bridge between different parts of the TS-DNA. The combined action of numerous collapsing detection probes hybridizing to TS-DNA will be to form a collapsed network of cross-linked TS-DNA. Collapsed TS-DNA occupies a much smaller volume than free, extended TS-DNA, and includes whatever detection label present on the detection probe. This result is a compact and discrete detectable signal for each TS-DNA. Collapsing TS-DNA is useful both for in situ hybridization applications and for multiplex detection because it allows detectable signals to be spatially separate even when closely packed. Collapsing TS-DNA is especially preferred for use with combinatorial multicolor coding.

TS-DNA collapse can also be accomplished through the use of ligand/ligand binding pairs (such as biotin and avidin) or hapten/antibody pairs. As described in U.S. Pat. No. 6,143,495 (Example 6), a nucleotide analog, BUDR, can be incorporated into TS-DNA during rolling circle replication. When biotinylated antibodies specific for BUDR and avidin are added, a cross-linked network of TS-DNA forms, bridged by avidin-biotin-antibody conjugates, and the TS-DNA collapses into a compact structure. Collapsing detection probes and biotin-mediated collapse can also be used together to collapse TS-DNA.

I. Address Probes

An address probe is an oligonucleotide having a sequence complementary to address tags on TS-DNA or transcripts of TS-DNA. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. Preferably, the complementary portion of an address probe is complementary to all or a portion of the target probe portions of an OCP. Most preferably, the complementary portion of an address probe is complementary to a portion of either or both of the left and right target probe portions of an OCP and all or a part of any gap oligonucleotides or gap sequence created in a gap-filling operation (see FIG. 6 of U.S. Pat. No. 6,143, 495). Address probe can contain a single complementary portion or multiple complementary portions. Preferably, address probes are coupled, either directly or via a spacer molecule, to a solid-state support. Such a combination of address probe and solid-state support are a preferred form of solid-state detector.

J. Oligonucleotide Synthesis

Open circle probes, gap oligonucleotides, rolling circle replication primers, detection probes, address probes, amplification target circles, DNA strand displacement primers, and any other oligonucleotides can be synthesized using established oligonucleotide synthesis methods. Methods to produce or synthesize oligonucleotides are well known. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323–356 (1984), (phosphotriester and phosphite-triester methods), and Narang et al., *Methods Enzymol.*, 65:610–620 (1980), (phosphotriester method). Protein nucleic acid molecules can be made using known methods such as those described by Nielsen et al., *Bioconjug. Chem.* 5:3–7 (1994).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990).

K. Solid-State Detectors

Solid-state detectors are solid-state substrates or supports to which address probes or detection molecules have been coupled. A preferred form of solid-state detector is an array detector. An array detector is a solid-state detector to which multiple different address probes or detection molecules have been coupled in an array, grid, or other organized pattern.

Solid-state substrates for use in solid-state detectors can include any solid material to which oligonucleotides can be coupled. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a microtiter dish.

Address probes immobilized on a solid-state substrate allow capture of the products of RCA and RCT on a solid-state detector. Such capture provides a convenient means of washing away reaction components that might interfere with subsequent detection steps. By attaching different address probes to different regions of a solid-state detector, different RCA or RCT products can be captured at different, and therefore diagnostic, locations on the solid-state detector. For example, in a microtiter plate multiplex assay, address probes specific for up to 96 different TS-DNAs (each amplified via a different target sequence) can be immobilized on a microtiter plate, each in a different well. Capture and detection will occur only in those wells corresponding to TS-DNAs for which the corresponding target sequences were present in a sample.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022–5026 (1994), and Khrapko et al., *Mol Biol* (*Mosk*) (*USSR*) 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

Some solid-state detectors useful in RCA and RCT assays have detection antibodies attached to a solid-state substrate. Such antibodies can be specific for a molecule of interest. Captured molecules of interest can then be detected by binding of a second, reporter antibody, followed by RCA or RCT. Such a use of antibodies in a solid-state detector allows RCA assays to be developed for the detection of any molecule for which antibodies can be generated. Methods for immobilizing antibodies to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the solid-state substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

L. Solid-State Samples

Solid-state samples are solid-state substrates or supports to which target molecules or target sequences have been coupled or adhered. Target molecules or target sequences are preferably delivered in a target sample or assay sample. A preferred form of solid-state sample is an array sample. An array sample is a solid-state sample to which multiple different target samples or assay samples have been coupled or adhered in an array, grid, or other organized pattern.

Solid-state substrates for use in solid-state samples can include any solid material to which target molecules or target sequences can be coupled or adhered. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, slides, fibers, woven fibers, shaped polymers, particles and microparticles. Preferred forms for a solid-state substrate are microtiter dishes and glass slides.

Target molecules and target sequences immobilized on a solid-state substrate allow formation of target-specific TS-DNA localized on the solid-state substrate. Such localization provides a convenient means of washing away reaction components that might interfere with subsequent detection steps, and a convenient way of assaying multiple different samples simultaneously. Diagnostic TS-DNA can be independently formed at each site where a different sample is adhered. For immobilization of target sequences or other oligonucleotide molecules to form a solid-state sample, the methods described above for can be used. Where the target molecule is a protein or peptide, the protein or peptide can be immobilized on a solid-state substrate generally as described above for the immobilization of antibodies. Proteins and peptides within target samples are preferred targets of detection on solid-state substrates. Such an arrangement is a preferred platform for proteomics analysis using the disclosed materials and method.

A preferred form of solid-state substrate is a glass slide to which up to 256 separate target or assay samples have been adhered as an array of small dots. Each dot is preferably from 0.1 to 2.5 mm in diameter, and most preferably around 2.5 mm in diameter. Such microarrays can be fabricated, for example, using the method described by Schena et al., *Science* 270:487–470 (1995). Briefly, microarrays can be fabricated on poly-L-lysine-coated microscope slides (Sigma) with an arraying machine fitted with one printing tip. The tip is loaded with 1 $\mu$l of a DNA sample (0.5 mg/ml) from, for example, 96-well microtiter plates and deposited ~0.005 $\mu$l per slide on multiple slides at the desired spacing. The printed slides can then be rehydrated for 2 hours in a humid chamber, snap-dried at 100° C. for 1 minute, rinsed in 0.1% SDS, and treated with 0.05% succinic anhydride prepared in buffer consisting of 50% 1-methyl-2-pyrrolidinone and 50% boric acid. The DNA on the slides can then be denatured in, for example, distilled water for 2 minutes at 90° C. immediately before use. Microarray solid-state samples can scanned with, for example, a laser fluorescent scanner with a computer-controlled XY stage and a microscope objective. A mixed gas, multiline laser allows sequential excitation of multiple fluorophores.

M. DNA Ligases

Any DNA ligase is suitable for use in the disclosed amplification method. Preferred ligases are those that preferentially form phosphodiester bonds at nicks in double-stranded DNA. That is, ligases that fail to ligate the free ends of single-stranded DNA at a significant rate are preferred. Thermostable ligases are especially preferred. Many suitable ligases are known, such as T4 DNA ligase (Davis et al., *Advanced Bacterial Genetics—A Manual for Genetic Engineering* (Cold Spring Harbor Laboratory, Cold Spring Harbor, N.Y., 1980)), *E. coli* DNA ligase (Panasnko et al., *J. Biol. Chem.* 253:4590–4592 (1978)), AMPLIGASE® (Kalin et al., *Mutat. Res.*, 283(2):119–123 (1992); Winn-Deen et al., *Mol Cell Probes* (England) 7(3):179–186 (1993)), Taq DNA ligase (Barany, *Proc. Natl. Acad. Sci. USA* 88:189–193 (1991), *Thermus thermophilus* DNA ligase (Abbott Laboratories), *Thermus scotoductus* DNA ligase and *Rhodothermus marinus* DNA ligase (Thorbjamardottir et al., *Gene* 151:177–180 (1995)). T4 DNA ligase is preferred for ligations involving RNA target sequences due to its ability to ligate DNA ends involved in DNA:RNA hybrids (Hsuih et al., *Quantitative detection of HCV RNA using novel ligation-dependent polymerase chain reaction,* American Association for the Study of Liver Diseases (Chicago, Ill., Nov. 3–7, 1995)).

The frequency of non-target-directed ligation catalyzed by a ligase can be determined as follows. LM-RCA is performed with an open circle probe and a gap oligonucleotide in the presence of a target sequence. Non-targeted-directed ligation products can then be detected by using an address probe specific for the open circle probe ligated without the gap oligonucleotide to capture TS-DNA from such ligated probes. Target directed ligation products can be detected by using an address probe specific for the open circle probe ligated with the gap oligonucleotide. By using a solid-state detector with regions containing each of these address probes, both target directed and non-target directed ligation products can be detected and quantitated. The ratio of target-directed and non-target-directed TS-DNA produced provides a measure of the specificity of the ligation operation. Target-directed ligation can also be assessed as discussed in Barany (1991).

N. DNA Polymerases

DNA polymerases useful in the rolling circle replication step of the disclosed method must perform rolling circle replication of primed single-stranded circles. Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the ligated OCP. A 5' to 3' exonuclease activity, if present, might result in the destruction of the synthesized strand. DNA polymerases for use in the disclosed method can also be highly processive, if desired. The suitability of a DNA polymerase for use in the disclosed method can be readily determined by assessing its ability to carry out rolling circle replication. Preferred rolling circle DNA polymerases are Bst DNA polymerase, VENT® DNA polymerase (Kong et al., *J. Biol. Chem.* 268:1965–1975 (1993)), ThermoSequenase™, delta Tts DNA polymerase, bacteriophage $\phi$29 DNA polymerase (U.S. Pat. Nos. 5,198, 543 and 5,001,050 to Blanco et al.), phage M2 DNA polymerase (Matsumoto et al., *Gene* 84:247 (1989)), phage $\phi$PRD1 DNA polymerase (Jung et al., *Proc. Natl. Acad. Sci. USA* 84:8287 (1987)), Klenow fragment of DNA polymerase I (Jacobsen et al., *Eur. J. Biochem.* 45:623–627 (1974)), T5 DNA polymerase (Chatterjee et al., *Gene* 97:13–19 (1991)), PRD1 DNA polymerase (Zhu and Ito, Biochim. Biophys. Acta. 1219:267–276 (1994)), modified T7 DNA polymerase (Tabor and Richardson, *J. Biol. Chem.* 262:15330–15333 (1987); Tabor and Richardson, *J. Biol. Chem.* 264:6447–6458 (1989); Sequenase™ (U.S. Biochemicals)), and T4 DNA polymerase holoenzyme (Kaboord and Benkovic, *Curr. Biol.* 5:149–157 (1995)). More preferred are Bst DNA polymerase, VENT® DNA polymerase, ThermoSequenase™, and delta Tts DNA polymerase. Bst DNA polymerase is most preferred.

Strand displacement can be facilitated through the use of a strand displacement factor, such as helicase. It is considered that any DNA polymerase that can perform rolling circle replication in the presence of a strand displacement factor is suitable for use in the disclosed method, even if the DNA polymerase does not perform rolling circle replication in the absence of such a factor. Strand displacement factors useful in the disclosed method include BMRF1 polymerase accessory subunit (Tsurumi et al., *J. Virology* 67(12):7648-7653 (1993)), adenovirus DNA-binding protein (Zijderveld and van der Vliet, *J. Virology* 68(2):1158–1164 (1994)), herpes simplex viral protein ICP8 (Boehmer and Lehman, *J. Virology* 67(2):711–715 (1993); Skaliter and Lehman, *Proc. Natl. Acad. Sci. USA* 91(22):10665–10669 (1994)), single-stranded DNA binding proteins (SSB; Rigler and Romano, *J. Biol. Chem.* 270:8910–8919 (1995)), and calf thymus helicase (Siegel et at., *J. Biol. Chem.* 267:13629–13635 (1992)).

The ability of a polymerase to carry out rolling circle replication can be determined by using the polymerase in a rolling circle replication assay such as those described in Fire and Xu, *Proc. Natl. Acad. Sci. USA* 92:4641–4645 (1995) and in U.S. Pat. No. 6,143,495 (Example 1).

Another type of DNA polymerase can be used if a gap-filling synthesis step is used, such as in gap-filling LM-RCA (see U.S. Pat. No. 6,143,495, Example 3). When using a DNA polymerase to fill gaps, strand displacement by the DNA polymerase is undesirable. Such DNA polymerases are referred to herein as gap-filling DNA polymerases. Unless otherwise indicated, a DNA polymerase referred to herein without specifying it as a rolling circle DNA polymerase or a gap-filling DNA polymerase, is understood to be a rolling circle DNA polymerase and not a gap-filling DNA polymerase. Preferred gap-filling DNA polymerases are T7 DNA polymerase (Studier et al., *Methods Enzymol.* 185:60–89 (1990)), DEEP VENT® DNA polymerase (New England Biolabs, Beverly, Mass.), modified T7 DNA polymerase (Tabor and Richardson, *J. Biol. Chem.* 262:15330–15333 (1987); Tabor and Richardson, *J. Biol. Chem.* 264:6447–6458 (1989); Sequenase™ (U.S. Biochemicals)), and T4 DNA polymerase (Kunkel et al., *Methods Enzymol.* 154:367–382 (1987)). An especially preferred type of gap-filling DNA polymerase is the *Thermus flavus* DNA polymerase (MBR, Milwaukee, Wis.). The most preferred gap-filling DNA polymerase is the Stoffel fragment of Taq DNA polymerase (Lawyer et al., *PCR Methods Appl.* 2(4):275–287 (1993), King et al., *J. Biol. Chem.* 269(18):13061–13064 (1994)).

The ability of a polymerase to fill gaps can be determined by performing gap-filling LM-RCA. Gap-filling LM-RCA is performed with an open circle probe that forms a gap space when hybridized to the target sequence. Ligation can only occur when the gap space is filled by the DNA polymerase. If gap-filling occurs, TS-DNA can be detected, otherwise it can be concluded that the DNA polymerase, or the reaction conditions, is not useful as a gap-filling DNA polymerase.

O. RNA Polymerases

Any RNA polymerase which can carry out transcription in vitro and for which promoter sequences have been identified can be used in the disclosed rolling circle transcription method. Stable RNA polymerases without complex requirements are preferred. Most preferred are T7 RNA polymerase (Davanloo et al., *Proc. Natl. Acad. Sci. USA* 81:2035–2039 (1984)) and SP6 RNA polymerase (Butler and Chamberlin, *J. Biol. Chem.* 257:5772–5778 (1982)) which are highly specific for particular promoter sequences (Schenborn and Meirendorf, *Nucleic Acids Research* 13:6223–6236 (1985)). Other RNA polymerases with this characteristic are also preferred. Because promoter sequences are generally recognized by specific RNA polymerases, the OCP or ATC should contain a promoter sequence recognized by the RNA polymerase that is used. Numerous promoter sequences are known and any suitable RNA polymerase having an identified promoter sequence can be used. Promoter sequences for RNA polymerases can be identified using established techniques.

P. Kits

The materials described above can be packaged together in any suitable combination as a kit useful for performing the disclosed method. It is preferred that the kit components in a given kit be designed and adapted for use together in the disclosed method. A kit can include one or more open circle probes and one or more rolling circle replication primers. A kit can also include a secondary DNA strand displacement primer, a tertiary DNA strand displacement primer, or both. A kit can also include one or more gap oligonucleotides. The target probe portions of the open circle probes in a kit preferably are each complementary to a different target sequence. A kit can also include one or more detection probes. Preferably, a portion of each of the detection probes in a kit has sequence matching or complementary to a portion of a different one of the open circle probes in that kit.

A kit can also include one or more reporter binding agents where the oligonucleotide portion of the reporter binding agents include one of the target sequences. The specific binding molecules of the reporter binding agents in a kit each can be specific for an analyte, preferably specific for a protein or peptide.

A preferred kit for selectively detecting one or more target sequences or selectively amplifying nucleic acid sequences related to one or more target sequences can include a plurality of open circle probes, one or more rolling circle replication primers, and a plurality of detection probes. In this kit, it is preferred that at least one of the ends of one of the open circle probe can form an intramolecular stem structure, and that portions of each open circle probe are complementary to one or more target sequences such that the portions of the open circle probes that are complementary to the target sequence are complementary to a different target sequence for each of a plurality of the open circle probes. It is also preferred that all or a portion of each rolling circle replication primer is complementary to a portion of one or more of the open circle probes, and that a portion of each of the detection probes has sequence matching or complementary to a portion of a different one of the open circle probes.

Another preferred kit for selectively detecting one or more target sequences or selectively amplifying nucleic acid sequences related to one or more target sequences can include a plurality of open circle probes, one or more rolling circle replication primers, and a plurality of reporter binding agents. In this kit, it is preferred that at least one of the ends of one of the open circle probe can form an intramolecular stem structure, and that portions of each open circle probe are complementary to one or more target sequences such that the portions of the open circle probes that are complementary to the target sequence are complementary to a different target sequence for each of a plurality of the open circle probes. It is also preferred that all or a portion of each rolling circle replication primer is complementary to a portion of one or more of the open circle probes, and that the oligonucleotide portion of each reporter binding agent include target sequences. It is also preferred that the reporter binding agent s are specific for proteins or peptides. This kit can also include a plurality of detection probes, preferably where a portion of each of the detection probes has sequence matching or complementary to a portion of a different one of the open circle probes.

Method

The disclosed method involves the use of hairpin open circle probes, hairpin rolling circle replication primers, hairpin DNA strand displacement primers, or a combination, in a rolling circle amplification technique. For use of hairpin open circle probes, the basic method involves a ligation operation and an amplification operation. The ligation operation involves circularization of the open circle probe and is mediated by a target sequence to which the open circle probe is hybridized. A key feature of this operation is connection between an open circle probe and its cognate target sequence. Unless the target sequence is present (so that the open circle probe can hybridize to it), the open circle probe will not be circularized. The disclosed hairpin open circle probes can improve the specificity of open circle probe circularization by improving the specificity of hybridization.

The amplification operation involves rolling circle replication of the circularized open circle probe. The disclosed hairpin open circle probes can improve the amplification operation by reducing or eliminating non-specific priming by uncircularized open circle probes. Such non-specific priming can result in amplification of non-specific sequences, thus reducing the specificity of the amplification operation. The amplification operation uses rolling circle replication primers to prime replication of circularized open circle probes. The disclosed hairpin rolling circle replication primers can improve the amplification operation by reducing or eliminating non-specific priming by the rolling circle replication primers.

The amplification operation can also include replication of the product of rolling circle replication (referred to as secondary DNA strand displacement). This involves priming and replication of the tandem repeat DNA produced by rolling circle replication using secondary DNA strand displacement primers. The disclosed hairpin secondary DNA strand displacement primers can improve the amplification operation by reducing or eliminating non-specific priming by the secondary DNA strand displacement primers. The amplification operation can also include replication of the product of secondary DNA strand displacement (referred to as tertiary DNA strand displacement). This involves priming and replication of the tandem repeat DNA produced by secondary DNA strand displacement using tertiary DNA strand displacement primers. The disclosed hairpin tertiary DNA strand displacement primers can improve the amplification operation by reducing or eliminating non-specific priming by the tertiary DNA strand displacement primers.

The disclosed method is useful for detection, quantitation, and/or location of any desired analyte. The disclosed method can be multiplexed to detect numerous different analytes simultaneously or used in a single assay. Thus, the disclosed method is useful for detecting, assessing, quantitating, profiling, and/or cataloging gene expression and the presence of protein in biological samples. The disclosed method is also particularly useful for detecting and discriminating single nucleotide differences in nucleic acid sequences. This specificity is possible due to the sensitivity of the intramolecular stem structure in loop-containing probes and primers to mismatches between the loop sequence and a prospective target sequence. Thus, the disclosed method is useful for extensive multiplexing of target sequences for sensitive and specific detection of the target sequences themselves or analytes to which the target sequences have been associated. The disclosed method is also useful for detecting, assessing, quantitating, and/or cataloging single nucleotide polymorphisms, and other sequence differences between nucleic acids, nucleic acid samples, and sources of nucleic acid samples.

The disclosed method is useful for detecting any desired sequence or other analyte, such as proteins and peptides. In particular, the disclosed method can be used to localize or amplify signal from any desired analyte. For example, the disclosed method can be used to assay tissue, transgenic cells, bacterial or yeast colonies, cellular material (for example, whole cells, proteins, DNA fibers, interphase nuclei, or metaphase chromosomes on slides, arrayed genomic DNA, RNA), and samples and extracts from any of biological source. Where target sequences are associated with an analyte, different target sequences, and thus different analytes, can be sensitively distinguished. Specificity of such detection is aided by sensitivity of a loop in an open circle probe to mismatches.

The disclosed method is applicable to numerous areas including, but not limited to, analysis of proteins present in a sample (for example, proteomics analysis), disease detection, mutation detection, protein expression profiling, RNA expression profiling, gene discovery, gene mapping (molecular haplotyping), agricultural research, and virus detection. Preferred uses include protein and peptide detection in situ in cells, on microarrays, protein expression profiling; mutation detection; detection of abnormal proteins or peptides (for example, overexpression of an oncogene protein or absence of expression of a tumor suppressor protein); expression in cancer cells; detection of viral proteins in cells; viral protein expression; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer. The disclosed method can also be used for detection of nucleic acids in situ in cells, on microarrays, on DNA fibers, and on genomic DNA arrays; detection of RNA in cells; RNA expression profiling; molecular haplotyping; mutation detection; detection of abnormal RNA (for example, overexpression of an oncogene or absence of expression of a tumor suppressor gene); expression in cancer cells; detection of viral genome in cells; viral RNA expression; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

A. The Ligation Operation

An open circle probe, optionally in the presence of one or more gap oligonucleotides, is incubated with a sample containing nucleic acids, under suitable hybridization conditions, and then ligated to form a covalently closed circle. The ligated open circle probe is a form of amplification target circle. This operation is similar to ligation of padlock probes described by Nilsson et al., *Science,*

265:2085–2088 (1994). The ligation operation allows subsequent amplification to be dependent on the presence of a target sequence. Suitable ligases for the ligation operation are described above. Ligation conditions are generally known. Most ligases require $Mg^{++}$. There are two main types of ligases, those that are ATP-dependent and those that are NAD-dependent. ATP or NAD, depending on the type of ligase, should be present during ligation.

The disclosed hairpin open circle probes reduce the incidence of non-specific ligation of open circle probe ends because one or both of the ends remain in the intramolecular stem structure unless hybridized to a target sequence. Loop-containing open circle probes allow better discrimination of target sequence hybridization by the open circle probes. As discussed below, hybridization of sequences in the loop to target sequence can disrupt the intramolecular stem structure. In the absence of target sequence, the stem structure remains intact.

The target sequence for an open circle probe can be any nucleic acid or other compound to which the target probe portions of the open circle probe can hybridize in the proper alignment. Target sequences can be found in any nucleic acid molecule from any nucleic acid sample. Thus, target sequences can be in nucleic acids in cell or tissue samples, reactions, and assays. Target sequences can also be artificial nucleic acids (or other compounds to which the target probe portions of the open circle probe can hybridize in the proper alignment). For example, nucleic acid tags can be associated with various of the disclosed compounds to be detected using open circle probes. Thus, a reporter binding agent can contain a target sequence to which an open circle probe can hybridize. In these cases, the target sequence provides a link between the target molecule being detected and the amplification of signal mediated by the open circle probe.

When RNA is to be detected, it is preferred that a reverse transcription operation be performed to make a DNA target sequence. Alternatively, an RNA target sequence can be detected directly by using a ligase that can perform ligation on a DNA:RNA hybrid substrate. A preferred ligase for this is T4 DNA ligase.

B. The Amplification Operation

The basic form of amplification operation is rolling circle replication of a circular DNA molecule (that is, a circularized open circle probe or an amplification target circle). The circular open circle probes formed by specific ligation and amplification target circles serve as substrates for a rolling circle replication. This reaction requires two reagents: (a) a rolling circle replication primer, which is complementary to the primer complement portion of the OCP or ATC, and (b) a rolling circle DNA polymerase. The DNA polymerase catalyzes primer extension and strand displacement in a processive rolling circle polymerization reaction that proceeds as long as desired, generating a molecule of 100,000 nucleotides or more that contains up to approximately 1000 tandem copies or more of a sequence complementary to the amplification target circle or open circle probe. This tandem sequence DNA (TS-DNA) consists of, in the case of OCPs, alternating target sequence and spacer sequence. Note that the spacer sequence of the TS-DNA is the complement of the sequence between the left target probe and the right target probe in the original open circle probe.

During rolling circle replication one may additionally include radioactive, or modified nucleotides such as bromodeoxyuridine triphosphate, in order to label the DNA generated in the reaction. Alternatively, one may include suitable precursors that provide a binding moiety such as biotinylated nucleotides (Langer et al. (1981)). Unmodified TS-DNA can be detected using any nucleic acid detection technique.

As well as rolling circle replication, the amplification operation can include additional nucleic acid replication or amplification processes. For example, TS-DNA can itself be replicated to form secondary TS-DNA. This process is referred to as secondary DNA strand displacement. The combination of rolling circle replication and secondary DNA strand displacement is referred to as linear rolling circle amplification (LRCA). The secondary TS-DNA can itself be replicated to form tertiary TS-DNA in a process referred to as tertiary DNA strand displacement. Secondary and tertiary DNA strand displacement can be performed sequentially or simultaneously. When performed simultaneously, the result is strand displacement cascade amplification. The combination of rolling circle replication and strand displacement cascade amplification is referred to as exponential rolling circle amplification (ERCA). Secondary TS-DNA, tertiary TS-DNA, or both can be amplified by transcription.

After RCA, a round of LM-RCA can be performed on the TS-DNA produced in the first RCA. This new round of LM-RCA is performed with a new open circle probe, referred to as a secondary open circle probe, having target probe portions complementary to a target sequence in the TS-DNA produced in the first round. When such new rounds of LM-RCA are performed, the amplification is referred to as nested LM-RCA. Nested LM-RCA can also be performed on ligated OCPs or ATCs that have not been amplified. In this case, LM-RCA can be carried out using either ATCs or target-dependent ligated OCPs. This is especially useful for in situ detection. For in situ detection, the first, unamplified OCP, which is topologically locked to its target sequence, can be subjected to nested LM-RCA. By not amplifying the first OCP, it can remain hybridized to the target sequence while LM-RCA amplifies a secondary OCP topologically locked to the first OCP. Nested LM-RCA is described in U.S. Pat. No. 6,143,495.

C. Extension

The disclosed method uses hairpin probes and primers to reduce or eliminate non-specific and other undesired nucleic acid replication. This is accomplished by virtue of the probe and primer design (as described above) and results in "inactivation" of the probes and primer if they are not involved in legitimate hybrid. Such inactivation refers to the reduced ability of the probe or primer to hybridize to sequences other than their intended target sequence. As used herein, inactivation of probes and primers does not require complete loss of non-specific hybridization; reduction in non-specific hybridization is sufficient.

The disclosed open circle probes can be inactivated in several ways. For example, where the 3' end of an open circle probe is involved in an intramolecular stem structure, the 3' end can be extended in a replication reaction using the open circle probe sequences as template (see FIG. 2B). The result is stabilization of the intramolecular stem structure and a change in the 3' end sequence. Stabilization of the stem structure results in a reduction or elimination of the ability of the open circle probe to prime nucleic acid synthesis because the 3' end is stably hybridized to sequences in the open circle probe under the conditions used for nucleic acid replication. Change in the sequence of the 3' end can reduce of the ability of the open circle probe to prime nucleic acid synthesis because the changed 3' sequences may not be as closely related to sequences involved in the amplification reaction or assay. Change in the sequence of the 3' end can reduce of the ability of the open circle probe to serve as a template for rolling circle amplification. For example, even if the open circle probe with extended 3' end were circularized, the rolling circle replication primer could be prevented from priming replication of such a circle if the primer complement sequence on the open circle probe were interrupted by the added sequences. This can be accomplished by, for example, designing the open circle probe to have the primer complement sequence include both 5' and 3' end sequences of the open circle probe.

D. Sequestration

The open circle probe can also be inactivated by formation of the intramolecular stem structure during the amplification reaction. As long as the end remains in the intramolecular stem structure (that is, as long as it is sequestered in the stem structure), it is not available for priming nucleic acid synthesis. This form of inactivation is aided by design the intramolecular stem structure, or selecting amplification conditions, such that the intramolecular hybrid remains stable during rolling circle amplification. Extension of the end as described above also results in sequestration of the end in the intramolecular stem structure.

Discrimination of rolling circle replication primer hybridization also can be accomplished by hybridizing primer to primer complement portions of OCPs or ATCs under conditions that favor only exact sequence matches leaving other rolling circle replication primers unhybridized. The unhybridized rolling circle replication primers will retain or re-form the intramolecular hybrid. Discrimination of DNA strand displacement primer hybridization can be accomplished in a similar manner by hybridizing primer to TS-DNA under conditions that favor only exact sequence matches leaving other DNA strand displacement primers unhybridized.

E. Loop Hybridization Disruption

One form of the disclosed open circle probes includes a loop as part of the intramolecular stem structure. It is preferred that the loop contain sequences complementary to the target sequence. This allows the loop to nucleate hybridization of the open probe to the target sequence. Preferred forms of the loop-containing probes are characterized by a sequence discrimination capability that is markedly better that the comparable linear probes due to the competition between the structural interferences between folding due to intramolecular stem formation and linear rigidity due to hybridization of the probe sequence to the target (Tyagi and Kramer, Nat Biotechnol 14(3):303–8 (1996); Bonnet et al., Proc Natl Acad Sci USA 96(11):6171–6 (1999)). Preferred open circle probes of this type will not hybridize to mismatched sequences under suitable conditions because duplex hybridization of probe to target does not effectively compete with intramolecular stem formation of the structured probe. This makes the end(s) of the open circle probe involved in an intramolecular stem structure unavailable for ligation to circularize the probe and leave the 3' end available for inactivating extension. The presence of target sequence causes the correctly matched open circle probe to unfold, allowing the ends to hybridize to the target sequence and be coupled (see FIG. 3). Where sequences in the loop nucleate hybridization of the open circle probe to a target sequence, loop hybridization to a non-target sequence is unlikely to lead to circularization of the open circle probe. This is because it is unlikely that a non-target sequence will include adjacent sequences to which both the loop and open circle probe end can hybridize (see FIG. 4).

A hybridization nucleating loop can also be used in linear primers used for nucleic acid replication and amplification. Such a primer forms an intramolecular stem structure, including a loop. Loop-containing primers of this type will not hybridize to mismatched sequences under suitable conditions because duplex hybridization of probe to target does not effectively compete with intramolecular stem formation of the structured probe. This makes the end of the primer involved in an intramolecular stem structure unavailable for priming. The legitimate primer complement sequence causes the correctly matched primer to unfold, allowing the end to hybridize to the primer complement sequence and prime synthesis. Where sequences in the loop nucleate hybridization of the primer, loop hybridization to an illegitimate sequence is unlikely to lead to priming. This is because it is unlikely that an illegitimate sequence will include adjacent sequences to which both the loop and the primer end can hybridize. Including proximity-sensitive labels used in molecular beacon probes in such primers allows hybridization and priming by the primers to be detected through activation of the label upon disruption of the intramolecular stem structure (Tyagi and Kramer, Nat Biotechnol 14(3):303–8 (1996); Bonnet et al., Proc Natl Acad Sci USA 96(11):6171–6 (1999)).

F. Reporter Binding Agents With Target Sequences

A preferred form of the disclosed method uses reporter binding agents having target sequences as the oligonucleotide portion. The oligonucleotide portion of the reporter binding agent serves as a target sequence. The affinity portion of the reporter binding agent is a specific binding molecule specific for a target molecule of interest, such as proteins or peptides. The reporter binding agent is associated with the target molecule and detection of this interaction is mediated by rolling circle amplification. Unbound reporter binding agents can be removed by washing. Once the reporter binding agent is associated with a target molecule, a open circle probe is hybridized to the target sequence of the reporter binding agent, ligated, and amplified. The resulting TS-DNA is associated with the ligated open circle probe, thus associating the TS-DNA to the site of the target molecule.

Reporter binding agents are preferably used with a solid-state substrate and in combination with combinatorial multicolor coding. For this purpose, samples to be tested are incorporated into a solid-state sample, as described above. The solid-state substrate is preferably a glass slide and the solid-state sample preferably incorporates up to 256 individual target or assay samples arranged in dots. Multiple solid-state samples can be used to either test more individual samples, or to increase the number of distinct target sequences to be detected. In the later case, each solid-state sample has an identical set of samples dots, and the assay will be carried out using a different set of reporter binding agents and open circle probes, collectively referred to as a probe set, for each solid-state sample. This allows a large number of individuals and target sequences to be assayed in a single assay. By using up to six different labels, combinatorial multicolor coding allows up to 63 distinct targets to be detected on a single solid-state sample. When using multiple solid-state substrates and performing RCA with a different set of reporter binding agents and open circle probes for each solid-state substrate, the same labels can be used with each solid-state sample (although differences between OCPs in each set may require the use of different detection probes). For example, 10 replica slides, each with 256 target sample dots, can be subjected to RCA using 10 different sets of reporter binding agents and open circle probes, where each set is designed for combinatorial multicolor coding of 63 targets. This results in an assay for detection of 630 different target molecules.

After rolling circle amplification, a cocktail of detection probes is added, where the cocktail contains color combinations that are specific for each OCP. The design and combination of such detection probes for use in combinatorial multicolor coding is described elsewhere herein. It is preferred that the OCPs be designed with combinatorially coded detection tags to allow use of a single set of singly labeled detection probes. It is also preferred that collapsing detection probes be used.

G. Detection of Amplification Products

Products of the amplification operation can be detected using any nucleic acid detection technique. Many techniques are known for detecting nucleic acids. Several preferred forms of detection are described below. The nucleotide sequence of the amplified sequences also can be determined using any suitable technique.

1. Primary Labeling

Primary labeling consists of incorporating labeled moieties, such as fluorescent nucleotides, biotinylated nucleotides, digoxygenin-containing nucleotides, or bromodeoxyuridine, during rolling circle replication in RCA, or during transcription in RCT. For example, one may incorporate cyanine dye UTP analogs (Yu et al. (1994)) at a frequency of 4 analogs for every 100 nucleotides. A preferred method for detecting nucleic acid amplified in situ is to label the DNA during amplification with BrdUrd, followed by binding of the incorporated BUDR with a biotinylated anti-BUDR antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.).

2. Secondary Labeling

Secondary labeling consists of using suitable molecular probes, such as detection probes, to detect the amplified nucleic acids. For example, an open circle may be designed to contain several repeats of a known arbitrary sequence, referred to as detection tags. A secondary hybridization step can be used to bind detection probes to these detection tags (see FIG. 7 in U.S. Pat. No. 6,143,495). The detection probes may be labeled as described above with, for example, an enzyme, fluorescent moieties, or radioactive isotopes. By using three detection tags per open circle probe, and four fluorescent moieties per each detection probe, one may obtain a total of twelve fluorescent signals for every open circle probe repeat in the TS-DNA, yielding a total of 12,000 fluorescent moieties for every ligated open circle probe that is amplified by RCA.

3. Multiplexing and Hybridization Array Detection

RCA is easily multiplexed by using sets of different open circle probes, each set carrying different target probe sequences designed for binding to unique targets. Note that although the target probe sequences designed for each target are different, the primer complement portion may remain unchanged, and thus the primer for rolling circle replication can remain the same for all targets. Only those open circle probes that are able to find their targets will give rise to TS-DNA. The TS-DNA molecules generated by RCA are of high molecular weight and low complexity; the complexity being the length of the open circle probe. There are two alternatives for capturing a given TS-DNA to a fixed position in a solid-state detector. One is to include within the spacer region of the open circle probes a unique address tag sequence for each unique open circle probe. TS-DNA generated from a given open circle probe will then contain sequences corresponding to a specific address tag sequence. A second and preferred alternative is to use the target sequence present on the TS-DNA as the address tag.

4. Combinatorial Multicolor Coding

A preferred form of multiplex detection involves the use of a combination of labels that either fluoresce at different wavelengths or are colored differently. One of the advantages of fluorescence for the detection of hybridization probes is that several targets can be visualized simultaneously in the same sample. Using a combinatorial strategy, many more targets can be discriminated than the number of spectrally resolvable fluorophores. Combinatorial labeling provides the simplest way to label probes in a multiplex fashion since a probe fluor is either completely absent (−) or present in unit amounts (+); image analysis is thus more amenable to automation, and a number of experimental artifacts, such as differential photobleaching of the fluors and the effects of changing excitation source power spectrum, are avoided.

The combinations of labels establish a code for identifying different detection probes and, by extension, different target molecules to which those detection probes are associated with. This labeling scheme is referred to as Combinatorial Multicolor Coding (CMC). Such coding is described by Speicher et al., Nature Genetics 12:368–375 (1996). Use of CMC in connection with rolling circle amplification is described in U.S. Pat. No. 6,143,495. Any number of labels, which when combined can be separately detected, can be used for combinatorial multicolor coding. It is preferred that 2, 3, 4, 5, or 6 labels be used in combination. It is most preferred that 6 labels be used. The number of labels used establishes the number of unique label combinations that can be formed according to the formula $2^N-1$, where N is the number of labels. According to this formula, 2 labels forms three label combinations, 3 labels forms seven label combinations, 4 labels forms 15 label combinations, 5 labels form 31 label combinations, and 6 labels forms 63 label combinations.

For combinatorial multicolor coding, a group of different detection probes are used as a set. Each type of detection probe in the set is labeled with a specific and unique combination of fluorescent labels. For those detection probes assigned multiple labels, the labeling can be accomplished by labeling each detection probe molecule with all of the required labels. Alternatively, pools of detection probes of a given type can each be labeled with one of the required labels. By combining the pools, the detection probes will, as a group, contain the combination of labels required for that type of detection probe. Where each detection probe is labeled with a single label, label combinations can also be generated by using OCPs or ATCs with coded combinations of detection tags complementary to the different detection probes. In this scheme, the OCPs or ATCs will contain a combination of detection tags representing the combination of labels required for a specific label code. Further illustrations are described in U.S. Pat. No. 6,143,495.

As described below, rolling circle amplification can be engineered to produce TS-DNA of different lengths in an assay involving multiple ligated OCPs or ATCs. The resulting TS-DNA of different length can be distinguished simply on the basis of the size of the detection signal they generate. Thus, the same set of detection probes could be used to distinguish two different sets of generated TS-DNA. In this scheme, two different TS-DNAs, each of a different size but assigned the same color code, would be distinguished by the size of the signal produced by the hybridized detection probes. In this way, a total of 126 different targets can be distinguished on a single solid-state sample using a code with 63 combinations, since the signals will come in two flavors, low amplitude and high amplitude. Thus one could, for example, use the low amplitude signal set of 63 probes for detection of an oncogene mutations, and the high amplitude signal set of 63 probes for the detection of a tumor suppressor p53 mutations.

Speicher et al. describes a set of fluors and corresponding optical filters spaced across the spectral interval 350–770 nm that give a high degree of discrimination between all possible fluor pairs. This fluor set, which is preferred for combinatorial multicolor coding, consists of 4'-6-diamidino-2-phenylinodole (DAPI), fluorescein (FITC), and the cyanine dyes Cy3, Cy3.5, Cy5, Cy5.5 and Cy7. Any subset of this preferred set can also be used where fewer combinations are required. The absorption and emission maxima, respectively, for these fluors are: DAPI (350 nm; 456 nm), FITC (490 nm; 520 nm), Cy3 (554 nm; 568 nm), Cy3.5 (581 nm; 588 nm), Cy5 (652 nm; 672 nm), Cy5.5 (682 nm; 703 nm) and Cy7 (755 nm; 778 nm). The excitation and emission spectra, extinction coefficients and quantum yield of these fluors are described by Ernst et al., *Cytometry* 10:3–10 (1989), Mujumdar et al., *Cytometry* 10:11–19 (1989), Yu, *Nucleic Acids Res.* 22:3226–3232 (1994), and Waggoner, *Meth. Enzymology* 246:362–373 (1995). These fluors can all be excited with a 75W Xenon arc.

To attain selectivity, filters with bandwidths in the range of 5 to 16 nm are preferred. To increase signal discrimination, the fluors can be both excited and detected at wavelengths far from their spectral maxima. Emission bandwidths can be made as wide as possible. For low-noise detectors, such as cooled CCD cameras, restricting the excitation bandwidth has little effect on attainable signal to noise ratios. A list of preferred filters for use with the preferred fluor set is listed in Table 1 of Speicher et al. It is important to prevent infra-red light emitted by the arc lamp from reaching the detector; CCD chips are extremely sensitive in this region. For this purpose, appropriate IR blocking filters can be inserted in the image path immediately in front of the CCD window to minimize loss of image quality. Image analysis software can then be used to count and analyze the spectral signatures of fluorescent dots.

Discrimination of individual signals in combinatorial multicolor coding can be enhanced by collapsing TS-DNA generated during amplification. As described elsewhere herein, this is preferably accomplished using collapsing detection probes, biotin-antibody conjugates, or a combination of both. A collapsed TS-DNA can occupy a space of no more than 0.3 microns in diameter. Based on this, it is expected that up to a million discrete signals can be detected in a 2.5 mm sample dot. Such discrimination also results in a large dynamic range for quantitative signal detection. Thus, the relative numbers of different types of signals (such as multicolor codes) can be determined over a wide range. This is expected to allow determination of, for example, the relative amount of different target molecules, such as proteins, in a sample. Such comparative detections would be useful in, for example, proteomics analyses of cell and tissue samples. This would also allow determination of whether a particular target sequence is homozygous or heterozygous in a genomic DNA sample, whether a target sequence was inherited or represents a somatic mutation, and the genetic heterogeneity of a genomic DNA sample, such as a tumor sample.

5. Detecting Multiple Target Sequences

Multiplex RCA assays are particularly useful for detecting multiple proteins. A single LM-RCA assay can be used to detect the presence of one or more members of a group of any number of target sequences. By associating different target sequences with different proteins (using reporter binding agents specific for the proteins of interest), each different protein can be detected by differential detection of the various target sequences. This can be accomplished, for example, by designing an open circle probe (and associated gap oligonucleotides, if desired) for each target sequence in the group, where the target probe portions and the sequence of the detection tag portions of each open circle probe are different but the sequence of the primer portions of all the open circle probes are the same. All of the open circle probes are placed in the same OCP-target sample mixture, and the same primer is used to amplify. Different detection probes are used to detect the various TS-DNAs (each having specific detection tag sequences). For each target sequence present in the assay (those associated with proteins present in the target sample, for example), the OCP for that target will be ligated into a circle and the circle will be amplified to form TS-DNA. Since the detection tags on TS-DNA resulting from amplification of the OCPs are the different, TS-DNA resulting from ligation each OCP can be detected individually in that assay.

6. Detecting Groups of Target Sequences

Multiplex RCA assays are particularly useful for detecting any of a set of target sequences in a defined group. For example, the disclosed method can be used to detect mutations in genes where numerous distinct mutations are associated with certain diseases or where mutations in multiple genes are involved. For example, although the gene responsible for Huntington's chorea has been identified, a wide range of mutations in different parts of the gene occur among affected individuals. The result is that no single test has been devised to detect whether an individual has one or more of the many Huntington's mutations. A single LM-RCA assay can be used to detect the presence of one or more members of a group of any number of target sequences. This can be accomplished, for example, by designing an open circle probe (and associated gap oligonucleotides, if desired) for each target sequence in the group, where the target probe portions of each open circle probe are different but the sequence of the primer portions and the sequence of the detection tag portions of all the open circle probes are the same. All of the open circle probes are placed in the same OCP-target sample mixture, and the same primer and detection probe are used to amplify and detect TS-DNA. If any of the target sequences are present in the target sample, the OCP for that target will be ligated into a circle and the circle will be amplified to form TS-DNA. Since the detection tags on TS-DNA resulting from amplification of any of the OCPs are the same, TS-DNA resulting from ligation of any of the OCPs will be detected in that assay. Detection indicates that at least one member of the target sequence group is present in the target sample. This allows detection of a trait associated with multiple target sequences in a single tube or well.

If a positive result is found, the specific target sequence involved can be identified by using a multiplex assay. This can be facilitated by including an additional, different detection tag in each of the OCPs of the group. In this way, TS-DNA generated from each different OCP, representing each different target sequence, can be individually detected. It is convenient that such multiple assays need be performed only when an initial positive result is found.

The above scheme can also be used with arbitrarily chosen groups of target sequences in order to screen for a large number of target sequences without having to perform an equally large number of assays. Initial assays can be performed as described above, each using a different group of OCPs designed to hybridize to a different group of target sequences. Additional assays to determine which target sequence is present can then be performed on only those groups that produce TS-DNA. Such group assays can be further nested if desired.

7. In Situ Detection Using RCA

In situ detection of target sequences is a powerful application of the disclosed method. For example, open circle probes can be ligated on targets immobilized on a substrate, and incubated in situ with fluorescent precursors during rolling circle replication. The circle will remain topologically trapped on the chromosome unless the DNA is nicked (Nilsson et al. (1994)). The resulting TS-DNA will then be associated with the location of the target sequence.

A preferred method of in situ detection uses reporter binding agents having target sequences as the oligonucleotide portion. In this form of the method, reporter binding agents having target sequences as the oligonucleotide portion are associated with target molecules (such as proteins) that are immobilized or otherwise attached to a substrate. Once the reporter binding agent is associated with a target molecule, an open circle probe is hybridized to the target sequence of the reporter binding agent and circularized. The circularized open circle probe is then amplified. The resulting TS-DNA is associated with the site of the target molecule via the open circle probe and reporter binding agent.

Localization of the TS-DNA for in situ detection can also be enhanced by collapsing the TS-DNA using collapsing detection probes, biotin-antibody conjugates, or both, as described elsewhere herein. Multiplexed in situ detection can be carried out as follows: Rolling circle replication is carried out using unlabeled nucleotides. The different TS-DNAs are then detected using standard multi-color FISH with detection probes specific for each unique target sequence or each unique detection tag in the TS-DNA. Alternatively, and preferably, combinatorial multicolor coding, as described above, can be used for multiplex in situ detection.

Another method of in situ detection uses reporter binding agents having rolling circle replication primers as the oligonucleotide portion (this is referred to as Reporter Binding Agent Unimolecular Rolling Amplification (RBAURA) in U.S. Pat. No. 6,143,495). In RBAURA, a reporter binding agent is used where the oligonucleotide portion serves as a rolling circle replication primer. Once the reporter binding agent is associated with a target molecule, an amplification target circle is hybridized to the rolling circle replication primer sequence of the reporter binding agent followed by amplification of the ATC by RCA. The resulting TS-DNA has the rolling circle replication primer sequence of the reporter binding agent at one end, thus anchoring the TS-DNA to the site of the target molecule. Peptide Nucleic Acid Probe Unimolecular Rolling Amplification (PNAPURA) and Locked Antibody Unimolecular Rolling Amplification (LAURA), described in U.S. Pat. No. 6,143,495, are preferred forms of RBAURA.

8. Enzyme-linked Detection

Amplified nucleic acid labeled by incorporation of labeled nucleotides can be detected with established enzyme-linked detection systems. For example, amplified nucleic acid labeled by incorporation of biotin-16-UTP (Boehringher Mannheim) can be detected as follows. The nucleic acid is immobilized on a solid glass surface by hybridization with a complementary DNA oligonucleotide (address probe) complementary to the target sequence (or its complement) present in the amplified nucleic acid. After hybridization, the glass slide is washed and contacted with alkaline phosphatase-streptavidin conjugate (Tropix, Inc., Bedford, Mass.). This enzyme-streptavidin conjugate binds to the biotin moieties on the amplified nucleic acid. The slide is again washed to remove excess enzyme conjugate and the chemiluminescent substrate CSPD (Tropix, Inc.) is added and covered with a glass cover slip. The slide can then be imaged in a Biorad Fluorimager.

9. Collapse of Nucleic Acids

Tandem sequence DNA or TS-RNA, which are produced as extended nucleic acid molecules, can be collapsed into a compact structure. It is preferred that the nucleic acid to be collapsed is immobilized on a substrate. A preferred means of collapsing nucleic acids is by hybridizing one or more collapsing probes with the nucleic acid to be collapsed. Collapsing probes are oligonucleotides having a plurality of portions each complementary to sequences in the nucleic acid to be collapsed. These portions are referred to as complementary portions of the collapsing probe, where each complementary portion is complementary to a sequence in the nucleic acid to be collapsed. The sequences in the nucleic acid to be collapsed are referred to as collapsing target sequences. The complementary portion of a collapsing probe can be any length that supports specific and stable hybridization between the collapsing probe and the collapsing target sequence. For this purpose, a length of 10 to 35 nucleotides is preferred, with a complementary portion of a collapsing probe 16 to 20 nucleotides long being most preferred. It is preferred that at least two of the complementary portions of a collapsing probe be complementary to collapsing target sequences which are separated on the nucleic acid to be collapsed or to collapsing target sequences present in separate nucleic acid molecules. This allows each detection probe to hybridize to at least two separate collapsing target sequences in the nucleic acid sample. In this way, the collapsing probe forms a bridge between different parts of the nucleic acid to be collapsed. The combined action of numerous collapsing probes hybridizing to the nucleic acid will be to form a collapsed network of cross-linked nucleic acid. Collapsed nucleic acid occupies a much smaller volume than free, extended nucleic acid, and includes whatever detection probe or detection label hybridized to the nucleic acid. This result is a compact and discrete nucleic acid structure which can be more easily detected than extended nucleic acid. Collapsing nucleic acids is useful both for in situ hybridization applications and for multiplex detection because it allows detectable signals to be spatially separate even when closely packed. Collapsing nucleic acids is especially preferred for use with combinatorial multicolor coding. Collapsing probes can also contain any of the detection labels described above. TS-DNA collapse can also be accomplished through the use of ligand/ligand binding pairs (such as biotin and avidin) or hapten/antibody pairs. Nucleic acid collapse is further described in U.S. Pat. No. 6,143,495.

G. DNA Strand Displacement

DNA strand displacement is one way to amplify TS-DNA. Secondary DNA strand displacement is accomplished by hybridizing secondary DNA strand displacement primers to TS-DNA and allowing a DNA polymerase to synthesize DNA from these primed sites (see FIG. 11 in U.S. Pat. No. 6,143,495). Because a complement of the secondary DNA strand displacement primer occurs in each repeat of the TS-DNA, secondary DNA strand displacement can result in a high level of amplification. The product of secondary DNA strand displacement is referred to as secondary tandem sequence DNA or TS-DNA-2. Secondary DNA strand displacement can be accomplished by performing RCA to produce TS-DNA, mixing secondary DNA strand displacement primer with the TS-DNA, and incubating under conditions promoting replication of the tandem sequence DNA. The disclosed hairpin open circle probes are especially useful for DNA strand displacement because inactivated hairpin open circle probes will not compete with secondary DNA strand displacement primers for hybridization to TS-DNA. The DNA strand displacement primers are preferably hairpin DNA strand displacement primers.

Secondary DNA strand displacement can also be carried out simultaneously with rolling circle replication. This is accomplished by mixing secondary DNA strand displacement primer with the reaction prior to rolling circle replication. As a secondary DNA strand displacement primer is elongated, the DNA polymerase will run into the 5' end of the next hybridized secondary DNA strand displacement molecule and will displace its 5' end. In this fashion a tandem queue of elongating DNA polymerases is formed on the TS-DNA template. As long as the rolling circle reaction continues, new secondary DNA strand displacement primers and new DNA polymerases are added to TS-DNA at the growing end of the rolling circle. The generation of TS-DNA-2 and its release into solution by strand displacement is shown diagrammatically in FIG. 11 in U.S. Pat. No. 6,143,495. For simultaneous rolling circle replication and secondary DNA strand displacement, it is preferred that the rolling circle DNA polymerase be used for both replications. This allows optimum conditions to be used and results in displacement of other strands being synthesized downstream. Secondary DNA strand displacement can follow any DNA replication operation, such as RCA, LM-RCA or nested LM-RCA.

Generally, secondary DNA strand displacement can be performed by, simultaneous with or following RCA, mixing a secondary DNA strand displacement primer with the reaction mixture and incubating under conditions that promote both hybridization between the tandem sequence DNA and the secondary DNA strand displacement primer, and replication of the tandem sequence DNA, where replication of the tandem sequence DNA results in the formation of secondary tandem sequence DNA.

When secondary DNA strand displacement is carried out in the presence of a tertiary DNA strand displacement primer, an exponential amplification of TS-DNA sequences takes place. This special and preferred mode of DNA strand displacement is referred to as strand displacement cascade amplification (SDCA). In SDCA, a secondary DNA strand displacement primer primes replication of TS-DNA to form TS-DNA-2, as described above. The tertiary DNA strand displacement primer strand can then hybridize to, and prime replication of, TS-DNA-2 to form TS-DNA-3. Strand displacement of TS-DNA-3 by the adjacent, growing TS-DNA-3 strands makes TS-DNA-3 available for hybridization with secondary DNA strand displacement primer. This results in another round of replication resulting in TS-DNA-4 (which is equivalent to TS-DNA-2). TS-DNA-4, in turn, becomes a template for DNA replication primed by tertiary DNA strand displacement primer. The cascade continues this manner until the reaction stops or reagents become limiting. This reaction amplifies DNA at an almost exponential rate. In a preferred mode of SDCA, the rolling circle replication primer serves as the tertiary DNA strand displacement primer, thus eliminating the need for a separate primer.

For this mode, the rolling circle replication primer should be used at a concentration sufficiently high to obtain rapid priming on the growing TS-DNA-2 strands. To optimize the efficiency of SDCA, it is preferred that a sufficient concentration of secondary DNA strand displacement primer and tertiary DNA strand displacement primer be used to obtain sufficiently rapid priming of the growing TS-DNA strand to outcompete TS-DNA for binding to its complementary TS-DNA. Optimization of primer concentrations are described in U.S. Pat. No. 6,143,495 and can be aided by analysis of hybridization kinetics (Young and Anderson, "Quantitative analysis of solution hybridization" in *Nucleic Acid Hybridization: A Practical Approach* (IRL Press, 1985) pages 47–71).

Generally, strand displacement cascade amplification can be performed by, simultaneous with, or following, RCA, mixing a secondary DNA strand displacement primer and a tertiary DNA strand displacement primer with the reaction mixture and incubating under conditions that promote hybridization between the tandem sequence DNA and the secondary DNA strand displacement primer, replication of the tandem sequence DNA—where replication of the tandem sequence DNA results in the formation of secondary tandem sequence DNA—hybridization between the secondary tandem sequence DNA and the tertiary DNA strand displacement primer, and replication of secondary tandem sequence DNA—where replication of the secondary tandem sequence DNA results in formation of tertiary tandem sequence DNA (TS-DNA-3).

Secondary and tertiary DNA strand displacement can also be carried out sequentially. Following a first round of secondary DNA strand displacement, a tertiary DNA strand displacement primer can be mixed with the secondary tandem sequence DNA and incubated under conditions that promote hybridization between the secondary tandem sequence DNA and the tertiary DNA strand displacement primer, and replication of secondary tandem sequence DNA, where replication of the secondary tandem sequence DNA results in formation of tertiary tandem sequence DNA (TS-DNA-3). This round of strand displacement replication can be referred to as tertiary DNA strand displacement. However, all rounds of strand displacement replication following rolling circle replication can also be referred to collectively as DNA strand displacement or secondary DNA strand displacement.

A modified form of secondary DNA strand displacement results in amplification of TS-DNA and is referred to as opposite strand amplification (OSA). OSA is the same as secondary DNA strand displacement except that a special form of rolling circle replication primer is used that prevents it from hybridizing to TS-DNA-2. Opposite strand amplification is described in U.S. Pat. No. 6,143,495.

The DNA generated by DNA strand displacement can be labeled and/or detected using the same labels, labeling methods, and detection methods described for use with TS-DNA. Most of these labels and methods are adaptable for use with nucleic acids in general. A preferred method of labeling the DNA is by incorporation of labeled nucleotides during synthesis.

H. Transcription Following RCA

Once TS-DNA is generated using RCA, further amplification can be accomplished by transcribing the TS-DNA from promoters embedded in the TS-DNA. This combined process, referred to as rolling circle replication with transcription (RCT), or ligation mediated rolling circle replication with transcription (LM-RCT), requires that the OCP or ATC from which the TS-DNA is made have a promoter portion in its spacer region. The promoter portion is then amplified along with the rest of the OCP or ATC resulting in a promoter embedded in each tandem repeat of the TS-DNA. Because transcription, like rolling circle amplification, is a process that can go on continuously (with re-initiation), multiple transcripts can be produced from each of the multiple promoters present in the TS-DNA. RCT effectively adds another level of amplification of ligated OCP sequences.

Generally, RCT can be accomplished by performing RCA to produce TS-DNA, and then mixing RNA polymerase with the reaction mixture and incubating under conditions promoting transcription of the tandem sequence DNA. The OCP or ATC must include the sequence of a promoter for the RNA polymerase (a promoter portion) in its spacer region for RCT to work. The transcription step in RCT generally can be performed using established conditions for in vitro transcription of the particular RNA polymerase used. Alternatively, transcription can be carried out simultaneously with rolling circle replication. This is accomplished by mixing RNA polymerase with the reaction mixture prior to rolling circle replication. Transcription can follow any DNA replication operation, such as RCA, LM-RCA, nested LM-RCA, DNA strand displacement, or strand displacement cascade amplification.

The transcripts generated in RCT can be labeled and/or detected using the same labels, labeling methods, and detection methods described for use with TS-DNA. Most of these labels and methods are adaptable for use with nucleic acids in general. A preferred method of labeling RCT transcripts is by direct labeling of the transcripts by incorporation of labeled nucleotides, most preferably biotinylated nucleotides, during transcription.

I. Gap-Filling Ligation

The gap space formed by an OCP hybridized to a target sequence is normally occupied by one or more gap oligonucleotides as described above. Such a gap space may also be filled in by a gap-filling DNA polymerase during the ligation operation. As an alternative, the gap space can be partially bridged by one or more gap oligonucleotides, with the remainder of the gap filled using DNA polymerase. This modified ligation operation is referred to herein as gap-filling ligation and is a preferred form of the ligation operation. The principles and procedure for gap-filling ligation are generally analogous to the filling and ligation performed in gap LCR (Wiedmann et al., *PCR Methods and Applications* (Cold Spring Harbor Laboratory Press, Cold Spring Harbor Laboratory, N.Y., 1994) pages S51–S64; Abravaya et al., *Nucleic Acids Res.*, 23(4):675–682 (1995); European Patent Application EP0439182 (1991)). In the case of LM-RCA, the gap-filling ligation operation is substituted for the normal ligation operation. Gap-filling ligation provides a means for discriminating between closely related target sequences. Gap-filling ligation can be accomplished by using a different DNA polymerase, referred to herein as a gap-filling DNA polymerase. Suitable gap-filling DNA polymerases are described above. Alternatively, DNA polymerases in general can be used to fill the gap when a stop base is used. The use of stop bases in the gap-filling operation of LCR is described in European Patent Application EP0439182. The principles of the design of gaps and the ends of flanking probes to be joined, as described in EP0439182, is generally applicable to the design of the gap spaces and the ends of target probe portions described herein. Gap-filling ligation is further described in U.S. Pat. No. 6,143,495.

J. Reporter Binding Agent Unimolecular Rolling Amplification

Reporter Binding Agent Unimolecular Rolling Amplification (RBAURA) is a form of RCA where a reporter binding agent provides the rolling circle replication primer for amplification of an amplification target circle. In RBAURA, the oligonucleotide portion of the reporter binding agent serves as a rolling circle replication primer. The rolling circle replication primer should be a hairpin rolling circle replication primer. RBAURA allows RCA to produce an amplified signal (that is, TS-DNA) based on association of the reporter binding agent to a target molecule. The specific primer sequence that is a part of the reporter binding agent provides the link between the specific interaction of the reporter binding agent to a target molecule (via the affinity portion of the reporter binding agent) and RCA. In RBAURA, once the reporter binding agent is associated with a target molecule, an amplification target circle is hybridized to the rolling circle replication primer sequence of the reporter binding agent, followed by amplification of the ATC by RCA. The resulting TS-DNA incorporates the rolling circle replication primer sequence of the reporter binding agent at one end, thus anchoring the TS-DNA to the site of the target molecule. RBAURA is a preferred RCA method for in situ detections. For this purpose, it is preferred that the TS-DNA is collapsed using collapsing detection probes, biotin-antibody conjugates, or both, as described above. RBAURA can be performed using any target molecule. Preferred target molecules are nucleic acids, including amplified nucleic acids such as TS-DNA and amplification target circles, antigens and ligands. Examples of the use of such target molecules are described in U.S. Pat. No. 6,143, 495. Peptide Nucleic Acid Probe Unimolecular Rolling Amplification (PNAPURA) and Locked Antibody Unimolecular Rolling Amplification (LAURA), described in U.S. Pat. No. 6,143,495, are preferred forms of RBAURA.

K. Discrimination Between Closely Related Target Sequences

Open circle probes, gap oligonucleotides, and gap spaces can be designed to discriminate closely related target sequences, such as genetic alleles. Where closely related target sequences differ at a single nucleotide, it is preferred that open circle probes be designed with the complement of this nucleotide occurring at one end of the open circle probe, or at one of the ends of the gap oligonucleotide(s). Where gap-filling ligation is used, it is preferred that the distinguishing nucleotide appear opposite the gap space. This allows incorporation of alternative (that is, allelic) sequence into the ligated OCP without the need for alternative gap oligonucleotides. Where gap-filling ligation is used with a gap oligonucleotide(s) that partially fills the gap, it is preferred that the distinguishing nucleotide appear opposite the portion of gap space not filled by a gap oligonucleotide. Ligation of gap oligonucleotides with a mismatch at either terminus is extremely unlikely because of the combined effects of hybrid instability and enzyme discrimination. When the TS-DNA is generated, it will carry a copy of the gap oligonucleotide sequence that led to a correct ligation. Gap oligonucleotides may give even greater discrimination between related target sequences in certain circumstances, such as those involving wobble base pairing of alleles. Features of open circle probes and gap oligonucleotides that increase the target-dependency of the ligation operation are generally analogous to such features developed for use with the ligation chain reaction. These features can be incorporated into open circle probes and gap oligonucleotides for use in LM-RCA. In particular, European Patent Application EP0439182 describes several features for enhancing target-dependency in LCR that can be adapted for use in LM-RCA. The use of stop bases in the gap space, as described in European Patent Application EP0439182, is a preferred mode of enhancing the target discrimination of a gap-filling ligation operation.

A preferred form of target sequence discrimination can be accomplished by employing two types of open circle probes. In one embodiment, a single gap oligonucleotide is used which is the same for both target sequences, that is, the gap oligonucleotide is complementary to both target sequences. In a preferred embodiment, a gap-filling ligation operation can be used (Example 3 in U.S. Pat. No. 6,143,495). Target sequence discrimination would occur by virtue of mutually exclusive ligation events, or extension-ligation events, for which only one of the two open-circle probes is competent. Preferably, the discriminator nucleotide would be located at the penultimate nucleotide from the 3' end of each of the open circle probes. The two open circle probes would also contain two different detection tags designed to bind alternative detection probes and/or address probes. Each of the two detection probes would have a different detection label. Both open circle probes would have the same primer complement portion. Thus, both ligated open circle probes can be amplified using a single primer. Upon array hybridization, each detection probe would produce a unique signal, for example, two alternative fluorescence colors, corresponding to the alternative target sequences.

L. Size Classes of Tandem Sequence DNA

Rolling circle amplification can be engineered to produce TS-DNA of different lengths in an assay involving multiple ligated OCPs or ATCs. This can be useful for extending the number of different targets that can be detected in a single assay. TS-DNA of different lengths can be produced in several ways. In one embodiment, the base composition of the spacer region of different classes of OCP or ATC can be designed to be rich in a particular nucleotide. Then a small amount of the dideoxy nucleotide complementary to the enriched nucleotide can be included in the rolling circle amplification reaction. After some amplification, the dideoxy nucleotides will terminate extension of the TS-DNA product of the class of OCP or ATC enriched for the complementary nucleotide. Other OCPs or ATCs will be less likely to be terminated, since they are not enriched for the complementary nucleotide, and will produce longer TS-DNA products, on average.

In another embodiment, two different classes of OCP or ATC can be designed with different primer complement portions. These different primer complement portions are designed to be complementary to a different rolling circle replication primer. Then the two different rolling circle replication primers are used together in a single rolling circle amplification reaction, but at significantly different concentrations. The primer at high concentration immediately primes rolling circle replication due to favorable kinetics, while the primer at lower concentration is delayed in priming due to unfavorable kinetics. Thus, the TS-DNA product of the class of OCP or ATC designed for the primer at high concentration will be longer than the TS-DNA product of the class of OCP or ATC designed for the primer at lower concentration since it will have been replicated for a longer period of time. These and other techniques for producing size classes of TS-DNA are described in U.S. Pat. No. 6,143,495.

EXAMPLES

Example 1

Primer Extension Assay

This example demonstrates that a hairpin open circle probe with a 5' overhanging end can be extended from the 3' end. Such extension would lead to an inactive open circle probe. Open circle probe 1822ocT was used as a model for the new design of 3' hairpin open circle probes. The new design was compared to the conventional design.

```
Conventional OCP design sequence:
5'-phosphate-
GAAGAACTGGACAGATTTACTACGTATGTTGACTGGTCACACGTCGT
TCTAGTACGCTTCTACTCCCTCTTGAGATGTTCTGCTTTGTT 3'
(SEQ ID NO:1)

New (hairpin) OCP design sequence:
5'-phosphate-
GAAGAACTGGACAGATTTACTACGTATGTTGACTGGTCACACGTC
GTTCTAGTAACAAAGCACTCCCTCTTGAGATGTTCTGCTTTGTT 3'
(SEQ ID NO:2)
```

$\gamma^{32}P$ ATP exchange reaction end labeling: M13 bacteriophage forward primer and OCPs were end labeled with radioactive $^{32}P$ in an exchange reaction as follows:

30 minutes exchange reactions were carried out in 20 μl volume containing 10 μl of M13 bacteriophage forward primer or open circle probe DNA (1 pM/μl), 4 μl 5× exchange buffer (Gibco BRL, cat #10456-010) (250 mM imidazole-HCl (pH 6.4), 60 mM $MgCl_2$, 5 mM 2-mercaptoethanol, and 0.35 mM ADP), 0.5 μl T4 polynucleotide kinase (NEB) (10 u/μl), 2.5 μl dH2O, and 3 μl 10 mM $\gamma^{32}P$ ATP (10 μCi/μl). DNA was purified and eluted into 100 μl of EB buffer (10 mM Tris-HCl, pH 8.5) using QIAquick nucleotide removal kit (QIAGEN).

Annealing of $\gamma^{32}P$ ATP labeled forward primer to M13 DNA: Annealing reaction was carried out by mixing: 3.3 μl forward primer, 7.6 μl M13 mp19 ssDNA (0.25 μg/μl), 1 μl Tris-HCl (pH 7.54), and 18.1 μl $dH_2O$. Heated to 95° C. for 2 minutes, and cooled to room temperature.

M13 ladder preparation: 4 μl of the above reaction was added to 1 μl 0.1 M DTT, 7.6 μl 50× sequenase buffer (260 mM Tris-HCl, pH 9.5, 65 mM $MgCl_2$), 7.6 μl $dH_2O$, and 0.4 μl sequenase (USB) (4 units/μl). The mix was divided into 4 equal portions and 2.5 μl of ddG, ddA, ddT, or ddC was added into each portion. All four portions were then incubated at 37° C. for 5 minutes.

Primer extension reactions: 30 μl extension reactions were performed as follows: 0.1 μl of labeled open circle probe was added to ligation and ERCA reaction mix containing: 1 μl Ampligase buffer (20 mM Tris-HCl, pH 8.3) (Epicentre Technologies), 3 μl 10× modified ThermoPol reaction buffer (200 mM Tris-HCl, pH 8.8, 100 mM KCl, 100 mM $(NH_4)_2SO_4$ and 1% Triton X-100), 3 μl 50% TMA oxalate, 20.7 μl $dH_2O$, 1.2 μl 10 mM dNTP mix (dATP, dCTP, dGTP, and TTP), and 1 μl Bst polymerase (8 units/μl) (New England Biolabs, Massachusetts), the mix was incubated at 60° C.

3 μl Aliquots were pipetted out between 15 seconds and 2 hr time points and added into 3 μl 2× stop buffer (95% formamide, 20 mM EDTA, 0.05% bromophenol blue, and 0.05% xylene cyanol FF). Samples were then boiled for 5 minutes and electrophoresed on a 8% denaturing polyacrylamide gel. For each open circle probe, aliquot number one was taken prior to adding the polymerase enzyme, which represents the unextended open circle probe.

Results: A hairpin forms at the 3' end of the open circle probe that allowed the ERCA DNA polymerase to extend 54 bases from the self-annealed 3' end of the open circle probe. Full extension should have converted the hairpin open circle probe to an inert double-stranded form. This reaction, called the "suicide pathway", inactivates the open circle probe. The reaction was completed within 15 sec of the start of primer extension reaction.

Example 2

VCAM SNiPer Assay

This example describes single nucleotide polymorphism (SNP) detection on genomic DNA, using exponential rolling circle amplification (ERCA). Specifically, Exponential Rolling Circle Amplification is used for allele discrimination on genomic DNA on an ABI Prism 7700 Sequence Detection System using generic P1 Amplifluors as detection probes.

Oligonucleotide sequences:

```
VCAMinA sequence:
5'-phosphate-
AAATTGATTCAGGAAATACTAGCTTATAAAGACTCGTCATGTCTCAG
CTCTAGTTTCTGATCCCATGACTTCACCTACCAAATATCTAGGGATCA
GAA-3'
(SEQ ID NO:3)

VCAMocG sequence:
5'-phosphate-
AAATTGATTCAGGAAATACTAGCTTATAAAATGTTGACT GGT CAC
ACG TCGCTCTGATCCC ATG ACT TCA CCT ACC AAA TAT CTA
GGG ATC AGA G-3'
(SEQ ID NO:4)

VCAMinA P2:
CTTCACCTACCAAATATCTAGGGATCAGAA
(SEQ ID NO:5)

VCAMocG P21:
CTTCACCTACCAAATATCTAGGGATCAGAG
(SEQ ID NO:6)

P1 in Amplifluor:
5'-FAM-TCGATGACTGACGGTCATCG-Dabcyl-
dT)-ACTAGAGCTGAGACATGACGAGTC-3'
(SEQ ID NO:7(prior to Dabcyl-dT);
SEQ ID NO:8 (following Dabcyl-dT))

P1 oc Amplifluor:
5'-TET-TCGATGACTGACGGTCATCG-(Dabcyl-
dT)-ACGACGTGTGACCAGTCAACAT-3'
(SEQ ID NO:9 (prior to Dabcyl-dT);
SEQ ID NO:10 (following Dabcyl-dT))
```

Primer (P1) is an Amplifluor and is complementary to the region of the spacer region of an open circle probe. The sequence of the allele-specific primer (P2) is homologous to the 3' arm of an open circle probe. The Amplifluor P1s have either FAM or TET fluorophores at the 5' ends for the two alleles. The Tms of both these primers is approximately 65° C.

DNA Annealing and Ligation: The reactions were set up in 96-well MicroAmp Optical plates (Perkin Elmer) in a 10 µl reaction volume containing 1 unit Ampligase (Epicentre Technologies), 20 mM Tris-HCl (pH 8.3), 25 mM KCl, 10 mM MgCl$_2$, 0.5 mM NAD, and 0.01% Triton® X-100. Standard reactions contained 0.01 nM open circle probes and 100 ng of Alu I digested genomic DNA. DNA was denatured by heating the reactions at 95° C. for 3 min followed by annealing and ligation at 60° C. for 30 min.

ERCA™ Reaction: For each 30 µl reaction to be run, 20 µl of ERCA mix was added to the 10 µl ligation mix. ERCA mix was prepared as follows: 3 µl of 10×Bst Thermopol buffer (200 mM Tris-HCl, pH 8.8, 100 mM KCl, 100 mM (NH$_4$)$_2$SO$_4$ and 1% Triton X-100) containing no Mg$^{2+}$, 3 µl 50 mM TMA oxalate, 1.2 µl 10 mM dNTP mix (dATP, dGTP, dCTP, and dTTP), 3 µl 10 µM Amplifluor P1 primer, 3 µl 10 µM P2 primer, 2.5 µl 20 µM ROX dye, 1 µl of 8 units/µl Bst polymerase (New England Biolabs, Massachusetts), and 3.3 µl water. 20 µl of ERCA mix was added to the 10 µl ligation reaction. Real time ERCA reaction was performed in 96-well MicroAmp Optical Plates (Perkin-Elmer) and run on real time ABI Prism 7700 (Perkin-Elmer) for 3 hrs. Specific signal was expressed as "delta Ct".

Delta $Ct=(Ct$ minus ligase control$-Ct$ plus ligase).

Figure 5:
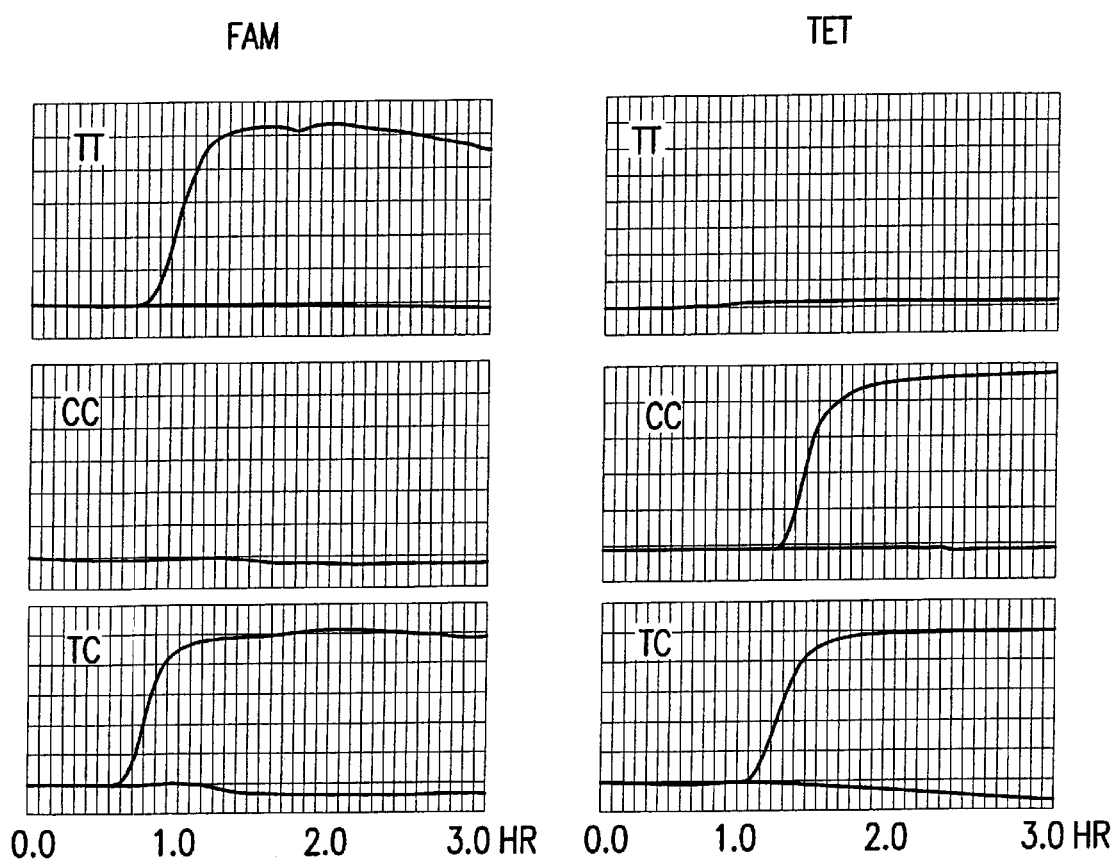
FIG. 5 depicts graphs of delta Ct versus time obtained from a real time ERCA reaction (Example 2).

Results: Genotyping assays with the hairpin open circle probe for the SNP VCAM gave a typical real time profiles (FIG. 5), and 98% overall accuracy (Table 1) when 92 genomic DNA samples were analyzed.

TABLE 1

| Genotype | Accuracy | % Accuracy |
|---|---|---|
| CT | 31/31 | 100.0% |
| TT (FAM-A) | 55156 | 98.2% |
| CC (TET-G) | 4/5 | 80.0% |
| Total | 90/92 | 98% |

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method of amplifying nucleic acid sequences, the method comprising
    a DNA ligation operation and an amplification operation,
    wherein the DNA ligation operation comprises circularization of one or more open circle probes,
    wherein each open circle probe comprises two ends,
    wherein at least one of the ends of at least one of the open circle probes can form an intramolecular stem structure,
    wherein circularization of the open circle probes that can form an intramolecular stem structure is dependent on hybridization of the open circle probe to a target sequence,
    wherein the amplification operation comprises rolling circle replication of the circularized open circle probes.

2. The method of claim 1
    wherein if one or more of the open circle probes that can form an intramolecular stem structure are not circularized, the end of at least one of the uncircularized open circle probes that forms the intramolecular stem structure is extended during the amplification operation using the open circle probe as a template.

3. The method of claim 2
    wherein extension of the end of the open circle probes prevents the extended open circle probes from serving as a template for rolling circle replication.

4. The method of claim 2
    wherein extension of the end of the open circle probes stabilizes the intramolecular stem structure,
    wherein the stabilized intramolecular stem structure prevents the extended open circle probes from priming nucleic acid replication.

5. The method of claim 1
    wherein the intramolecular stem structure can form under the conditions used for the amplification operation.

6. The method of claim 5 wherein the intramolecular stem structure prevents the open circle probes from priming nucleic acid replication.

7. The method of claim 5 wherein the intramolecular stem structure prevents the open circle probes from serving as a template for rolling circle replication.

8. The method of claim 1 wherein the intramolecular stem structure prevents the open circle probes from priming nucleic acid replication.

9. The method of claim 1 wherein the intramolecular stem structure prevents the open circle probes from serving as a template for rolling circle replication.

10. The method of claim 1 wherein the intramolecular stem structure forms a hairpin structure.

11. The method of claim 1 wherein the intramolecular stem structure forms a stem and loop structure.

12. The method of claim 11 wherein the two ends of the open circle probe together form the intramolecular stem structure.

13. The method of claim 1 wherein one of the ends of the open circle probes is a 3' end,
wherein the 3' end of at least one of the open circle probes can form an intramolecular stem structure.

14. The method of claim 13 wherein the other end of the open circle probes is a 5' end,
wherein the 5' end of at least one of the open circle probes can form an intramolecular stem structure.

15. The method of claim 12 wherein one of the ends of the open circle probes is a 5' end,
wherein the 5' end of at least one of the open circle probes can form an intramolecular stem structure.

16. The method of claim 1 wherein the open circle probes are each specific for a target sequence,
wherein each target sequence comprises a 5' region and a 3' region,
wherein each open circle probe comprises a single-stranded, linear DNA molecule,
wherein the single-stranded, linear DNA molecule comprises, from 5' end to 3' end, a 5' phosphate group, a right target probe portion, a spacer portion, a left target probe portion, and a 3' hydroxyl group,
wherein the left target probe portion is complementary to the 3' region of the target sequence,
wherein the right target probe portion is complementary to the 5' region of the target sequence.

17. The method of claim 16 wherein the intramolecular stem structure of at least one of the open circle probes forms a stem and loop structure.

18. The method of claim 17 wherein a portion of one of the target probe portions of at least one of the open circle probes is in the loop of the stem and loop structure,
wherein the portion of the target probe portion in the loop can hybridize to the target sequence,
wherein hybridization of the target probe portion in the loop to the target sequence disrupts the intramolecular stem structure.

19. The method of claim 18 wherein disruption of the intramolecular stem structure allows the end of the open circle probes that can form an intramolecular stem structure to hybridize to the target sequence.

20. The method of claim 19 wherein a hybrid between the target sequence and the target probe portion at the end of the open circle probes that can form an intramolecular stem structure is more stable than the intramolecular stem structure.

21. The method of claim 18 wherein hybridization of the loop to a sequence other than the target sequence does not disrupt the intramolecular stem structure.

22. The method of claim 16 wherein a hybrid between the target sequence and the target probe portion at the end of the open circle probes that can form an intramolecular stem structure is more stable than the intramolecular stem structure.

23. The method of claim 16 wherein the spacer portion comprises a primer complement portion.

24. The method of claim 16 wherein at least one of the target sequences further comprises a central region located between the 5' region and the 3' region,
wherein neither the left target probe portion of the open circle probe specific for the target sequence nor the right target probe portion of the open circle probe specific for the target sequence is complementary to the central region of the target sequence.

25. The method of claim 24 wherein the ligation operation comprises mixing the open circle probes and one or more gap oligonucleotides with one or more target samples, and incubating under conditions that promote
hybridization between the open circle probes and the gap oligonucleotides and the target sequences, and
ligation of the open circle probes and gap oligonucleotides to form the circularized open circle probes,
wherein each gap oligonucleotide comprises a single-stranded, linear DNA molecule comprising a 5' phosphate group and a 3' hydroxyl group, wherein each gap oligonucleotide is complementary all or a portion of the central region of the target sequence.

26. The method of claim 24 wherein a complement to the central region of the target sequence is synthesized during the ligation operation.

27. The method of claim 16 wherein a plurality of the open circle probes are each specific for a different target sequence.

28. The method of claim 27 wherein a plurality of different target sequences are detected.

29. The method of claim 27 wherein the amplification operation produces amplified nucleic acid, the method further comprising
detecting the amplified nucleic acid with one or more detection probes.

30. The method of claim 29 wherein a portion of each of a plurality of the detection probes has sequence matching or complementary to a portion of a different one of the open circle probes, wherein a plurality of different amplified nucleic acids are detected using the plurality of detection probes.

31. The method of claim 1 wherein at least one of the target sequences is coupled to a specific binding molecule.

32. The method of claim 31

33. The method of claim 32 wherein the specific binding molecule and target molecule are brought into contact prior to the ligation operation.

34. The method of claim 32 wherein the specific binding molecule and target molecule are brought into contact following the ligation operation.

35. The method of claim 32 wherein the specific binding molecule and target molecule are brought into contact following the amplification operation.

36. The method of claim 32 wherein the target molecule is a peptide, protein, carbohydrate, lipid, nucleic acid, or metabolite.

37. The method of claim 32 wherein the target molecule is present in, or derived from, tissue, bodily fluid, or cells.

38. The method of claim 32 wherein the target molecule is present in, or derived from, tissue.

39. The method of claim 31 wherein the specific binding molecule is an antibody.

40. The method of claim 31 wherein a plurality of different target sequences are coupled to specific binding molecules.

41. The method of claim 40 wherein at least one of the specific binding molecules is specific for a protein or peptide.

42. The method of claim 41 wherein a plurality of specific binding molecules are each specific for a different protein or peptide.

43. The method of claim 40 wherein a plurality of the specific binding molecules are each specific for a different analyte.

44. The method of claim 40 wherein a plurality of the specific binding molecules are each specific for a different target molecule, wherein the open circle probes are each specific for a different target sequence.

45. The method of claim 44 further comprising bringing into contact the specific binding molecules and one or more target molecules, wherein the specific binding molecule binds to the target molecule, wherein a plurality of different target molecules are detected via rolling circle replication of circularized open circle probes specific for the target sequences coupled to the specific binding molecules that are specific for the target molecules.

46. The method of claim 45 wherein a plurality of different target molecules are detected in the same assay.

47. The method of claim 1 wherein rolling circle replication is primed by a rolling circle replication primer, wherein the rolling circle replication primer is coupled to a specific binding molecule, wherein the specific binding molecule is bound to a target molecule.

48. The method of claim 1 wherein the amplification operation produces tandem sequence DNA, wherein the method further comprises detecting the tandem sequence DNA.

49. The method of claim 1 wherein the amplification operation produces tandem sequence DNA and secondary tandem sequence DNA, wherein the method further comprises detecting the tandem sequence DNA, the secondary tandem sequence DNA, or both.

50. The method of claim 1 wherein rolling circle replication is primed by one or more rolling circle replication primers, wherein each rolling circle replication primer comprises two ends, wherein at least one of the ends of at least one of the rolling circle replication primers can form an intramolecular stem structure, wherein priming by the rolling circle replication primers that can form an intramolecular stem structure is dependent on hybridization of the rolling circle replication primers to the amplification target circles.

51. The method of claim 50 wherein both ends of at least one of the rolling circle replication primers can form an intramolecular stem structure.

52. The method of claim 51 wherein the two ends of at least one of the rolling circle replication primers are hybridized to each other.

53. The method of claim 51 wherein the two ends of at least one of the rolling circle replication primers are a 3' end and a 5' end, wherein the 3' end and 5' end are both involved in the intramolecular stem structure such that the 3' end has a short unpaired overhang when the intramolecular stem structure is formed.

54. The method of claim 50 wherein the intramolecular stem structure of at least one of the rolling circle replication primers forms a stem and loop structure.

55. The method of claim 54 wherein each amplification target circle comprises a primer complement portion, wherein each rolling circle replication primer has a complement portion, wherein the complement portion of each rolling circle replication primer is complementary to the primer complement portion of at least one of the amplification target circles, wherein a portion of the complement portion of at least one of the rolling circle replication primers is in the loop of the stem and loop structure, wherein the portion of the complement portion in the loop can hybridize to the primer complement portion of at least one of the amplification target circles, wherein hybridization of the complement portion in the loop to the primer complement portion disrupts the intramolecular stem structure.

56. The method of claim 55 wherein disruption of the intramolecular stem structure allows the end of the rolling circle replication primers that can form an intramolecular stem structure to hybridize to the primer complement portion of the amplification target circle.

57. The method of claim 56 wherein a hybrid between the primer complement portion of the amplification target circle and the complement portion of the rolling circle replication primers that can form an intramolecular stem structure is more stable than the intramolecular stem structure.

58. The method of claim 55 wherein hybridization of the loop to a sequence other than the primer complement portion of the amplification target circle does not disrupt the intramolecular stem structure.

59. The method of claim 1 wherein the amplification operation produces tandem sequence DNA, wherein the amplification operation further comprises secondary DNA strand displacement.

60. The method of claim 59 wherein secondary DNA strand displacement is primed by one or more secondary DNA strand displacement primers, wherein each secondary DNA strand displacement primer comprises two ends, wherein at least one of the ends of at least one of the secondary DNA strand displacement primers can form an intramolecular stem structure, wherein priming by the secondary DNA strand displacement primers that can form an intramolecular stem structure is dependent on hybridization of the secondary DNA strand displacement primers to the tandem sequence DNA.

61. The method of claim 60 wherein the secondary DNA strand displacement primers prime secondary DNA strand displacement by hybridizing to the tandem sequence DNA, wherein both ends of at least one of the secondary DNA strand displacement primers can form an intramolecular stem structure.

62. The method of claim 61 wherein the two ends of at least one of the secondary DNA strand displacement primers are hybridized to each other.

63. The method of claim 61 wherein the two ends of at least one of the secondary DNA strand displacement primers are a 3' end and a 5' end, wherein the 3' end and 5' end are both involved in the intramolecular stem structure such that the 3' end has a short unpaired overhang when the intramolecular stem structure is formed.

64. The method of claim 60 wherein the intramolecular stem structure of at least one of the secondary DNA strand displacement primers forms a stem and loop structure.

65. The method of claim 64 wherein each secondary DNA strand displacement primer has a matching portion, wherein the matching portion of each secondary DNA strand displacement primer is complementary to the tandem sequence DNA, wherein a portion of the matching portion of at least one of the secondary DNA strand displacement primers is in the loop of the stem and loop structure, wherein the portion of the matching portion in the loop can hybridize to the tandem sequence DNA, wherein hybridization of the matching portion in the loop to the tandem sequence DNA disrupts the intramolecular stem structure.

66. The method of claim 65 wherein disruption of the intramolecular stem structure allows the end of the secondary DNA strand displacement primers that can form an intramolecular stem structure to hybridize to the tandem sequence DNA.

67. The method of claim 66 wherein a hybrid between the tandem sequence DNA and the matching portion of the secondary DNA strand displacement primers that can form an intramolecular stem structure is more stable than the intramolecular stem structure.

68. The method of claim 65 wherein hybridization of the loop to a sequence other than sequence in the tandem sequence DNA does not disrupt the intramolecular stem structure.

69. A method of selectively amplifying nucleic acid sequences related to one or more target sequences, the method comprising,
(a) mixing one or more different open circle probes with a target sample, to produce an OCP-target sample mixture, and incubating the OCP-target sample mixture under conditions that promote hybridization between the open circle probes and the target sequences in the OCP-target sample mixture,
(b) mixing ligase with the OCP-target sample mixture, to produce a ligation mixture, and incubating the ligation mixture under conditions that promote ligation of the open circle probes to form amplification target circles,
(c) mixing a rolling circle replication primer with the ligation mixture, to produce a primer-ATC mixture, and incubating the primer-ATC mixture under conditions that promote hybridization between the amplification target circles and the rolling circle replication primer in the primer-ATC mixture, and
(d) mixing DNA polymerase with the primer-ATC mixture, to produce a polymerase-ATC mixture, and incubating the polymerase-ATC mixture under conditions that promote replication of the amplification target circles,
wherein replication of the amplification target circles results in the formation of tandem sequence DNA;
wherein at least one of the open circle probes comprises two ends,
wherein at least one of the ends of the open circle probe can form an intramolecular stem structure.

70. The method of claim 69 wherein if the open circle probe that can form an intramolecular stem structure is not ligated to form an amplification target circle the end of the open circle probe is extended during replication of the amplification target circles using the open circle probe as a template.

71. The method of claim 70 wherein extension of the end of the open circle probe prevents the extended open circle probes from serving as a template for rolling circle replication.

72. The method of claim 70 wherein extension of the end of the open circle probe stabilizes the intramolecular stem structure, wherein the stabilized intramolecular stem structure prevents the extended open circle probes from priming nucleic acid replication.

73. The method of claim 69 wherein the intramolecular stem structure can form under the conditions used for replication of the amplification target circles.

74. The method of 73 wherein the intramolecular stem structure prevents the open circle probe that can form an intramolecular stem structure from priming nucleic acid replication.

75. The method of 73 wherein the intramolecular stem structure prevents the open circle probe that can form an intramolecular stem structure from serving as a template for rolling circle replication.

76. The method of 69 wherein the intramolecular stem structure prevents the open circle probe that can form an intramolecular stem structure from priming nucleic acid replication.

77. The method of 69 wherein the intramolecular stem structure prevents the open circle probe that can form an intramolecular stem structure from serving as a template for rolling circle replication.

78. The method of claim 69 wherein the intramolecular stem structure forms a hairpin structure.

79. The method of claim 69 wherein the intramolecular stem structure forms a stem and loop structure.

80. The method of claim 79 wherein the two ends of the open circle probe that can form an intramolecular stem structure together form the intramolecular stem structure.

81. The method of claim 69 wherein one of the ends of the open circle probe that can form an intramolecular stem structure is a 3' end, wherein the 3' end of the open circle probe can form an intramolecular stem structure.

82. The method of claim 81 wherein the other end of the open circle probe is a 5' end, wherein the 5' end of the open circle probe can form an intramolecular stem structure.

83. The method of claim 80 wherein one of the ends of the open circle probe is a 5' end, wherein the 5' end of the open circle probe can form an intramolecular stem structure.

84. The method of claim 69 wherein the target sequence to which the open circle probe that can form an intramolecular stem structure can hybridize comprises a 5' region and a 3' region, wherein the open circle probe comprises a single-stranded, linear DNA molecule, wherein the single-stranded, linear DNA molecule comprises, from 5' end to 3' end, a 5' phosphate group, a right target probe portion, a spacer portion, a left target probe portion, and a 3' hydroxyl group, wherein the left target probe portion is complementary to the 3' region of the target sequence, wherein the right target probe portion is complementary to the 5' region of the target sequence.

85. The method of claim 84 wherein the intramolecular stem structure forms a stem and loop structure.

86. The method of claim 85 wherein a portion of one of the target probe portions is in the loop of the stem and loop structure, wherein the portion of the target probe portion in the loop can hybridize to the target sequence, wherein hybridization of the target probe portion in the loop to the target sequence disrupts the intramolecular stem structure.

87. The method of claim 86 wherein disruption of the intramolecular stem structure allows the end of the open circle probe that can form an intramolecular stem structure to hybridize to the target sequence.

88. The method of claim 87 wherein a hybrid between the target sequence and the target probe portion at the end of the open circle probe that can form an intramolecular stem structure is more stable than the intramolecular stem structure.

89. The method of claim 84 wherein a hybrid between the target sequence and the target probe portion at the end of the open circle probe that can form an intramolecular stem structure is more stable than the intramolecular stem structure.

90. The method of claim 84 wherein the spacer portion comprises a primer complement portion.

91. The method of claim 84 wherein the target sequence further comprises a central region located between the 5' region and the 3' region, wherein neither the left target probe portion of the open circle probe nor the right target probe portion of the open circle probe is complementary to the central region of the target sequence.

92. The method of claim 91 wherein step (a) further comprises mixing one or more gap oligonucleotides with the target sample, wherein each gap oligonucleotide comprises a single-stranded, linear DNA molecule comprising a 5' phosphate group and a 3' hydroxyl group, wherein each gap oligonucleotide is complementary all or a portion of the central region of the target sequence.

93. The method of claim 91 wherein a complement to the central region of the target sequence is synthesized during step (b).

94. The method of claim 69 wherein at least one of the target sequences is coupled to a specific binding molecule.

95. The method of claim 94 wherein the method further comprises bringing into contact the specific binding molecule and a target molecule, wherein the specific binding molecule binds to a target molecule.

96. The method of claim 95 wherein the specific binding molecule and target molecule are brought into contact prior to step (a).

97. The method of claim 95 wherein the specific binding molecule and target molecule are brought into contact following step (b).

98. The method of claim 95 wherein the specific binding molecule and target molecule are brought into contact following step (d).

99. The method of claim 95
wherein the target molecule is a peptide, protein, carbohydrate, lipid, nucleic acid, or metabolite.

100. The method of claim 95
wherein the target molecule is present in, or derived from, tissue, bodily fluid, or cells.

101. The method of claim 95
wherein the target molecule is present in, or derived from, tissue.

102. The method of claim 94
wherein the specific binding molecule is an antibody.

103. The method of claim 94
wherein the rolling circle replication primer is coupled to a specific binding molecule,
wherein the specific binding molecule is bound to a target molecule.

104. The method of claim 69
wherein the method further comprises detecting the tandem sequence DNA.

105. The method of claim 69
wherein the tandem sequence DNA is replicated to form secondary tandem sequence DNA,
wherein the method further comprises detecting the tandem sequence DNA, the secondary tandem sequence DNA, or both.

* * * * *

SEQUENCE LISTING

<160> NUMBER OF SEQ ID NOS: 10

<210> SEQ ID NO 1
<211> LENGTH: 89
<212> TYPE: DNA

<213> ORGANISM: Artificial Sequence
<220> FEATURE:
<223> OTHER INFORMATION: Description of artificial sequence note = synthetic construct

<400> SEQUENCE: 1
gaagaactgg acagatttac tacgtatgtt gactggtcac acgtcgttct agtacgcttc    60
tactccctct tgagatgttc tgctttgtt                                      89

<210> SEQ ID NO 2
<211> LENGTH: 89
<212> TYPE: DNA
<213> ORGANISM: Artificial Sequence
<220> FEATURE:
<223> OTHER INFORMATION: Description of artificial sequence note = synthetic construct

<400> SEQUENCE: 2
gaagaactgg acagatttac tacgtatgtt gactggtcac acgtcgttct agtaacaaag    60
cactccctct tgagatgttc tgctttgtt                                      89

<210> SEQ ID NO 3
<211> LENGTH: 98
<212> TYPE: DNA
<213> ORGANISM: Artificial Sequence
<220> FEATURE:
<223> OTHER INFORMATION: Description of artificial sequence note = synthetic construct

<400> SEQUENCE: 3
aaattgattc aggaaatact agcttataaa gactcgtcat gtctcagctc tagtttctga    60
tcccatgact tcacctacca aatatctagg gatcagaa                            98

<210> SEQ ID NO 4
<211> LENGTH: 94
<212> TYPE: DNA
<213> ORGANISM: Artificial Sequence
<220> FEATURE:
<223> OTHER INFORMATION: Description of artificial sequence note = synthetic construct

<400> SEQUENCE: 4
aaattgattc aggaaatact agcttataaa atgttgactg gtcacacgtc gctctgatcc    60
catgacttca cctaccaaat atctagggat caga                                94

<210> SEQ ID NO 5
<211> LENGTH: 30
<212> TYPE: DNA
<213> ORGANISM: Artificial Sequence
<220> FEATURE:
<223> OTHER INFORMATION: Description of artificial sequence note = synthetic construct

<400> SEQUENCE: 5
cttcacctac caaatatcta gggatcagaa                                     30

<210> SEQ ID NO 6
<211> LENGTH: 30
<212> TYPE: DNA
<213> ORGANISM: Artificial Sequence
<220> FEATURE:
<223> OTHER INFORMATION: Description of artificial sequence note = synthetic construct

<400> SEQUENCE: 6

```
cttcacctac caaatatcta gggatcagag                                              30

<210> SEQ ID NO 7
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 7
tcgatgactg acggtcatcg                                                         20

<210> SEQ ID NO 8
<211> LENGTH: 24
<212> TYPE: DNA
<213> ORGANISM: Artificial Sequence
<220> FEATURE:
<223> OTHER INFORMATION: Description of artificial sequence note =
      synthetic construct

<400> SEQUENCE: 8
actagagctg agacatgacg agtc                                                    24

<210> SEQ ID NO 9
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 9
tcgatgactg acggtcatcg                                                         20

<210> SEQ ID NO 10
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 10
acgacgtgtg accagtcaac at                                                      22
```